(12) United States Patent
Fukushima et al.

(10) Patent No.: US 9,665,002 B2
(45) Date of Patent: May 30, 2017

(54) ONIUM SALT COMPOUND, RESIST COMPOSITION, AND PATTERN FORMING PROCESS

(71) Applicant: Shin-Etsu Chemical Co., Ltd., Tokyo (JP)

(72) Inventors: Masahiro Fukushima, Joetsu (JP); Masaki Ohashi, Joetsu (JP); Jun Hatakeyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/930,869

(22) Filed: Nov. 3, 2015

(65) Prior Publication Data

US 2016/0131972 A1 May 12, 2016

(30) Foreign Application Priority Data

Nov. 7, 2014 (JP) ................................. 2014-226553

(51) Int. Cl.

| | |
|---|---|
| *G03F 7/039* | (2006.01) |
| *G03F 7/004* | (2006.01) |
| *G03F 7/30* | (2006.01) |
| *G03F 7/32* | (2006.01) |
| *G03F 7/38* | (2006.01) |
| *G03F 7/20* | (2006.01) |
| *C07D 263/04* | (2006.01) |
| *C07D 233/02* | (2006.01) |
| *C07D 277/04* | (2006.01) |
| *C07D 207/04* | (2006.01) |
| *C07D 279/12* | (2006.01) |
| *C07D 295/112* | (2006.01) |
| *C07D 203/14* | (2006.01) |
| *C07D 241/04* | (2006.01) |
| *C07D 225/02* | (2006.01) |
| *C07D 223/04* | (2006.01) |
| *C07D 211/06* | (2006.01) |
| *C07D 205/04* | (2006.01) |
| *C07D 265/30* | (2006.01) |
| *C07D 295/155* | (2006.01) |
| *C07D 213/79* | (2006.01) |
| *C07D 295/26* | (2006.01) |
| *C07C 381/12* | (2006.01) |
| *G03F 7/16* | (2006.01) |
| *C07C 25/00* | (2006.01) |
| *C07C 69/78* | (2006.01) |
| *C07C 69/76* | (2006.01) |
| *C07C 25/02* | (2006.01) |

(52) U.S. Cl.
CPC ............ *G03F 7/0397* (2013.01); *C07C 25/00* (2013.01); *C07C 25/02* (2013.01); *C07C 69/76* (2013.01); *C07C 69/78* (2013.01); *C07C 381/12* (2013.01); *C07D 203/14* (2013.01); *C07D 205/04* (2013.01); *C07D 207/04* (2013.01); *C07D 211/06* (2013.01); *C07D 213/79* (2013.01); *C07D 223/04* (2013.01); *C07D 225/02* (2013.01); *C07D 233/02* (2013.01); *C07D 241/04* (2013.01); *C07D 263/04* (2013.01); *C07D 265/30* (2013.01); *C07D 277/04* (2013.01); *C07D 279/12* (2013.01); *C07D 295/112* (2013.01); *C07D 295/155* (2013.01); *C07D 295/26* (2013.01); *G03F 7/0045* (2013.01); *G03F 7/0046* (2013.01); *G03F 7/168* (2013.01); *G03F 7/2037* (2013.01); *G03F 7/2041* (2013.01); *G03F 7/30* (2013.01); *G03F 7/322* (2013.01); *G03F 7/325* (2013.01); *G03F 7/38* (2013.01)

(58) Field of Classification Search
None
See application file for complete search history.

(56) References Cited

U.S. PATENT DOCUMENTS

| | | | |
|---|---|---|---|
| 6,492,091 B2 | 12/2002 | Kodama et al. | |
| 7,923,199 B2 | 4/2011 | Wada | |
| 8,846,291 B2 | 9/2014 | Utsumi et al. | |
| 2007/0224540 A1 | 9/2007 | Kamimura et al. | |
| 2009/0233223 A1* | 9/2009 | Tachibana ............. | G03F 7/0045 430/270.1 |
| 2011/0212390 A1 | 9/2011 | Masunaga et al. | |
| 2016/0246175 A1* | 8/2016 | Kotake ................. | G03F 7/0392 |
| 2016/0299428 A1* | 10/2016 | Masunaga ............. | G03F 7/0045 |

FOREIGN PATENT DOCUMENTS

| | | | |
|---|---|---|---|
| GB | 946870 | * | 1/1964 |
| JP | 2006-208781 A | | 8/2006 |
| JP | 2007-293250 A | | 11/2007 |
| JP | 4226803 B2 | | 2/2009 |
| JP | 2012-123189 A | | 6/2012 |
| JP | 2013-250433 | * | 12/2013 |

OTHER PUBLICATIONS

Machine-assisted English translation of JP 2013-250433 provided by JPO (2013).*
Office Action dated Jul. 6, 2016, issued in counterpart Taiwanese Patent Application No. 104136092. (4 pages).

* cited by examiner

*Primary Examiner* — Sin Lee
(74) *Attorney, Agent, or Firm* — Westerman, Hattori, Daniels & Adrian, LLP

(57) ABSTRACT

Sulfonium and iodonium salts of a carboxylate having an aromatic ring to which a nitrogen-containing alkyl or cyclic structure is attached are novel. The onium salt functions as an acid diffusion controlling agent in a resist composition, enabling to form a pattern of good profile with high resolution, improved MEF, LWR and DOF.

11 Claims, 1 Drawing Sheet

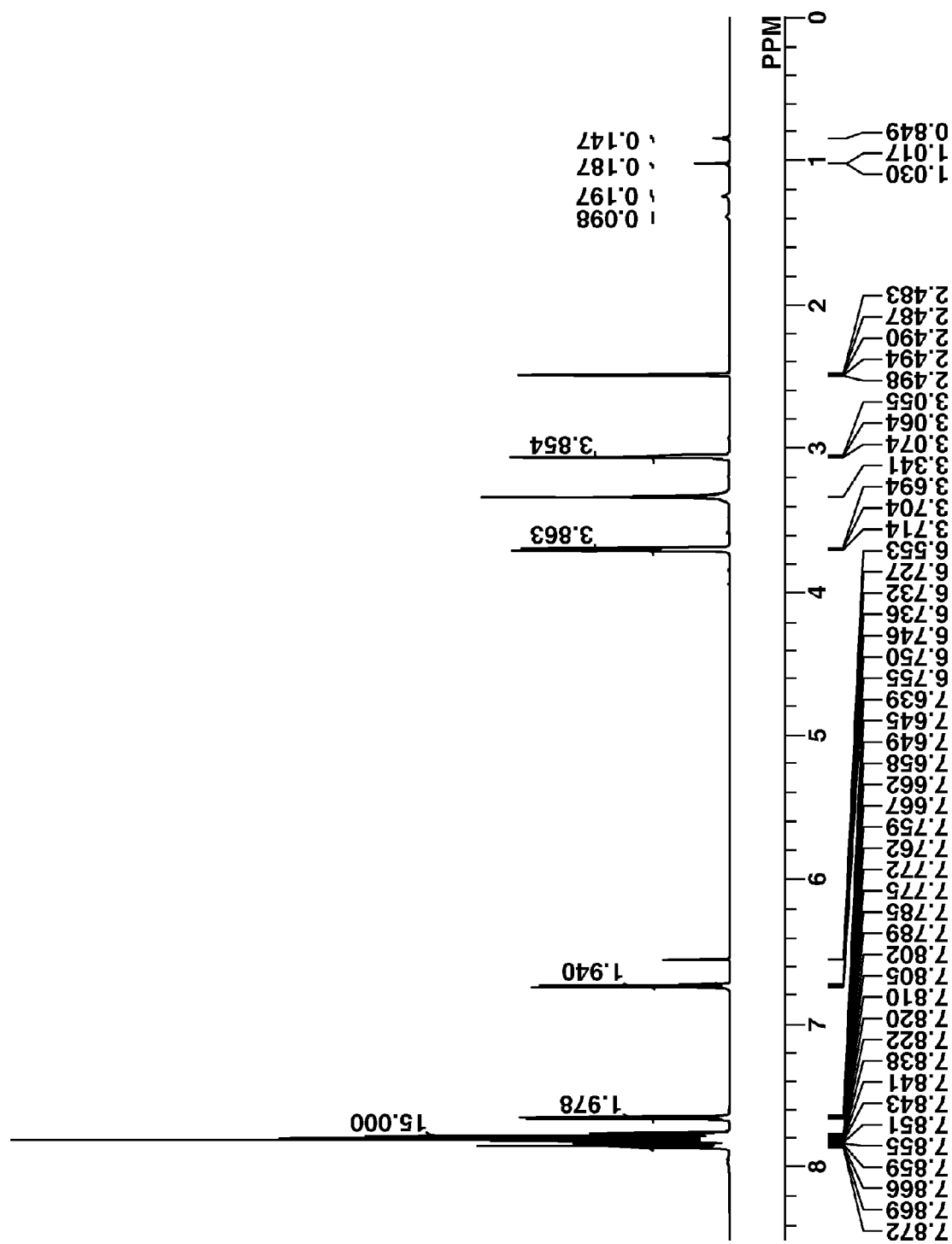

ONIUM SALT COMPOUND, RESIST COMPOSITION, AND PATTERN FORMING PROCESS

CROSS-REFERENCE TO RELATED APPLICATION

This non-provisional application claims priority under 35 U.S.C. §119(a) on Patent Application No. 2014-226553 filed in Japan on Nov. 7, 2014, the entire contents of which are hereby incorporated by reference.

TECHNICAL FIELD

This invention relates to an onium salt compound of specific structure, a resist composition, typically chemically amplified resist composition comprising the salt, and a pattern forming process using the resist composition.

BACKGROUND ART

While a number of recent efforts are being made to achieve a finer pattern rule in the drive for higher integration densities and operating speeds in LSI devices, DUV and EUV lithography is thought to hold particular promise as the next generation in microfabrication technology. In particular, photolithography using an ArF excimer laser as the light source is thought requisite to the micropatterning technique capable of achieving a feature size of 0.13 µm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. While the ArF immersion lithography has entered the commercial stage, the technology still needs a resist material which is substantially non-leachable in water.

In the ArF lithography (193 nm), a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polyacrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in enhancing the transparency of a resin alone.

With the rapid progress toward miniaturization, it becomes difficult to form a pattern of desired size from a resist material. In particular, the influence of acid diffusion is detrimental to lithography performance. As the pattern size is approaching the diffusion length of acid, the degradation of contrast becomes more serious. As the mask error factor (MEF), indicative of a dimensional shift on wafer relative to a dimensional shift on mask, increases, a noticeable drop of mask fidelity ensues. Further there is the tendency that the depth of focus becomes shallower as the wavelength of the light source becomes shorter. It is thus desired that the resist material have a depth of focus to enable resolution over a wide imaging range even when a light source of short wavelength is used. In addition, the fluctuation of pattern line width, known as line width roughness (LWR), becomes a problem. In the step of processing gate electrodes in the LSI circuit manufacturing process, for example, poor LWR gives rise to such problems as leak current, degrading electrical properties of transistors.

Accordingly, to take full advantage of wavelength reduction of the light source and increase of NA, it is ideal for a resist material that the acid generated therein be limited to exposed regions and uniformly distributed therein. It is thus necessary to control acid diffusion at a higher level than in prior art resist materials.

In addition to the above problems, the immersion lithography suffers from problems including a failure of resist pattern profile caused by defects resulting from microscopic water droplets left on the resist-coated wafer after exposure, and collapse or T-top configuration of resist pattern after development. For the immersion lithography as well, a pattern forming process capable of forming a satisfactory resist pattern after development is desired.

To solve the outstanding problems, studies are made not only on base resins and photoacid generators, but also on diffusion controlling agents. Amines are typically used as the diffusion controlling agent. Many problems associated with line width roughness (LWR) as an index of pattern roughness and pattern profile are left unsolved. Also use of weak acid onium salts as the diffusion controlling agent is under study. For example, Patent Document 1 describes a positive photosensitive composition for ArF excimer laser lithography comprising a carboxylic acid onium salt. The composition is based on the mechanism that a salt exchange occurs between a weak acid onium salt and a strong acid (sulfonic acid) generated by a PAG upon exposure, to form a weak acid and a strong acid onium salt. That is, the strong acid ($\alpha,\alpha$-difluorosulfonic acid) having high acidity is replaced by a weak acid (alkanesulfonic acid or carboxylic acid), thereby suppressing acid-aided decomposition reaction of acid labile group and reducing or controlling the distance of acid diffusion. The onium salt apparently functions as a quencher, that is, diffusion controlling agent. However, as the microfabrication technology is currently further advanced, the resist compositions using such weak acid onium salts become unsatisfactory with respect to resolution, MEF, LWR and depth of focus, particularly when processed by the ArF immersion lithography.

Patent Documents 2 and 3 describe photodegradable bases in the form of a sulfonium salt whose anion moiety has incorporated therein a nitrogen-containing substituent group, adapted to be decomposed to lose their basicity upon exposure. However, resist materials comprising these bases still lack the required lithography properties for the current generation of ArF lithography and ArF immersion lithography for ultrafine size processing. There is an increasing need for an effective acid diffusion controlling agent.

CITATION LIST

Patent Document 1: JP 4226803 (U.S. Pat. No. 6,492,091)
Patent Document 2: JP-A 2006-208781
Patent Document 3: JP-A 2012-123189

DISCLOSURE OF INVENTION

An object of the invention is to provide an onium salt compound effective as an acid diffusion controlling agent and a resist composition comprising the same, which composition is processed by KrF, ArF, EB or EUV lithography to form a resist pattern with high resolution, improved MEF, LWR, and DOF, and a pattern forming process using the resist composition.

The inventors have found that a resist composition comprising an onium salt compound of specific structure can be processed by lithography to form a resist pattern with high resolution, improved MEF, LWR and DOF, and is suited for high accuracy micropatterning.

In one aspect, the invention provides an onium salt compound having the general formula (1).

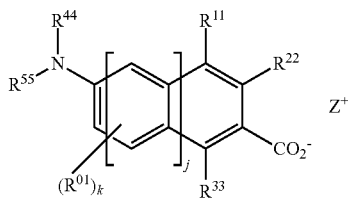
(1)

Herein $R^{11}$, $R^{22}$, $R^{33}$, $R^{44}$, $R^{55}$ and $R^{01}$ are each independently hydrogen, or a straight $C_1$-$C_{20}$ or branched or cyclic $C_3$-$C_{20}$ monovalent hydrocarbon group which may be substituted with or separated by a heteroatom, a pair of $R^{11}$ and $R^{22}$, or $R^{33}$ and $R^{01}$ may bond together to form a ring with the carbon atoms to which they are attached, or a pair of $R^{44}$ and $R^{55}$ may bond together to form a ring with the nitrogen atom to which they are attached, the ring may have an oxygen atom, sulfur atom or NH moiety interposed therein, j is 0 or 1, k is a number in the range: 0≤k≤1 when j=0 and 0≤k≤3 when j=1. $Z^+$ is a sulfonium cation of the general formula (a) or iodonium cation of the general formula (b):

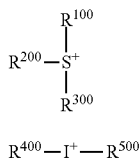
(a)

(b)

wherein $R^{100}$, $R^{200}$ and $R^{300}$ are each independently a straight $C_1$-$C_{20}$ or branched or cyclic $C_3$-$C_{20}$ monovalent hydrocarbon group which may be substituted with or separated by a heteroatom, or any two or more of $R^{100}$, $R^{200}$ and $R^{300}$ may bond together to form a ring with the sulfur atom, the ring may have a carbonyl moiety, sulfur atom, S(=O) moiety, $SO_2$ moiety, oxygen atom, or NH moiety interposed therein, $R^{400}$ and $R^{500}$ are each independently a straight $C_1$-$C_{20}$ or branched or cyclic $C_3$-$C_{20}$ monovalent hydrocarbon group which may be substituted with or separated by a heteroatom.

In another aspect, the invention provides a resist composition comprising (A) the onium salt compound defined above, (B) a polymer, (C) a photoacid generator, and (D) an organic solvent, the polymer comprising recurring units having the general formulae (2) and (3).

(2)

(3)

Herein $R^{1a}$ is hydrogen, fluorine, methyl or trifluoromethyl, $Z^a$ is a single bond, phenylene, naphthylene or (backbone)-C(=O)—O—Z'—, Z' is a straight $C_1$-$C_{10}$ or branched or cyclic $C_3$-$C_{10}$ alkylene group which may contain a hydroxyl moiety, ether bond, ester bond or lactone ring, or phenylene or naphthylene group, XA is an acid labile group, and YL is hydrogen or a polar group having at least one structure selected from the group consisting of hydroxyl, cyano, carbonyl, carboxyl, ether bond, ester bond, sulfonate bond, carbonate bond, lactone ring, sultone ring, and carboxylic anhydride.

Preferably, the polymer further comprises recurring units (d1) or (d2) having the general formula:

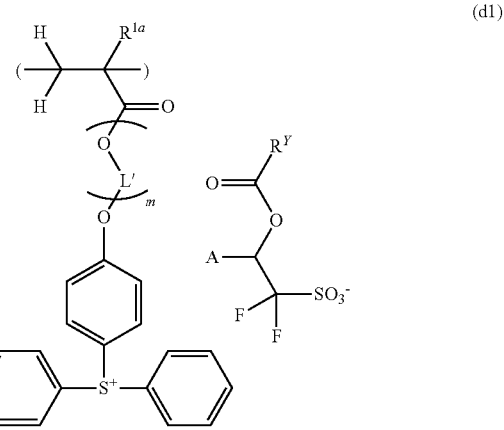
(d1)

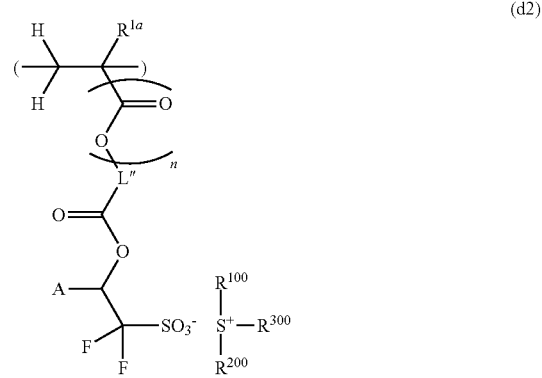
(d2)

wherein $R^{1a}$, $R^{100}$, $R^{200}$ and $R^{300}$ are is as defined above, L' is a $C_2$-$C_5$ alkylene group, $R^Y$ is a straight $C_1$-$C_{20}$, or branched or cyclic $C_3$-$C_{20}$ monovalent hydrocarbon group which may be substituted with or separated by a heteroatom, A is hydrogen or trifluoromethyl, L" is a single bond or a straight $C_1$-$C_{20}$ or branched or cyclic $C_3$-$C_{20}$ divalent hydrocarbon group which may be substituted with or separated by a heteroatom, m is 0 or 1, n is 0 or 1, with the proviso that n is 0 when L" is a single bond.

In a preferred embodiment, the photoacid generator has the general formula (4).

$$X^- \quad \begin{array}{c} R^{100} \\ | \\ S^+ - R^{300} \\ | \\ R^{200} \end{array} \quad (4)$$

Herein $R^{100}$, $R^{200}$, and $R^{300}$ are as defined above, $X^-$ is an anion of any one of the general formulae (5) to (8):

$$R^{fa} - CF_2 - SO_3^- \quad (5)$$

$$\begin{array}{c} R^{fb1} - CF_2 - SO_2 \\ \phantom{R^{fb1} - CF_2 -} \diagdown \\ \phantom{R^{fb1} - CF_2 - SO_2} N^- \\ \phantom{R^{fb1} - CF_2 -} \diagup \\ R^{fb2} - CF_2 - SO_2 \end{array} \quad (6)$$

$$R^{fc1} - CF_2 - SO_2 - \begin{array}{c} R^{fc2} \\ | \\ CF_2 \\ | \\ SO_2 \\ | \\ C^- \\ | \\ SO_2 \\ | \\ CF_2 \\ | \\ R^{fc3} \end{array} \quad (7)$$

$$R^{fd} - \underset{O}{\overset{O}{\|}}\!\!C - O - \underset{CF_3}{\overset{CF_3}{\underset{|}{C}}} - CH_2 - SO_3^- \quad (8)$$

wherein $R^{fa}$, $R^{fb1}$, $R^{fb2}$, $R^{fc1}$, $R^{fc2}$, and $R^{fc3}$ are each independently fluorine or a straight $C_1$-$C_{40}$ or branched or cyclic $C_3$-$C_{40}$ monovalent hydrocarbon group which may be substituted with or separated by a heteroatom, $R^{fb1}$ and $R^{fb2}$, or $R^{fc1}$ and $R^{fc2}$ may bond together to form a ring with the segments to which they are attached, $R^{fd}$ is a straight $C_1$-$C_{40}$ or branched or cyclic $C_3$-$C_{40}$ monovalent hydrocarbon group which may be substituted with or separated by a heteroatom.

The resist composition may further comprise a nonionic nitrogen-containing compound, and a surfactant which is insoluble or substantially insoluble in water and soluble in alkaline developer and/or a surfactant which is insoluble or substantially insoluble in water and alkaline developer.

In a further aspect, the invention provides a pattern forming process comprising the steps of applying the resist composition defined above onto a substrate, prebaking to form a resist film, exposing the resist film to KrF excimer laser, ArF excimer laser, EB or EUV through a photomask, baking, and developing the exposed resist film in a developer.

The exposing step is preferably by immersion lithography wherein a liquid having a refractive index of at least 1.0 is interposed between the resist film and a projection lens. In the immersion lithography, a protective film may be formed on the resist film, and the liquid is interposed between the protective film and the projection lens.

Advantageous Effects of Invention

Since the onium salt compound exerts a satisfactory function of acid diffusion controlling agent, the inventive resist composition comprising the same enables to form a pattern of good profile with a high resolution, low MEF, low LWR, and improved DOF.

BRIEF DESCRIPTION OF ACCOMPANYING DRAWINGS

FIG. 1 is a diagram of $^1$H-NMR spectrum of the compound obtained in Synthesis Example 1-1.

DESCRIPTION OF EMBODIMENTS

As used herein, the singular forms "a," "an" and "the" include plural referents unless the context clearly dictates otherwise. The notation (Cn-Cm) means a group containing from n to m carbon atoms per group.

The abbreviations and acronyms have the following meaning.
EB: electron beam
DUV: deep ultraviolet
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
MEF: mask error factor
LWR: line width roughness
DOF: depth of focus In structural formulae, the broken line denotes a valence bond; Ph stands for phenyl and Ac for acetyl.

(A) Acid Diffusion Controlling Agent (Onium Salt Compound)

The invention provides an onium salt compound having the general formula (1). This compound functions quite effectively as an acid diffusion controlling agent in a resist composition. In conjunction with a resist composition wherein an acid is generated by a PAG in the exposed region, the term "acid diffusion controlling agent" refers to a compound capable of trapping the generated acid to prevent the acid from diffusing into the unexposed region for thereby helping form the desired pattern. As long as the function is exerted, the structure of the compound is not particularly limited. Conventional acid diffusion controlling agents include amines and onium salts of weak acids (e.g., carboxylic acids).

$$(1)$$

[Structure showing a naphthalene-type ring system with substituents $R^{44}$, $R^{11}$, $R^{55}$, $R^{22}$, $R^{33}$, $(R^{01})_k$, $CO_2^-$, $Z^+$, with subscript $j$]

Herein $R^{11}$, $R^{22}$, $R^{33}$, $R^{44}$, $R^{55}$ and $R^{01}$ are each independently hydrogen, or a straight $C_1$-$C_{20}$ or branched or cyclic $C_3$-$C_{20}$ monovalent hydrocarbon group which may be substituted with or separated by a heteroatom, a pair of $R^{11}$ and $R^{22}$, or $R^{33}$ and $R^{01}$ may bond together to form a ring with the carbon atoms to which they are attached and the carbon atom(s) therebetween if any, or a pair of $R^{44}$ and $R^{55}$ may bond together to form a ring with the nitrogen atom to which they are attached, the ring may have an oxygen atom, sulfur atom or NH moiety interposed therein, j is 0 or 1, k is a number in the range: $0 \leq k \leq 1$ when $j=0$ and $0 \leq k \leq 3$ when $j=1$.

$Z^+$ is a sulfonium cation of the general formula (a) or iodonium cation of the general formula (b):

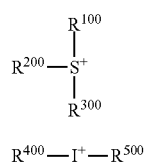

(a)

(b)

wherein $R^{100}$, $R^{200}$ and $R^{300}$ are each independently a straight $C_1$-$C_{20}$ or branched or cyclic $C_3$-$C_{20}$ monovalent hydrocarbon group which may be substituted with or separated by a heteroatom, or any two or more of $R^{100}$, $R^{200}$ and $R^{300}$ may bond together to form a ring with the sulfur atom, the ring may have a carbonyl moiety, sulfur atom, S(=O) moiety, $SO_2$ moiety, oxygen atom, or NH moiety interposed therein, $R^{400}$ and $R^{500}$ are each independently a straight $C_1$-$C_{20}$ or branched or cyclic $C_3$-$C_{20}$ monovalent hydrocarbon group which may be substituted with or separated by a heteroatom.

In formula (1), each of $R^{11}$, $R^{22}$, $R^{33}$, $R^{44}$, $R^{55}$ and $R^{01}$ is hydrogen, or a straight $C_1$-$C_{20}$ or branched or cyclic $C_3$-$C_{20}$ monovalent hydrocarbon group which may be substituted with or separated by a heteroatom. Specifically, suitable monovalent hydrocarbon groups include methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, adamantylmethyl, phenyl, naphthyl, and anthracenyl. In these groups, one or more hydrogen atom may be replaced by a heteroatom such as oxygen, sulfur, nitrogen, or halogen, or one or more carbon atom may be replaced by a heteroatom such as oxygen, sulfur or nitrogen, to form a hydroxyl group, cyano group, carbonyl group, ether bond, thioether bond, ester bond, sulfonate (sulfonic acid ester) bond, carbonate bond, carbamate bond, lactone ring, sultone ring, carboxylic anhydride or haloalkyl group.

With respect to the partial moiety of the formula:

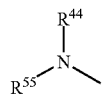

in formula (1), when $R^{44}$ and $R^{55}$ bond together to form a ring with the nitrogen atom, the ring is exemplified by the following structures.

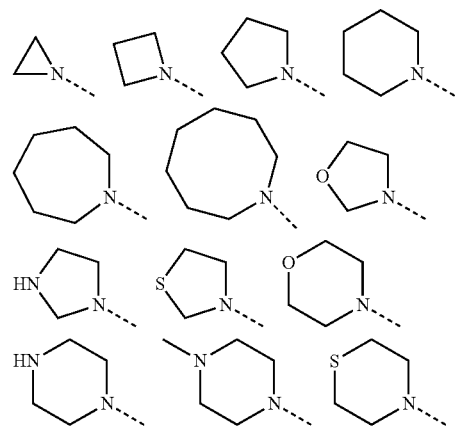

In the formulae, the broken line denotes a valence bond to the aromatic ring in formula (1).

Preferred structures for the anion moiety of the onium salt compound having formula (1) are shown below by formulae (A-1) to (A-43) although the invention is not limited thereto.

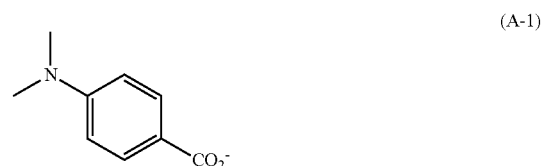

(A-1)

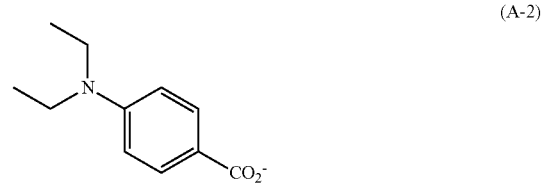

(A-2)

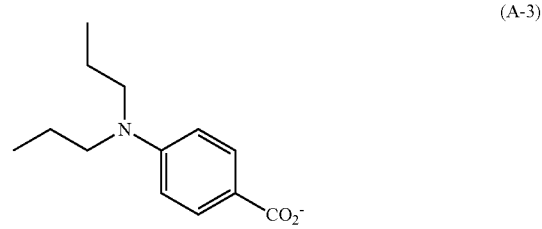

(A-3)

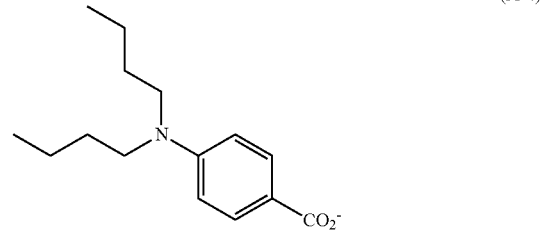

(A-4)

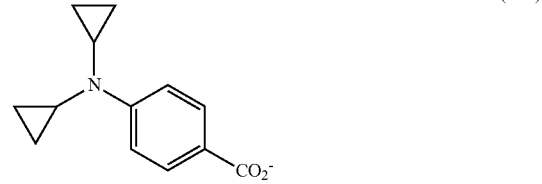

(A-5)

(A-6) 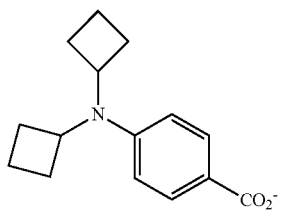
(A-7) 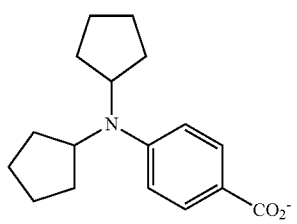
(A-8) 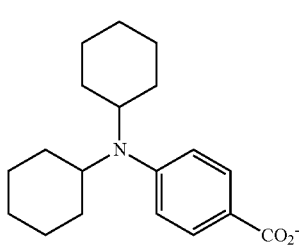
(A-9) 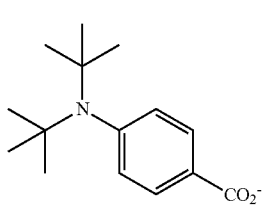
(A-10) 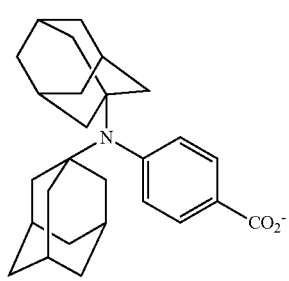
(A-11) 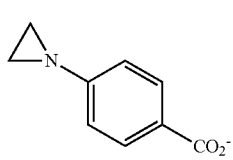
(A-12) 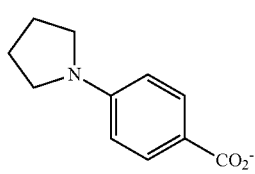
(A-13) 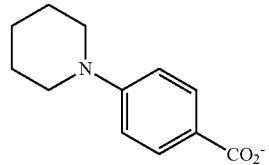
(A-14) 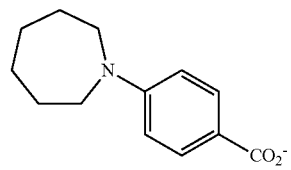
(A-15) 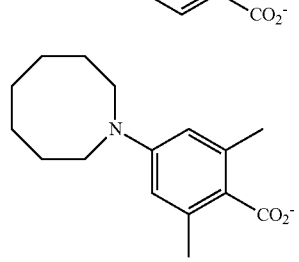
(A-16) 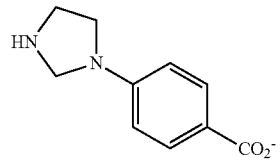
(A-17) 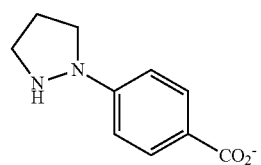
(A-18) 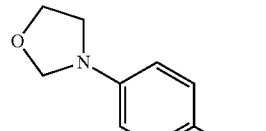
(A-19) 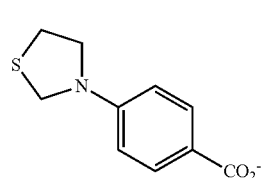
(A-20) 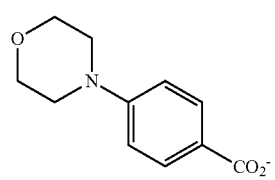
(A-21) 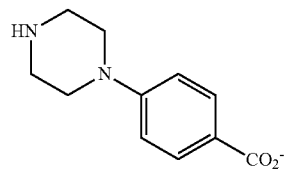

(A-22) 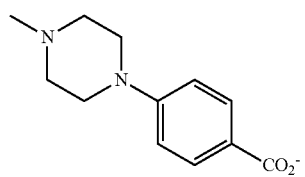
(A-23) 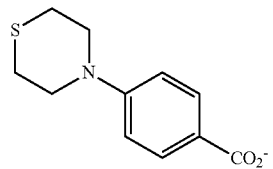
(A-24) 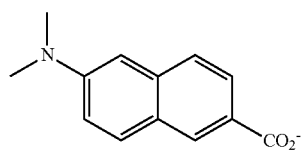
(A-25) 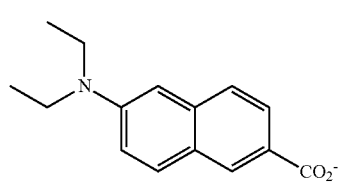
(A-26) 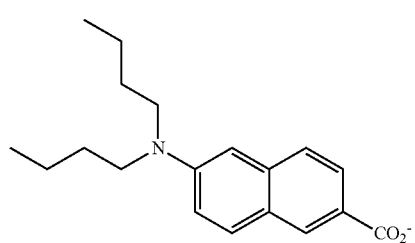
(A-27) 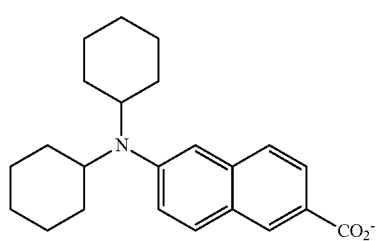
(A-28) 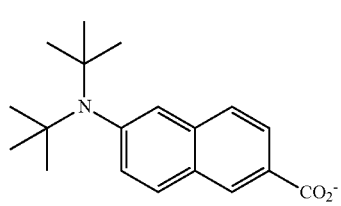
(A-29) 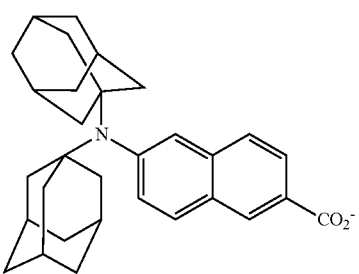
(A-30) 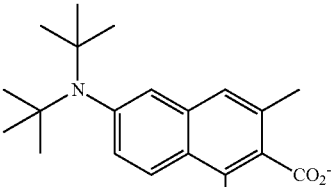
(A-31) 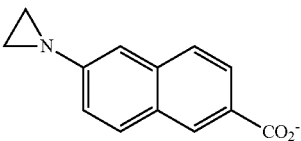
(A-32) 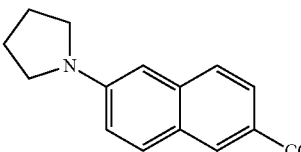
(A-33) 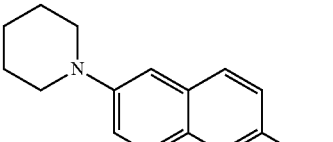
(A-34) 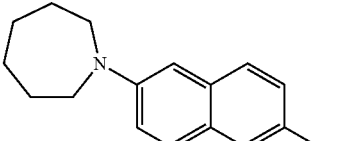
(A-35) 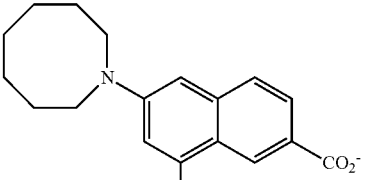
(A-36)

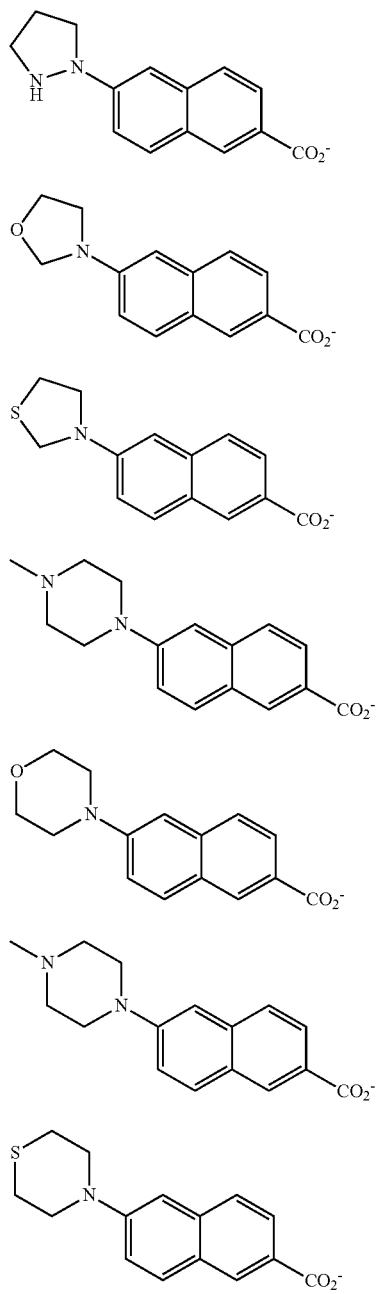

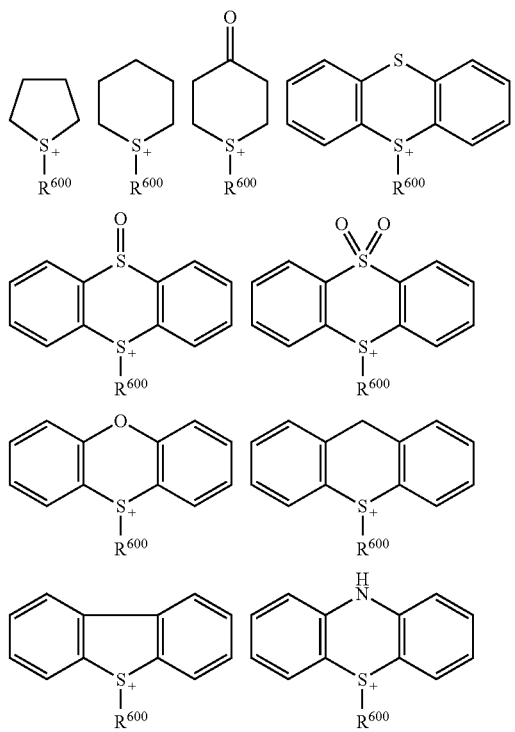

Herein, $R^{600}$ is a monovalent hydrocarbon group as exemplified above for $R^{100}$, $R^{200}$ and $R^{300}$.

Preferred structures for the sulfonium cation having formula (a) are shown below although the invention is not limited thereto.

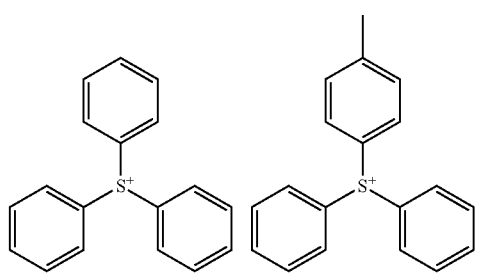

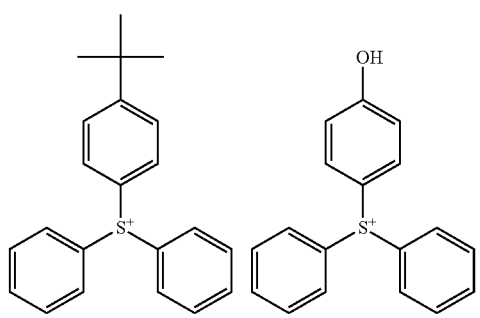

Of the anions of structural formulae (A-1) to (A-43), those of formulae (A-1) to (A-23) are especially preferred for availability of starting carboxylic acids and ease of synthesis.

In formula (a), $R^{100}$, $R^{200}$ and $R^{300}$ are each independently a straight $C_1$-$C_{20}$ or branched or cyclic $C_3$-$C_{20}$ monovalent hydrocarbon group which may be substituted with or separated by a heteroatom. Examples of the monovalent hydrocarbon group are as exemplified for $R^{11}$, $R^{22}$, $R^{33}$, $R^{44}$, $R^{55}$ and $R^{01}$ in formula (1). Also, any two or more of $R^{100}$, $R^{200}$ and $R^{300}$ may bond together to form a ring with the sulfur atom in formula (a), and the ring may have a carbonyl moiety, sulfur atom, S(=O) moiety, $SO_2$ moiety, oxygen atom, or NH moiety interposed therein. In this case, exemplary structures are shown below.

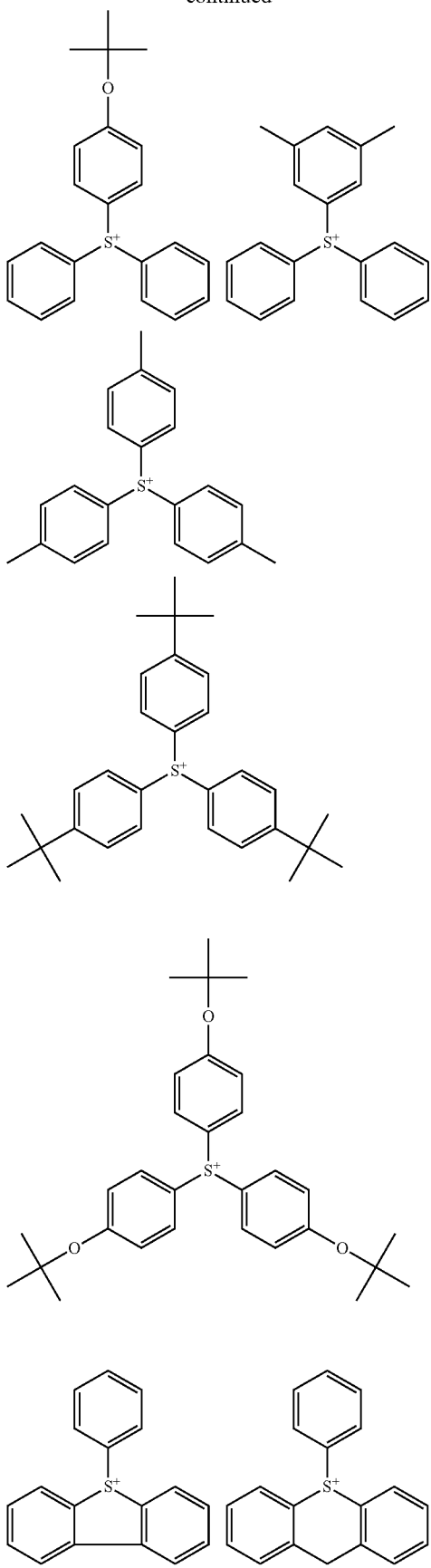
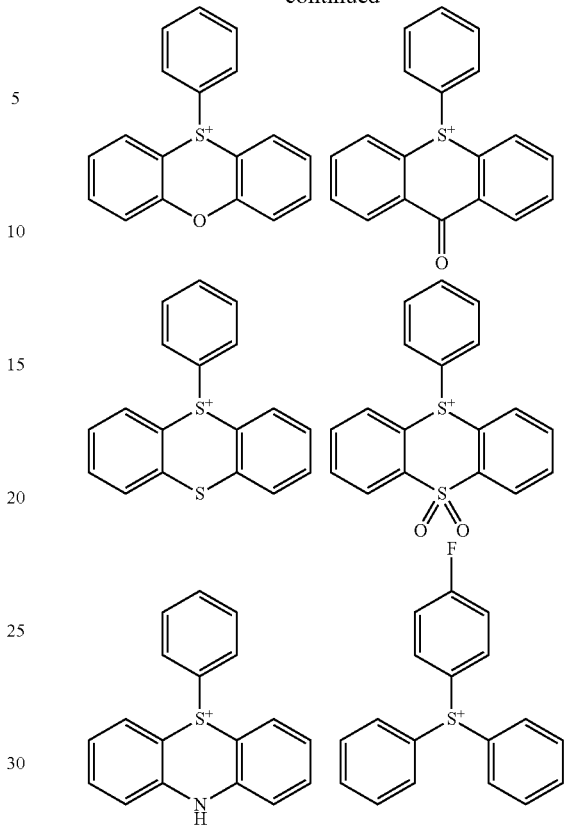

In formula (b), $R^{400}$ and $R^{500}$ are each independently a straight $C_1$-$C_{20}$ or branched or cyclic $C_3$-$C_{20}$ monovalent hydrocarbon group which may be substituted with or separated by a heteroatom. Examples of the monovalent hydrocarbon group are as exemplified for $R^{11}$, $R^{22}$, $R^{33}$, $R^{44}$, $R^{55}$ and $R^{o1}$ in formula (1). Inter alia, aryl is preferred.

Preferred examples of the iodonium cation having formula (b) include bis(4-methylphenyl)iodonium, bis(4-ethylphenyl)iodonium, bis(4-tert-butylphenyl)iodonium, bis(4-(1,1-dimethylpropyl)phenyl)iodonium, 4-methoxyphenylphenyliodonium, 4-tert-butoxyphenylphenyliodonium, 4-acryloyloxyphenylphenyliodonium, and 4-methacryloyloxyphenylphenyliodonium, with bis(4-tert-butylphenyl)iodonium being especially preferred.

Illustrative structures of the carboxylic acid sulfonium or iodonium salt include arbitrary combinations of the above-exemplified anion moieties with the above-exemplified cation moieties.

The carboxylic acid onium salt of the invention functions as an acid diffusion controlling agent. The acid diffusion controlling mechanism is estimated as follows. In a resist composition, a PAG generates an acid which must be strongly acidic enough to deprotect the acid labile group on the base resin, for example, α-fluorinated sulfonic acid, imidic acid or methidic acid in the case of ArF lithography. If a PAG and an acid diffusion controlling agent (according to the invention) are co-present in a resist composition, the acid generated by the PAG undergoes ion exchange with the acid diffusion controlling agent and is converted back to the sulfonium or iodonium salt and instead, the anion moiety of the acid diffusion controlling agent is released as carboxylic acid. Differently stated, through ion exchange, the strong acid is neutralized with the carboxylic acid onium salt. That is, the carboxylic acid onium salt according to the invention functions as an acid diffusion controlling agent. On the other hand, the mechanism that the cation moiety of the carboxylic acid onium salt is photodegraded to generate carboxylic acid may, of course, be contemplated. However, the acid generated via this mechanism is a weak acid which has not a sufficient acidity to deprotect the acid labile group on the base resin.

The acid diffusion controlling agent, which may also be referred to as onium salt type quencher, tends to form a resist pattern with a reduced LWR as compared with the conventional quenchers in the form of amine compounds. This is probably because salt exchange between strong acid and carboxylic acid onium salt is infinitely repeated. The site where strong acid is generated at the end of exposure shifts from the site where the onium salt of strong acid generation type is initially present. It is believed that since the cycle of photo-acid generation and salt exchange is repeated many times, the acid generation point is averaged, which leads to a resist pattern with reduced LWR after development.

As a matter of course, the acid diffusion controlling agent is present in the unexposed region as well. It is believed that the agent traps the acid having diffused from the exposed region to the unexposed region via the aforementioned ion exchange reaction. It is also believed that since the acid diffusion controlling agent has basic nitrogen in its anion moiety, the nitrogen directly traps the acid. Both the effects ensure to quench the acid having diffused from the exposed region to the unexposed region. It is expected that acid diffusion is substantially controlled. Thus the contrast between exposed and unexposed regions is enhanced, leading to substantial improvements in resolution and DOF.

As the compound that exerts a quencher effect by a similar mechanism, Patent Document 1 and JP-A H11-327143 report the use of carboxylic acid onium salts, alkylsulfonic acid onium salts, and arylsulfonic acid onium salts as the acid diffusion controlling agent. However, on use of an alkylsulfonic acid onium salt or arylsulfonic acid onium salt, the generated acid has a certain acid strength so that part thereof may induce deprotection reaction in the overexposed region rather than functioning as the quencher, to promote acid diffusion, leading to degradation of resist performance factors like resolution and MEF. Also, in the case of an alkanecarboxylic acid onium salt, the carboxylic acid generated therefrom has too weak an acidity to react with the acid labile group on the base resin. However, the alkanecarboxylic acid onium salt cannot fully trap the strong acid generated from the PAG and having diffused into the unexposed region, resulting in shortage of resolution and DOF. In contrast, the acid diffusion controlling agent of the invention has a quench ability due to both ion exchange and neutralization by reaction of nitrogen, and thus ensures to trap the acid having diffused into the unexposed region, as compared with the alkanecarboxylic acid onium salt.

Also, Patent Documents 2 and 3 describe a photodegradable base in the form of a sulfonium salt whose anion moiety has a nitrogen-containing substituent group incorporated therein, adapted to be decomposed to lose its basicity upon exposure. A high contrast is achievable since this base loses basicity in the exposed region, but maintains basicity in the unexposed region. In practice, however, control of acid diffusion is insufficient, and resist performance in terms of resolution and MEF is unsatisfactory. This is probably because the sulfonio acid generated from the photodegradable base in the exposed region also contributes to deprotection reaction along with the PAG.

On the other hand, JP-A 2007-293250 shows some sulfonium or iodonium salts of nitrogen-containing carboxylic acids though synthesis examples thereof are described nowhere. The nitrogen-containing carboxylates of monocyclic form generally have high water solubility and very low organic solvent solubility. Thus these salts are less compatible in resist compositions. These properties lead to a possibility to aggravate such performance as pattern profile and roughness in that the unexposed region is partially dissolved away in the positive resist process of alkaline development type, or the unexposed region is not fully dissolved and partially left in the negative tone process of organic solvent development type.

In contrast, the acid diffusion controlling agent of the invention is characterized in that the anion moiety is a carboxylate having an aromatic ring to which a nitrogen-containing alkyl group or nitrogen-containing cyclic structure is attached. Thus the agent has a high solubility in solvents and eliminates the possibility of performance aggravation by solubility as mentioned above. As previously discussed, the acid diffusion controlling agent also has the acid trapping function via ion exchange, whereby LWR is improved. Further, the acid diffusion controlling agent can trap the acid having diffused into the unexposed region by the quench function due to both ion exchange reaction and neutralization reaction of the heteroatom-containing site, thereby achieving an improvement in contrast, a high level of acid diffusion control, and improvements in lithography factors including MEF, DOF and resolution. The resist composition comprising the acid diffusion controlling agent is quite effective for micropatterning.

When the onium salt compound having formula (1) is added to a resist composition, it is preferably used in an amount of 0.1 to 40 parts, more preferably 1 to 20 parts by weight per 100 parts by weight of the base resin. Outside the range, a less amount of the compound may fail to achieve the full function whereas a larger amount may invite performance degradations such as a lowering of sensitivity and formation of foreign particles due to short solubility.

The onium salt compound having formula (1) may be readily synthesized by any organic chemistry procedures well known to the artisan in the art. For example, the desired compound may be synthesized by ion exchange reaction of a carboxylic acid as a precursor to the anion moiety in formula (1) with a cationic agent such as triarylsulfonium halide or diaryliodonium halide. The carboxylic acid as the starting reactant may be synthesized by any well-known organic chemistry procedures or any commercially available products may be used. One typical method for the synthesis of the carboxylic acid as the starting reactant is the Buchwald-Hartwig reaction of a halo-arene compound with an amine compound in the presence of a palladium complex catalyst. The ion exchange reaction may be readily carried out by any well-known techniques, with reference to JP-A 2007-145797, for example.

Resist Composition

Another embodiment of the invention is directed to a resist composition, typically chemically amplified resist composition, comprising (A) the onium salt compound or acid diffusion controlling agent of formula (1) as an essential component, (B) a polymer as a base resin, (C) a photoacid generator, and (D) an organic solvent. If necessary, the resist composition may further comprise (E) a nonionic nitrogen-containing compound, (F) a surfactant which is insoluble or substantially insoluble in water and soluble in alkaline developer, and/or a surfactant which is insoluble or substantially insoluble in water and alkaline developer (hydrophobic resin), and (G) an organic acid derivative and/or fluorinated alcohol.

(B) Base Resin

The base resin used in the resist composition is a polymer comprising recurring units having the general formula (2) and recurring units having the general formula (3).

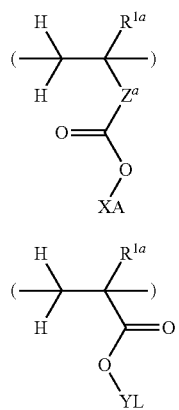

Herein $R^{1a}$ is hydrogen, fluorine, methyl or trifluoromethyl, $Z^a$ is a single bond, phenylene, naphthylene or (backbone)-C(=O)—O—Z'—, wherein Z' is a straight $C_1$-$C_{10}$ or branched or cyclic $C_3$-$C_{10}$, alkylene group which may contain a hydroxyl radical, ether bond, ester bond or lactone ring, or a phenylene or naphthylene group. XA is an acid labile group. YL is hydrogen or a polar group having at least one structure selected from the group consisting of hydroxyl, cyano, carbonyl, carboxyl, ether bond, ester bond, sulfonate bond, carbonate bond, lactone ring, sultone ring, and carboxylic anhydride.

Examples of the structure of formula (2) wherein $Z^a$ is a variant are illustrated below.

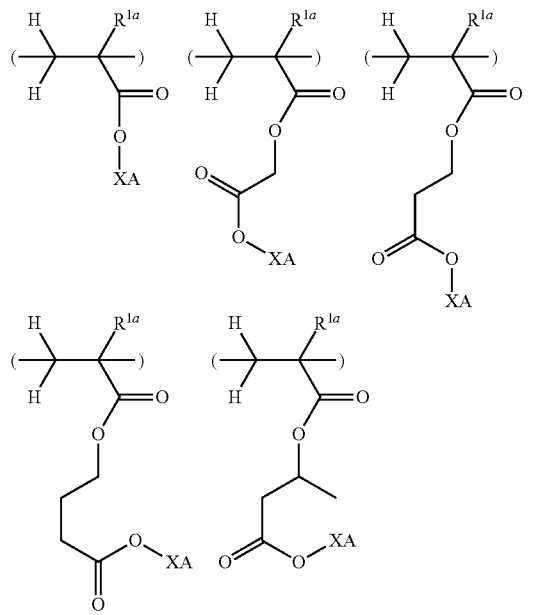

-continued

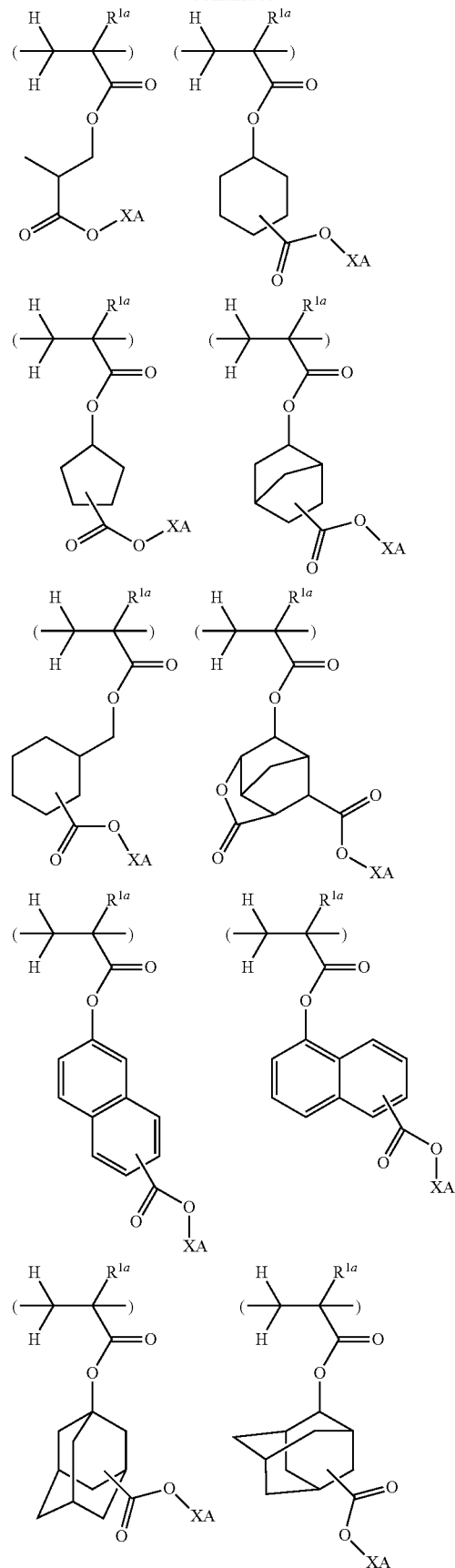

-continued

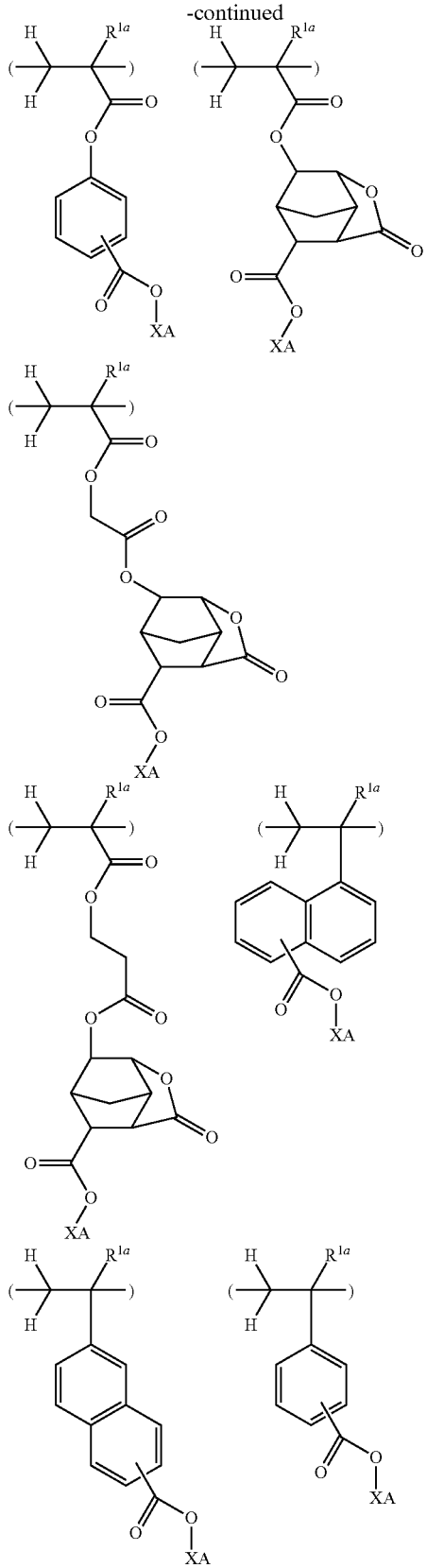

The polymer comprising recurring units having formula (2) functions such that it may be decomposed to generate carboxylic acid under the action of an acid and turn alkali soluble. The acid labile group represented by XA may be selected from a variety of such groups. Examples of the acid labile group include groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

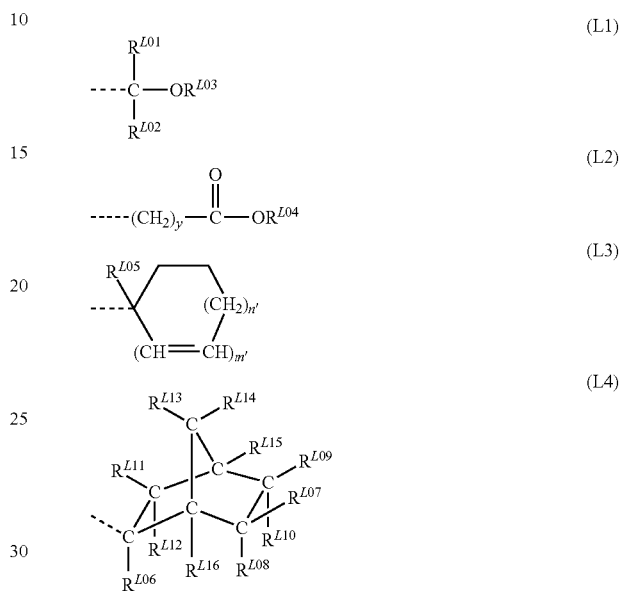

In formula (L1), $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyolohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a heteroatom such as oxygen, examples of which include unsubstituted straight, branched or cyclic alkyl groups and straight, branched or cyclic alkyl groups in which some hydrogen atoms are replaced by hydroxyl, alkoxy, oxo, amino, alkylamino or the like, or in which an oxygen atom intervenes between carbon atoms. Exemplary straight, branched or cyclic alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. Illustrative examples of the substituted alkyl groups are shown below.

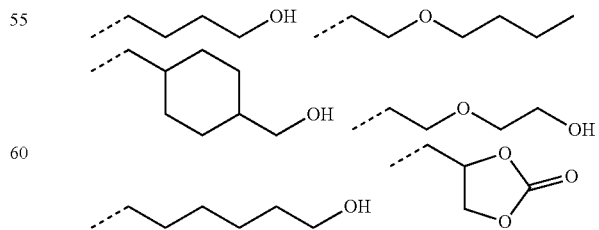

A pair of $R^{L01}$ and $R^{L02}$, $R^{L01}$ and $R^{L03}$, or $R^{L02}$ and $R^{L03}$ may bond together to form a ring with the carbon and oxygen atom to which they are attached. Each of $R^{L01}$, $R^{L02}$ and $R^{LO3}$ is a straight or branched alkylene group of 1 to 18 carbon atoms, preferably 1 to 10 carbon atoms when they form a ring.

In formula (L2), $R^{LO4}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)pro-pan-2-yl, 2-(adamantan-1-yl)propan-2-yl, 1-ethylcyclopen-tyl, 1-butylcyclopentyl, 1-ethyloyclohexyl, 1-butyloyclo-hexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

In formula (L3), $R^{LO5}$ is an optionally substituted, straight, branched or cyclic $C_1$-$C_8$ alkyl group or an optionally substituted $C_6$-$C_{20}$ aryl group. Examples of the optionally substituted alkyl group include straight, branched or cyclic alkyl groups such as methyl, ethyl, propyl, isopropyl, n-bu-tyl, sec-butyl, tert-butyl, tert-amyl, n-pentyl, n-hexyl, cyclo-pentyl and oyclohexyl, and substituted forms of the foregoing in which some hydrogen atoms are substituted by hydroxyl, alkoxy, carboxyl, alkoxycarbonyl, oxo, amino, alkylamino, cyano, mercapto, alkylthio, sulfo or the like. Examples of the optionally substituted aryl groups include phenyl, methylphenyl, naphthyl, anthryl, phenanthryl, and pyrenyl. Letter m' is equal to 0 or 1, n' is equal to 0, 1, 2 or 3, and 2m'+n' is equal to 2 or 3.

In formula (L4), $R^{LO6}$ is an optionally substituted, straight, branched or cyclic $C_1$-$C_8$ alkyl group or an optionally substituted $C_6$-$C_{20}$ aryl group. Examples of these groups are the same as exemplified for $R^{LO5}$. $R^{LO7}$ to $R^{L16}$ independently represent hydrogen or $C_1$-$C_{15}$ monovalent hydrocarbon groups. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyolopentyl, oyclohexyl, cyclopentylmethyl, cyclopentylethyl, cyclopen-tylbutyl, cyclohexylmethyl, cyclohexylethyl and cyclohex-ylbutyl, and substituted forms of the foregoing in which some hydrogen atoms are replaced by hydroxyl, alkoxy, carboxyl, alkoxycarbonyl, oxo, amino, alkylamino, cyano, mercapto, alkylthio, sulfo or other groups. Alternatively, two of $R^{LO7}$ to $R^{L16}$ may bond together to form a ring with the carbon atom to which they are attached (for example, a pair of $R^{LO7}$ and $R^{LO8}$, $R^{LO7}$ and $R^{LO9}$, $R^{LO7}$ and $R^{L10}$, $R^{LO8}$ and $R^{L10}$, $R^{LO9}$ and $R^{L10}$, $R^{L11}$ and $R^{L12}$, $R^{L13}$ and $R^{L14}$, or a similar pair form a ring). Each of $R^{LO7}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{LO7}$ to $R^{L16}$ which are attached to vicinal carbon atoms may bond together directly to form a double bond (for example, a pair of $R^{LO7}$ and $R^{LO9}$, $R^{LO9}$ and $R^{L15}$, $R^{L13}$ and $R^{L15}$, $R^{L14}$ and $R^{L15}$, or a similar pair).

Of the acid labile groups of formula (L1), the straight and branched ones are exemplified by the following groups.

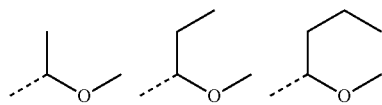

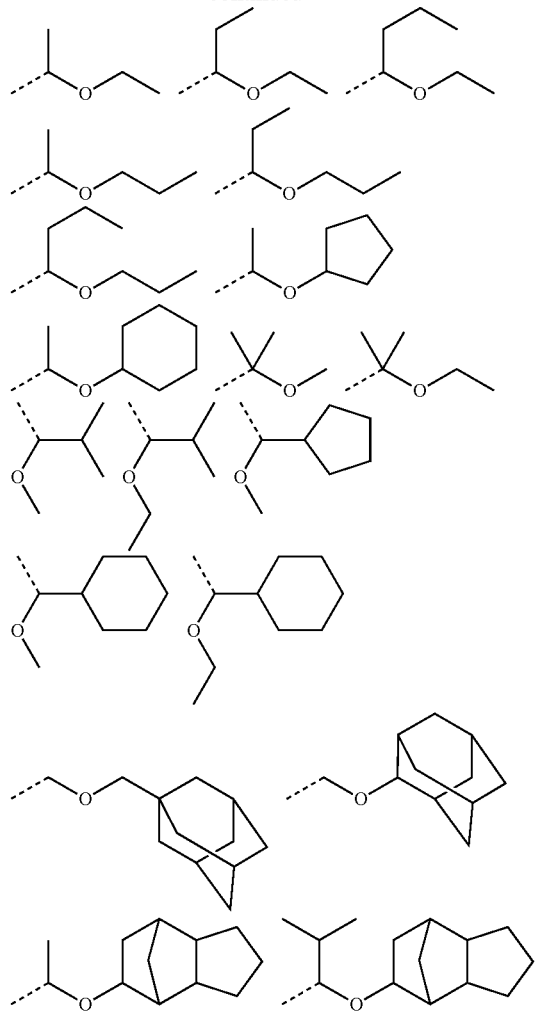

Of the acid labile groups of formula (L1), the cyclic ones are, for example, tetrahydrofuran-2-yl, 2-methyltetrahydro-furan-2-yl, tetrahydropyran-2-yl, and 2-methyltetrahydropy-ran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-di-ethylpropyloxycarbonyl, 1,1-diethylpropyloxycarbonylm-ethyl, 1-ethylcyclopentyloxycarbonyl, 1-ethylcyclopenty-loxyoarbonylmethyl, 1-ethyl-2-oyclopentenyloxycarbonyl, 1-ethyl-2-cyclopentenyloxycarbonylmethyl, 1-ethoxyethox-yearbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-pro-pylcyclopentyl, 1-isopropylcyclopentyl, 1-n-butyloyclopen-tyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulas (L4-1) to (L4-4) are preferred.

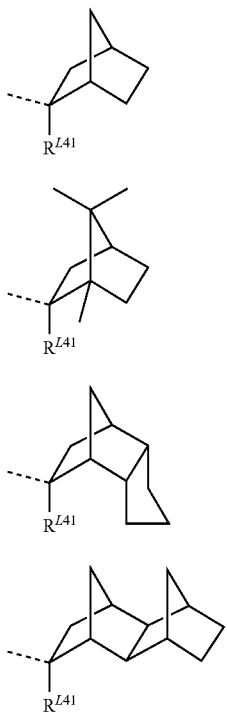

(L4-1)
(L4-2)
(L4-3)
(L4-4)

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

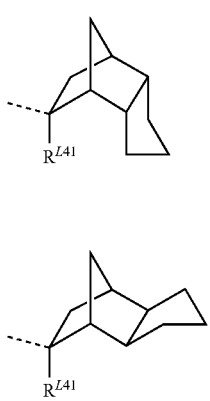

(L4-3-1)
(L4-3-2)

Similarly, the general formula (L4-4) represents one or a mixture of two or more selected from groups having the following general formulas (L4-4-1) to (L4-4-4).

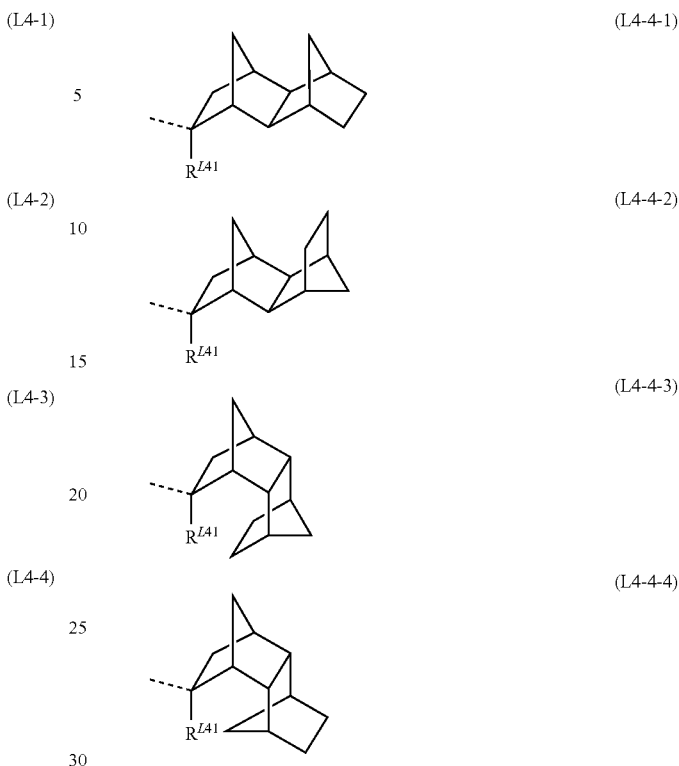

(L4-4-1)
(L4-4-2)
(L4-4-3)
(L4-4-4)

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyolo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

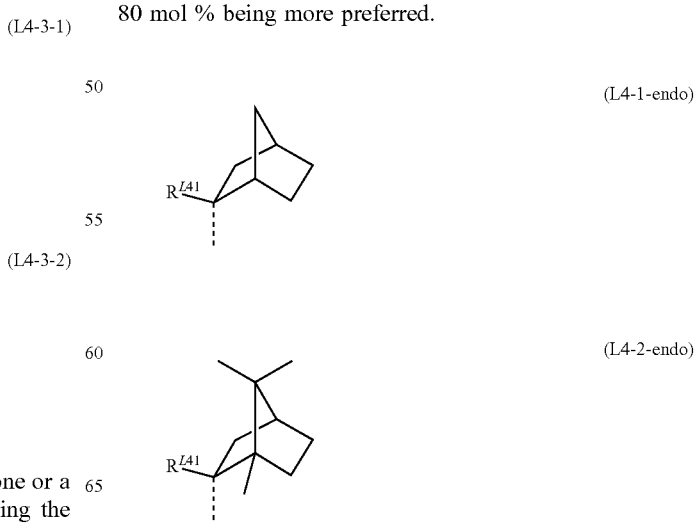

(L4-1-endo)
(L4-2-endo)

27
-continued (L4-3-endo)

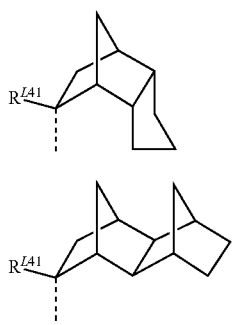

(L4-4-endo)

Illustrative examples of the acid labile group of formula (L4) are given below.

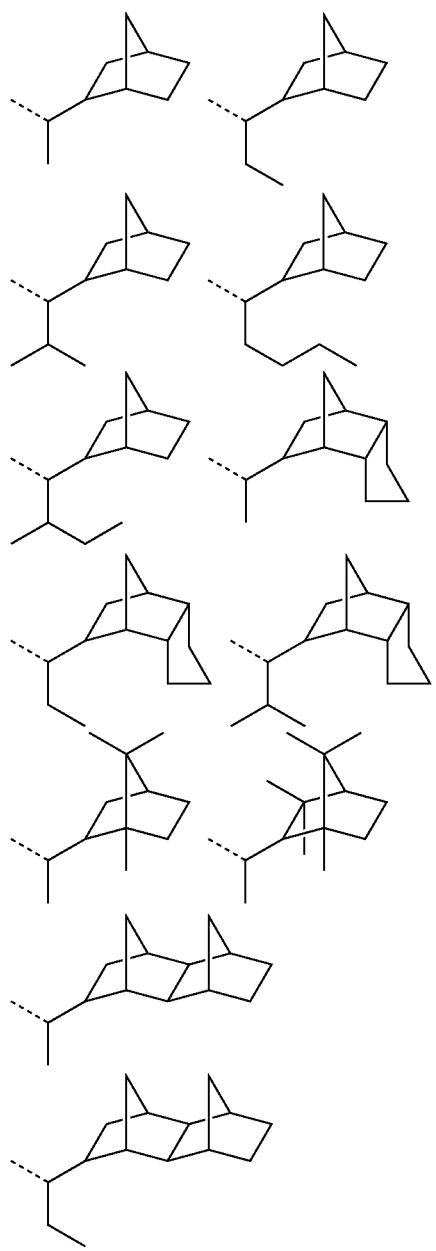

28
-continued

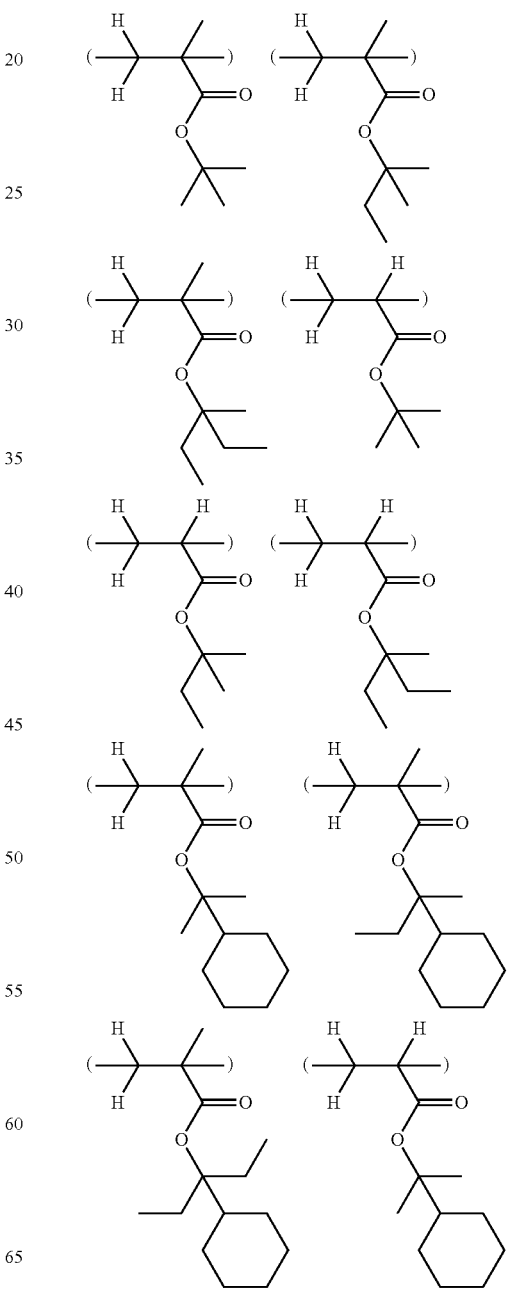

Examples of the tertiary $C_4$-$C_{20}$ alkyl groups, trialkylsilyl groups in which each alkyl moiety has 1 to 6 carbon atoms, and $C_4$-$C_{20}$ oxoalkyl groups are as exemplified for $R^{L04}$.

Illustrative examples of the recurring units of formula (2) are given below, but not limited thereto.

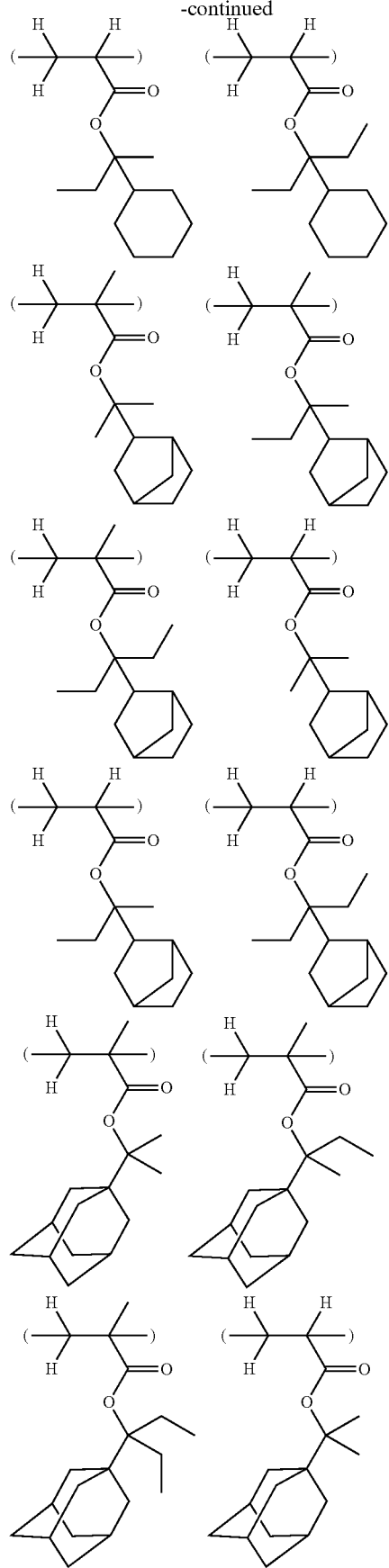
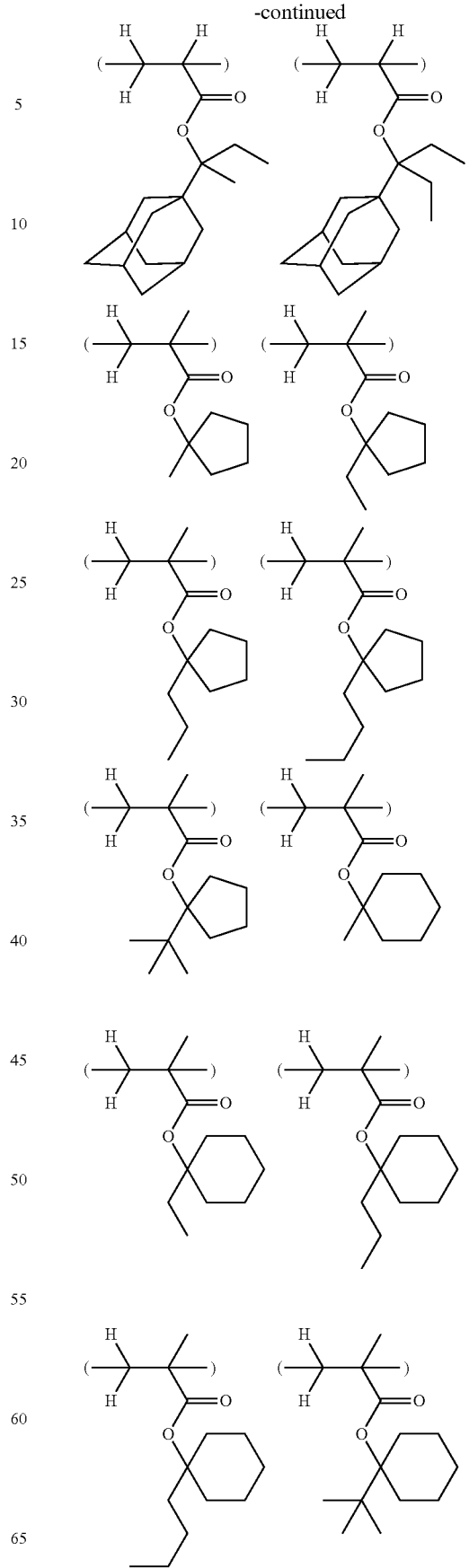

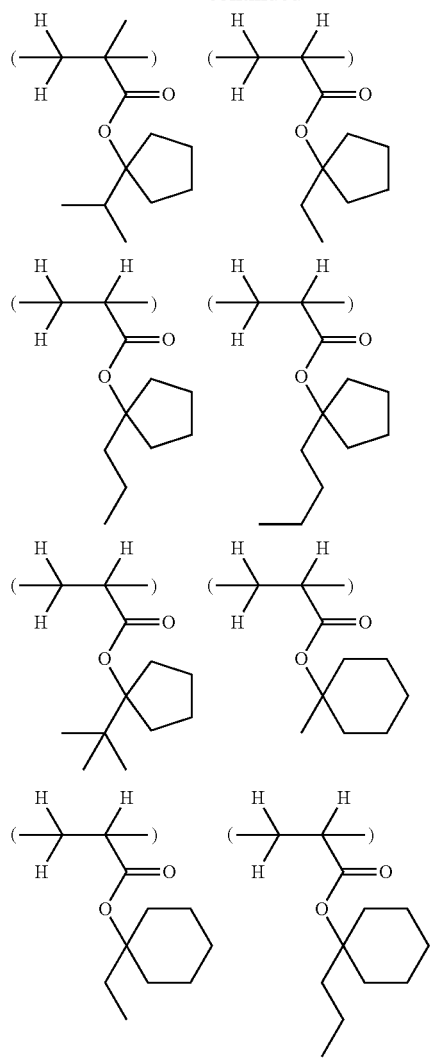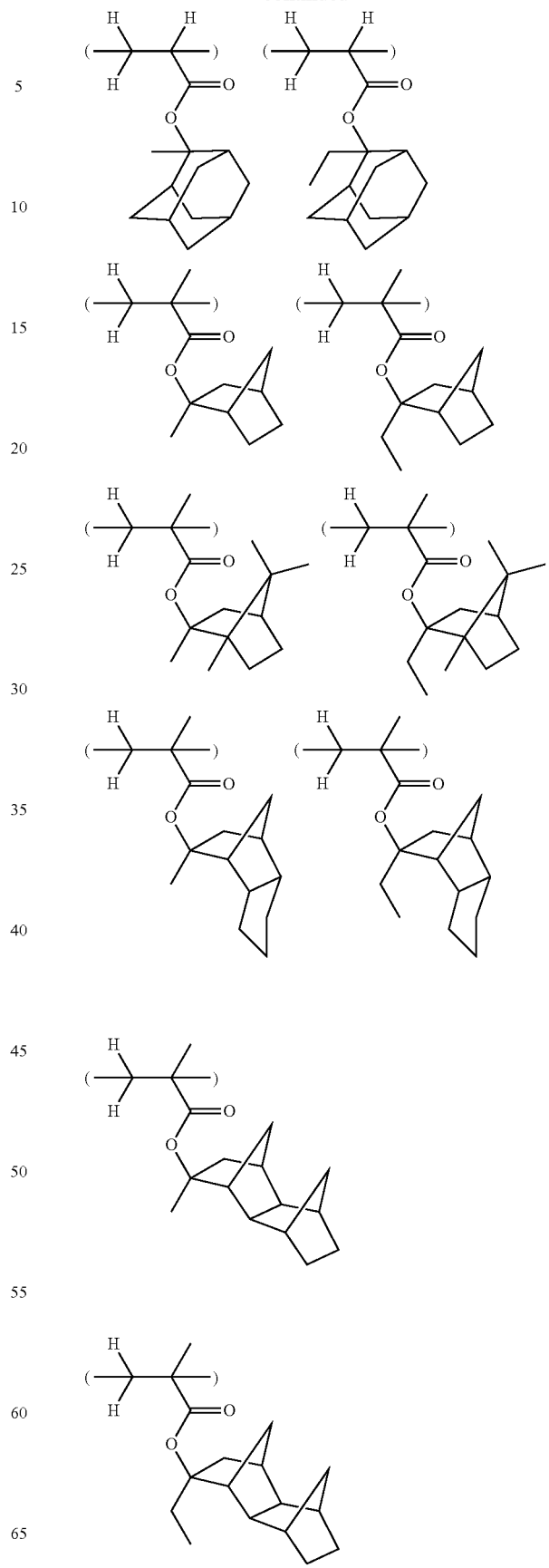

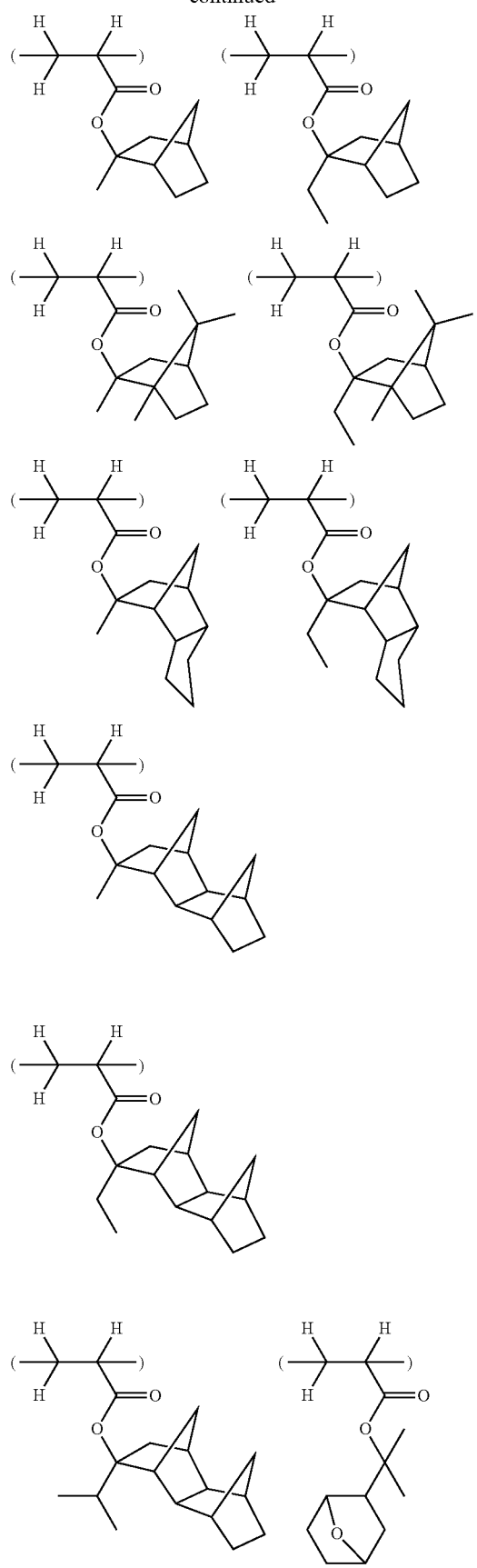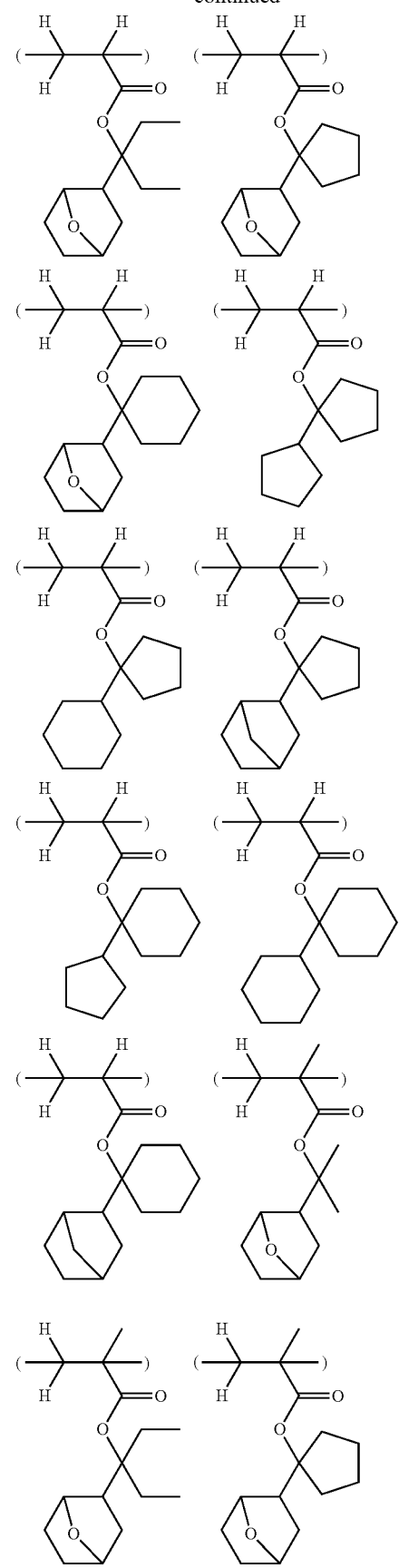

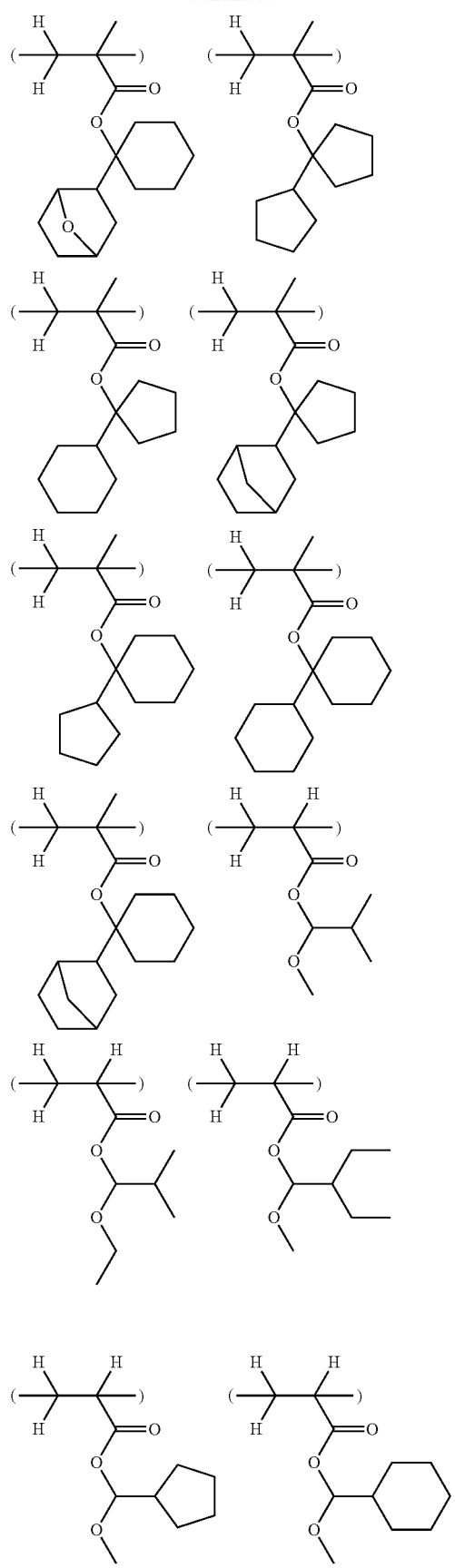
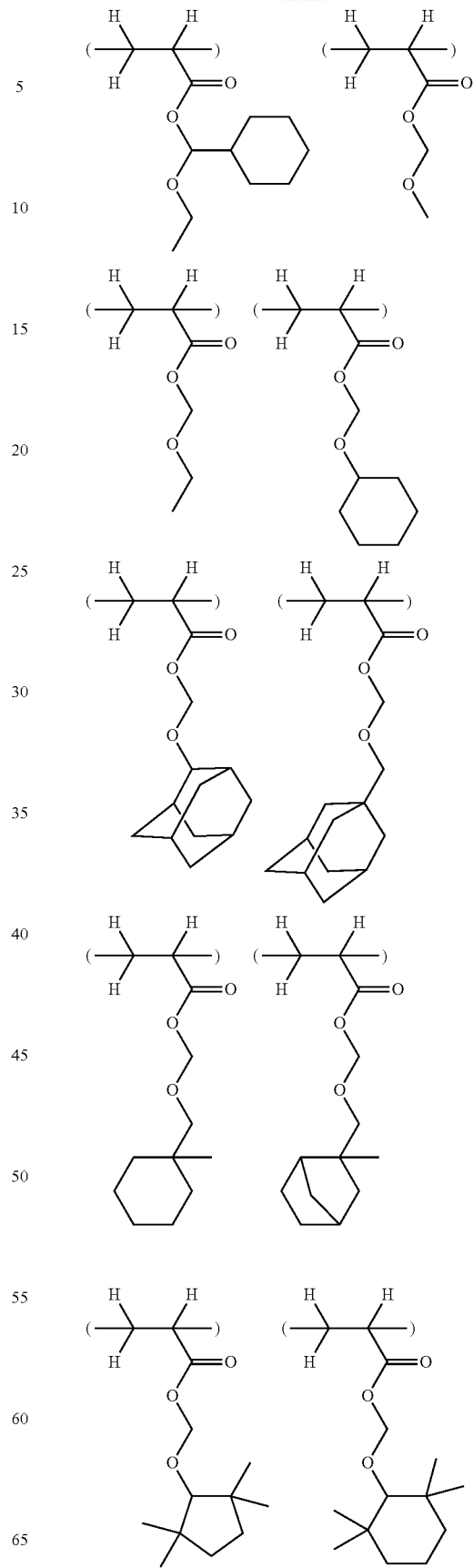

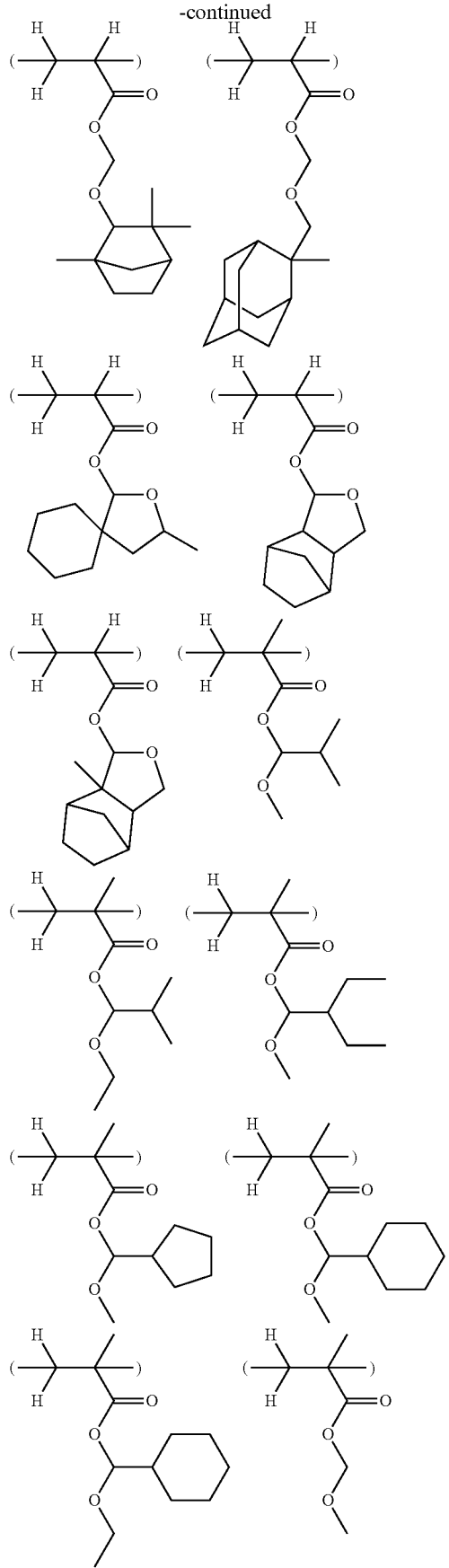
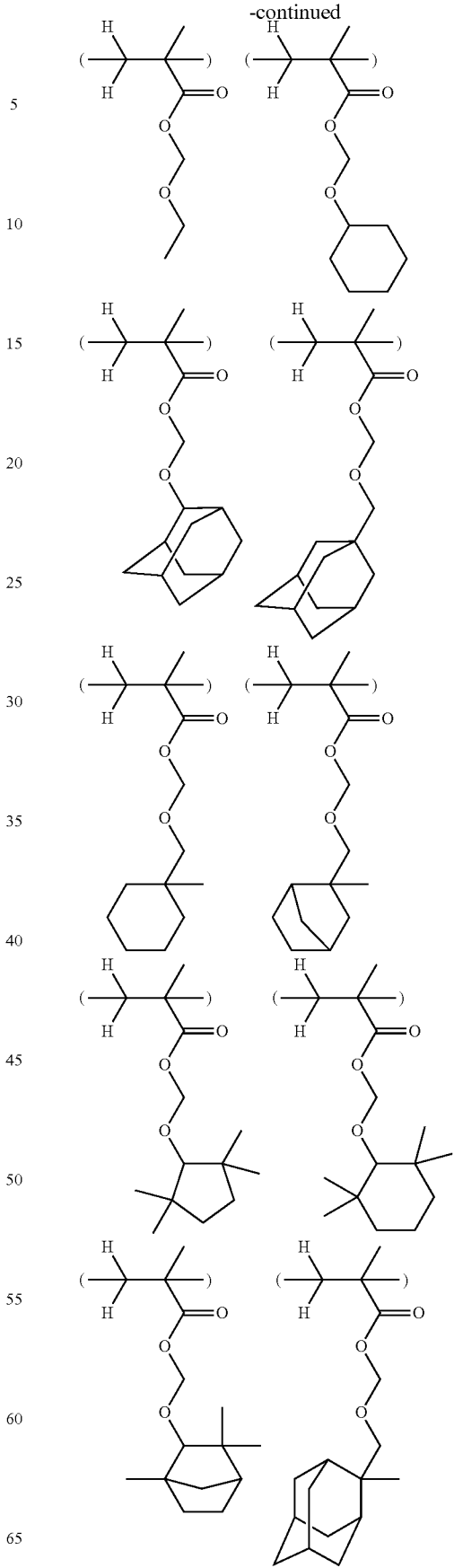

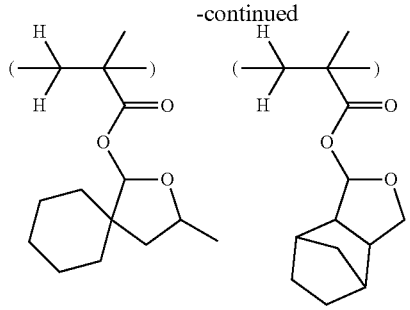

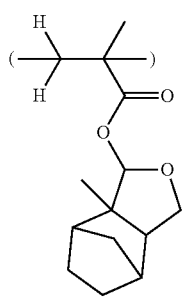

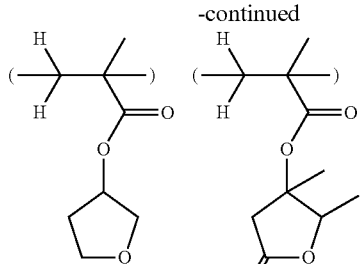

The above examples correspond to those units of formula (2) wherein $Z^a$ is a single bond. Where $Z^a$ is other than a single bond, a combination with a similar acid labile group is possible. Thus examples of the recurring units of formula (2) wherein $Z^a$ is other than a single bond are as illustrated above.

In formula (3), YL is hydrogen, or YL is a polar group having one or more structures selected from the group consisting of hydroxyl, cyano, carbonyl, carboxyl, ether bond, ester bond, sulfonate (sulfonic acid ester) bond, carbonate bond, lactone ring, sultone ring, and carboxylic anhydride.

Illustrative examples of the recurring units of formula (3) are given below, but not limited thereto.

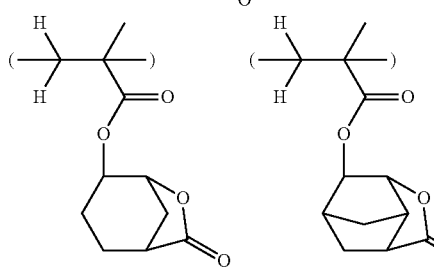

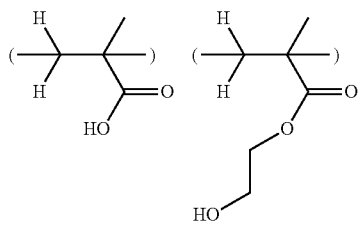

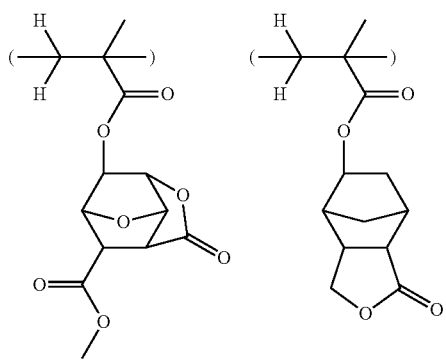

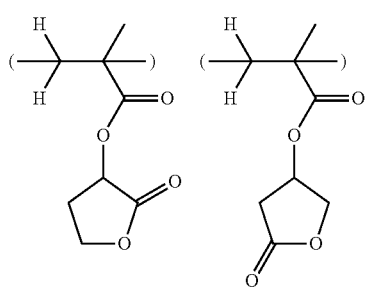

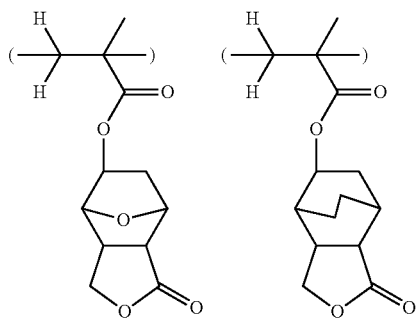

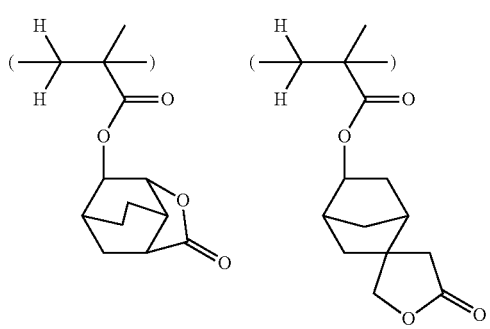

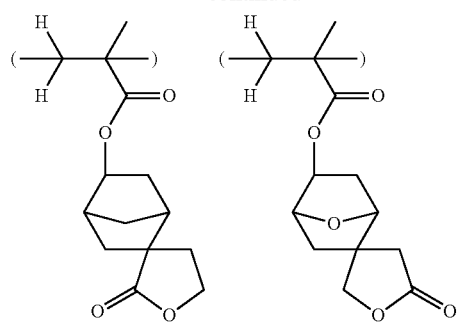
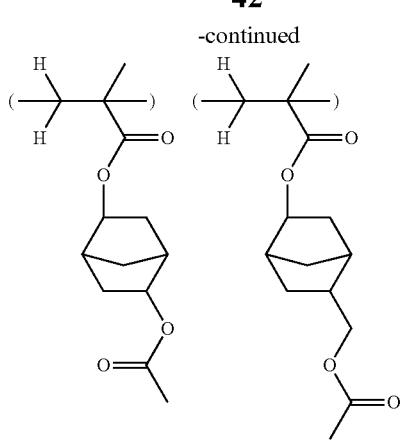
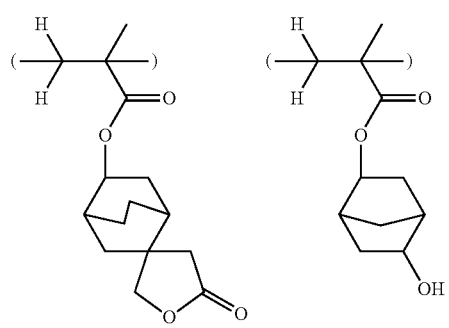
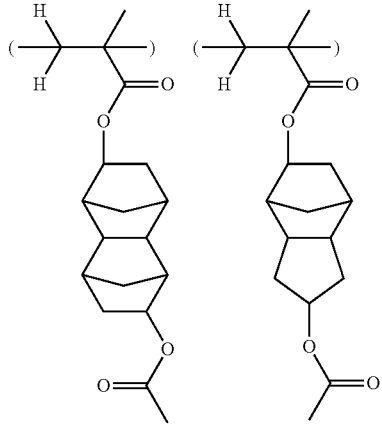
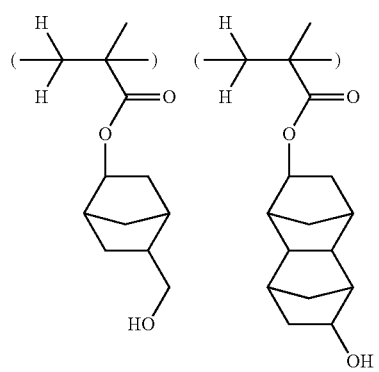
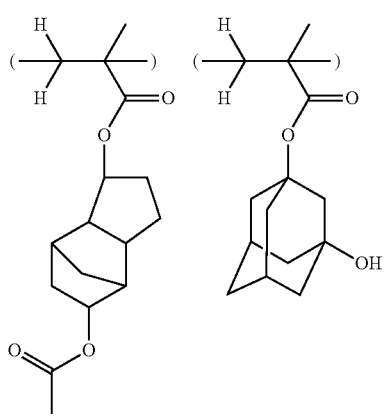
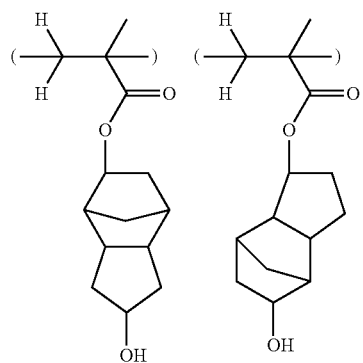
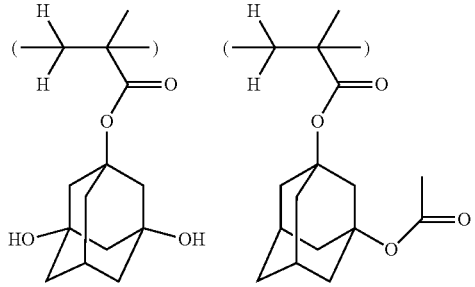

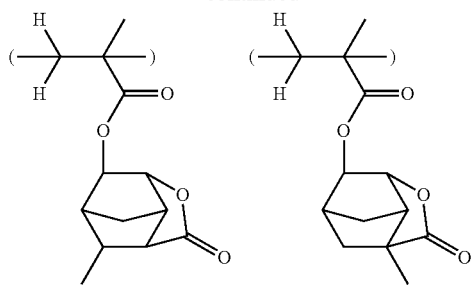
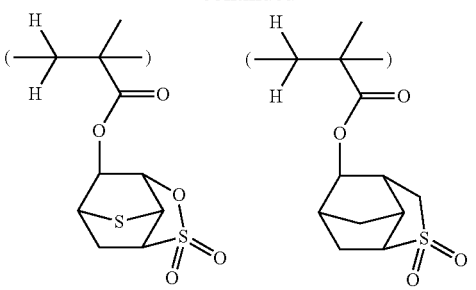
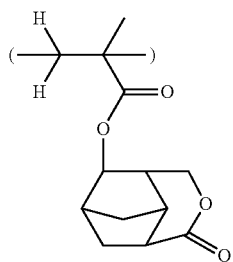
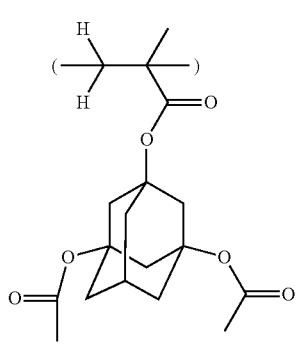
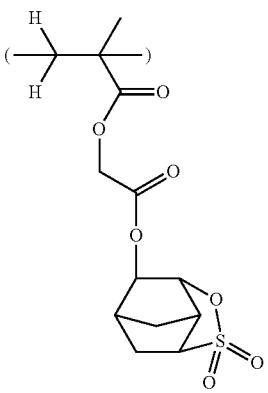
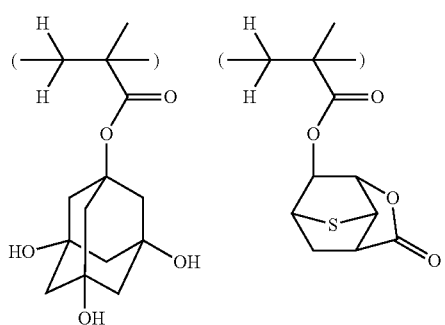
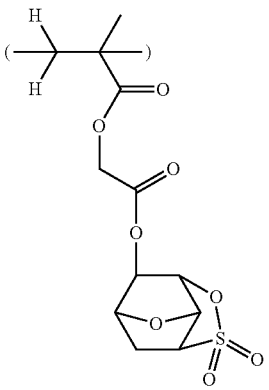
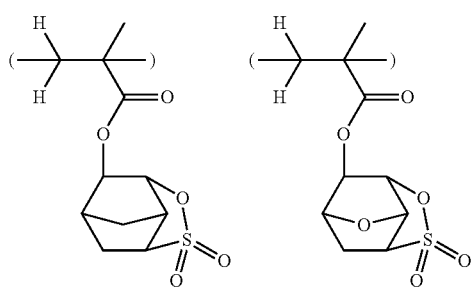
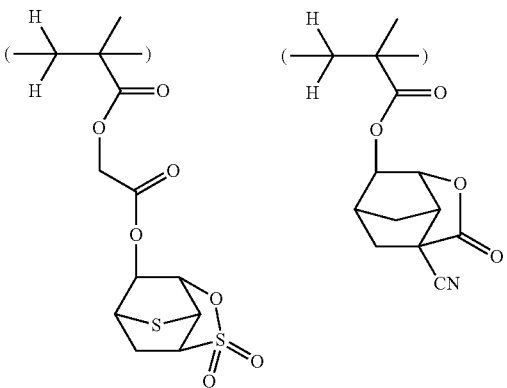

-continued
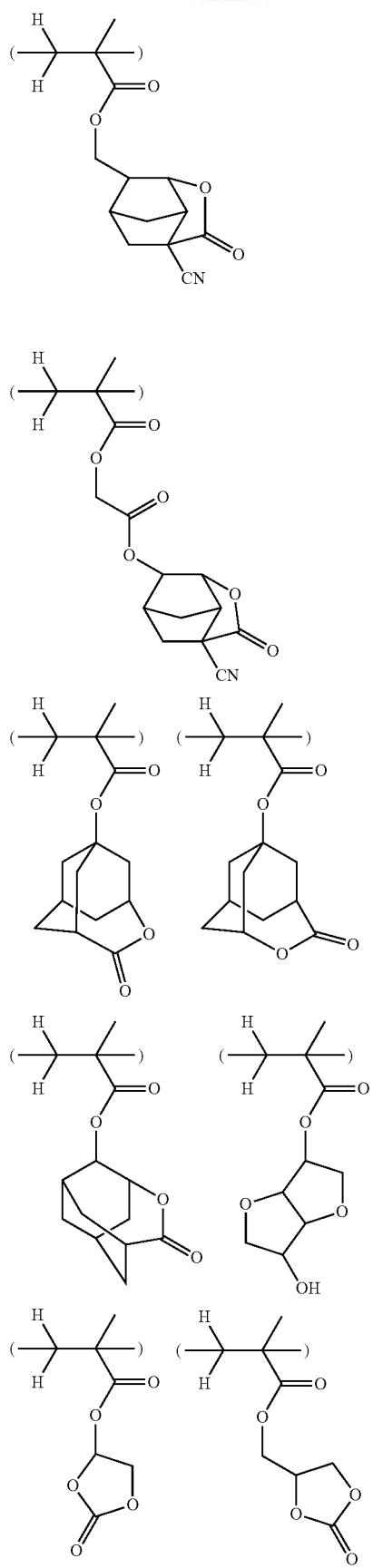
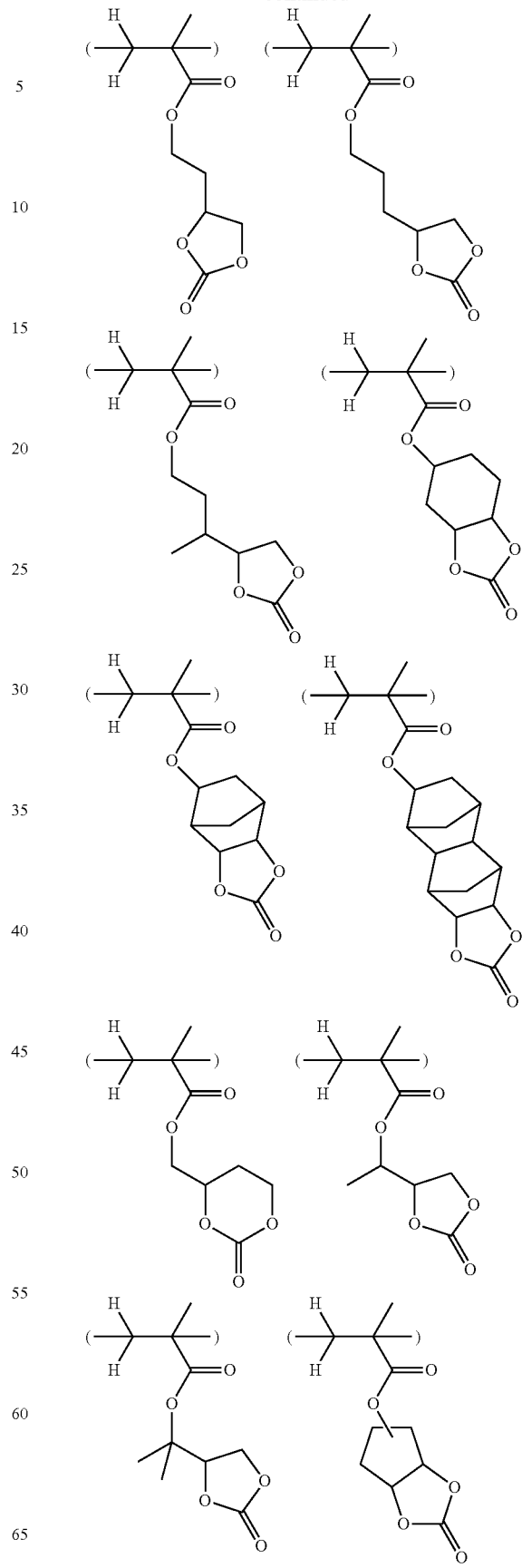

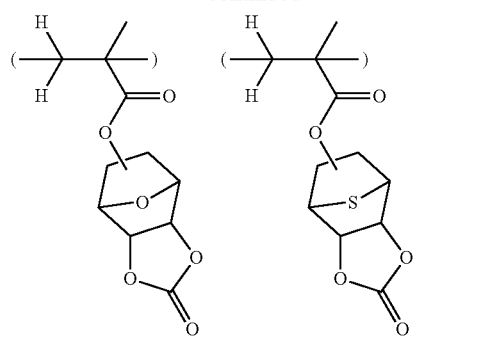
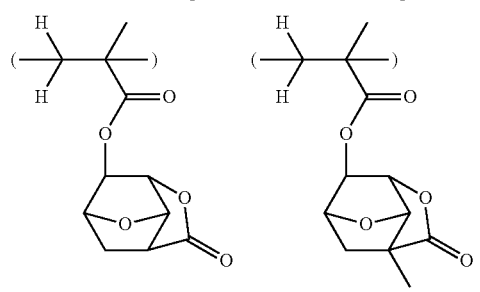
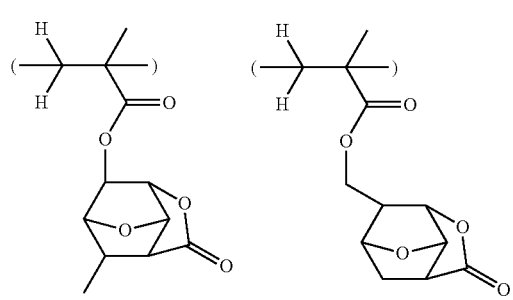
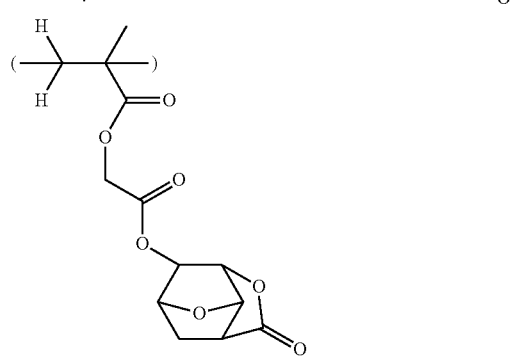
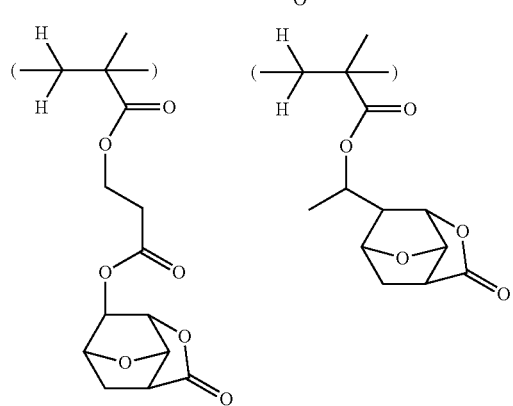
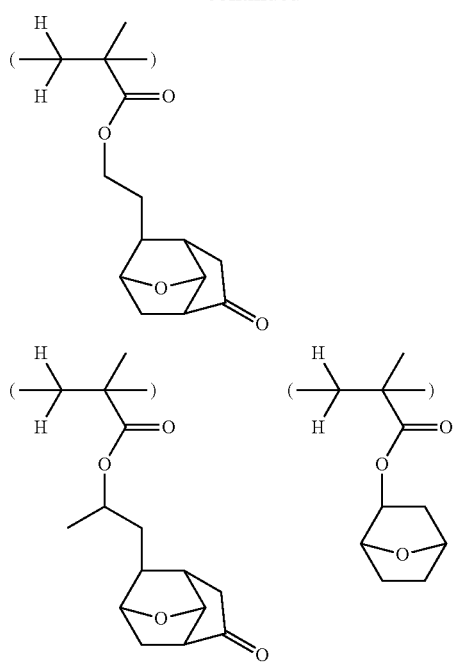
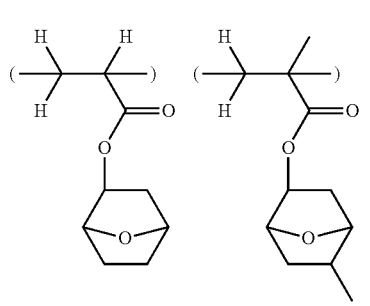
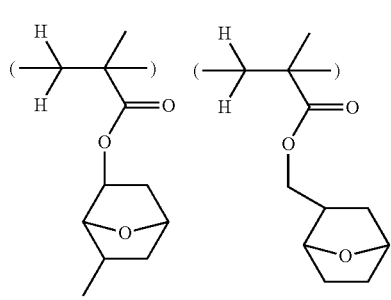
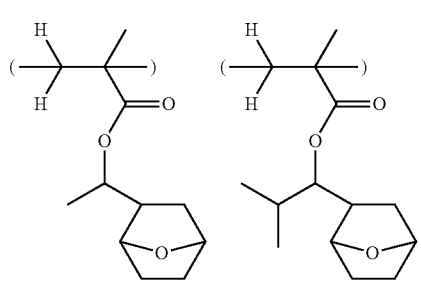

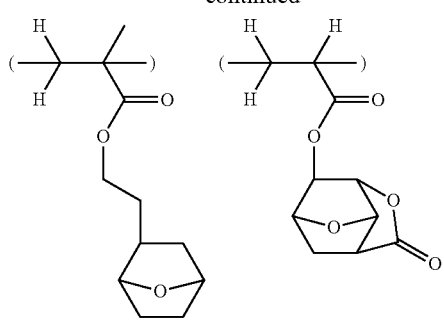
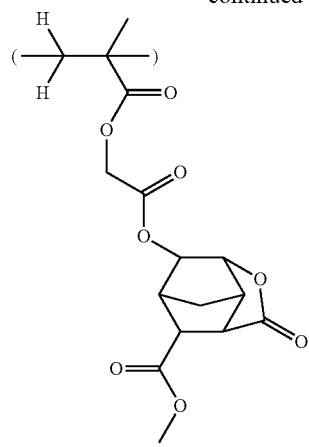
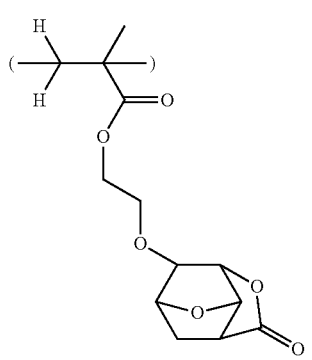
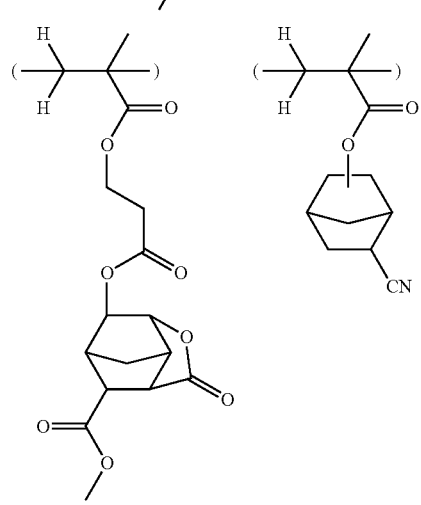
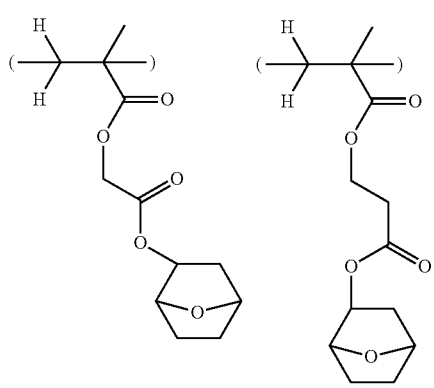
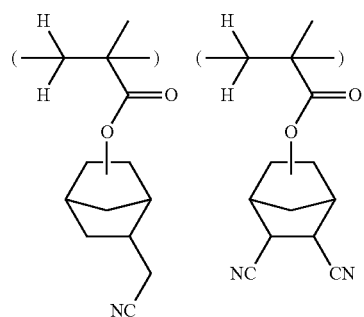
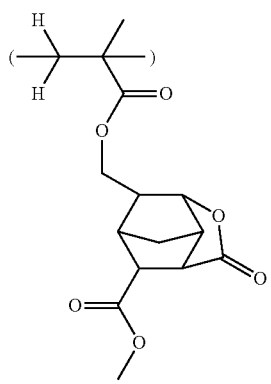
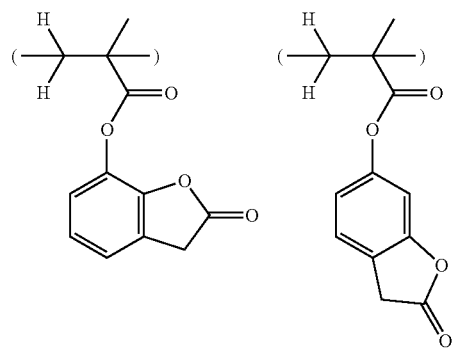

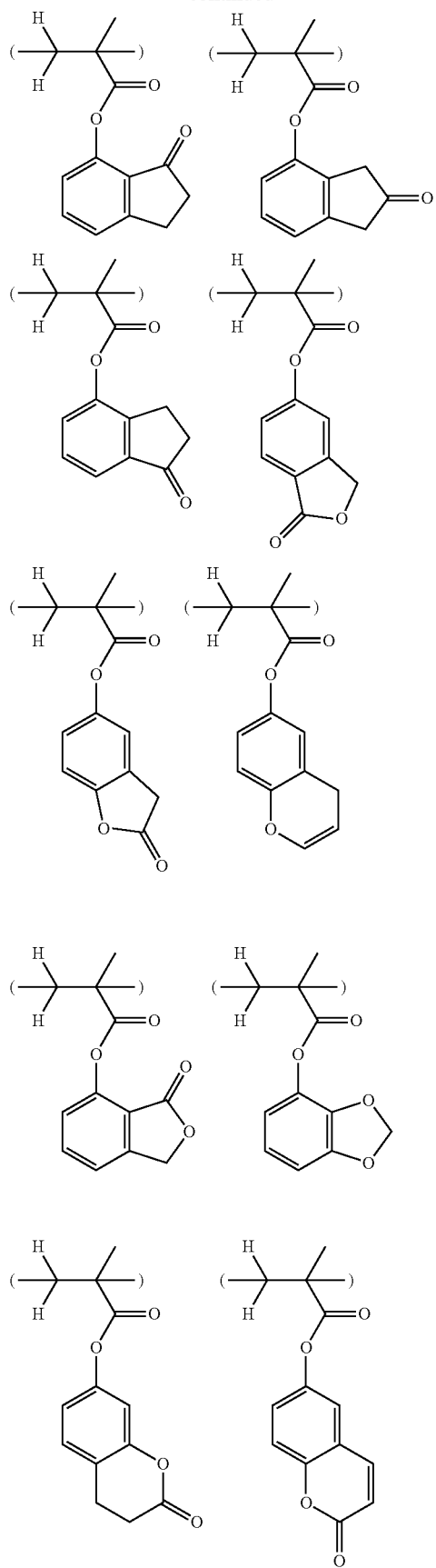
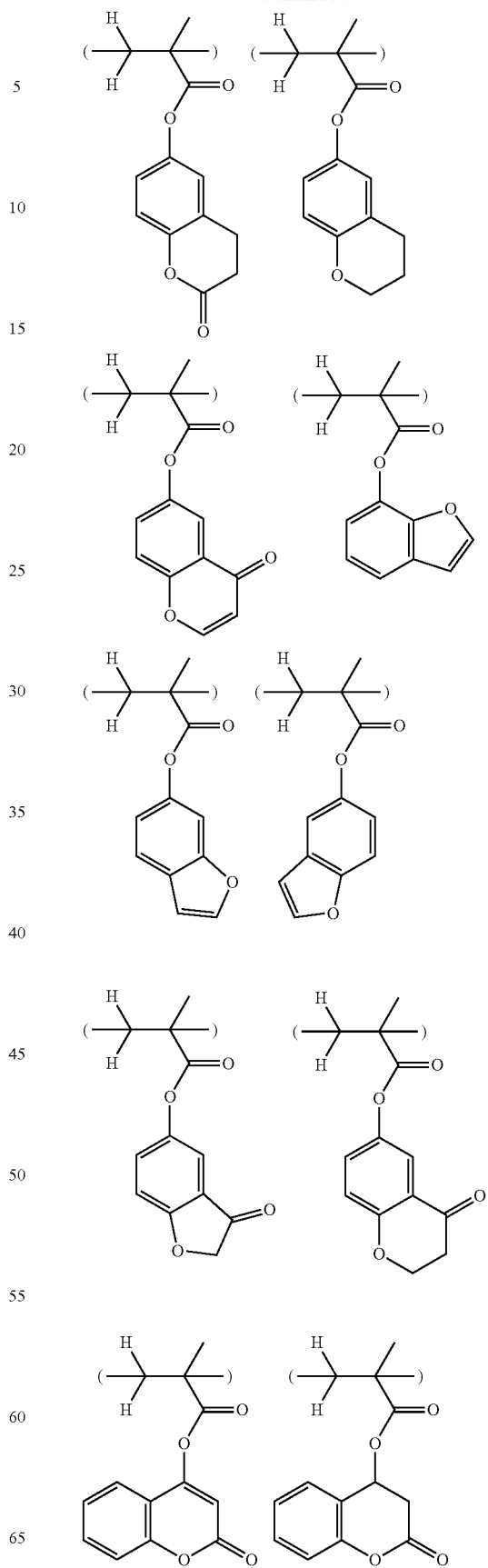

-continued
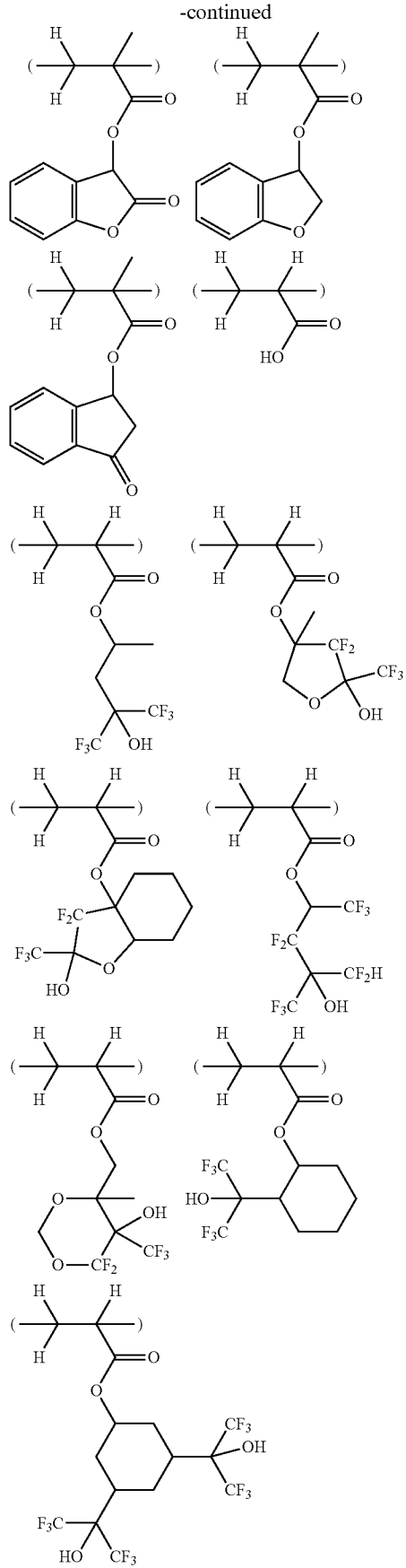
-continued
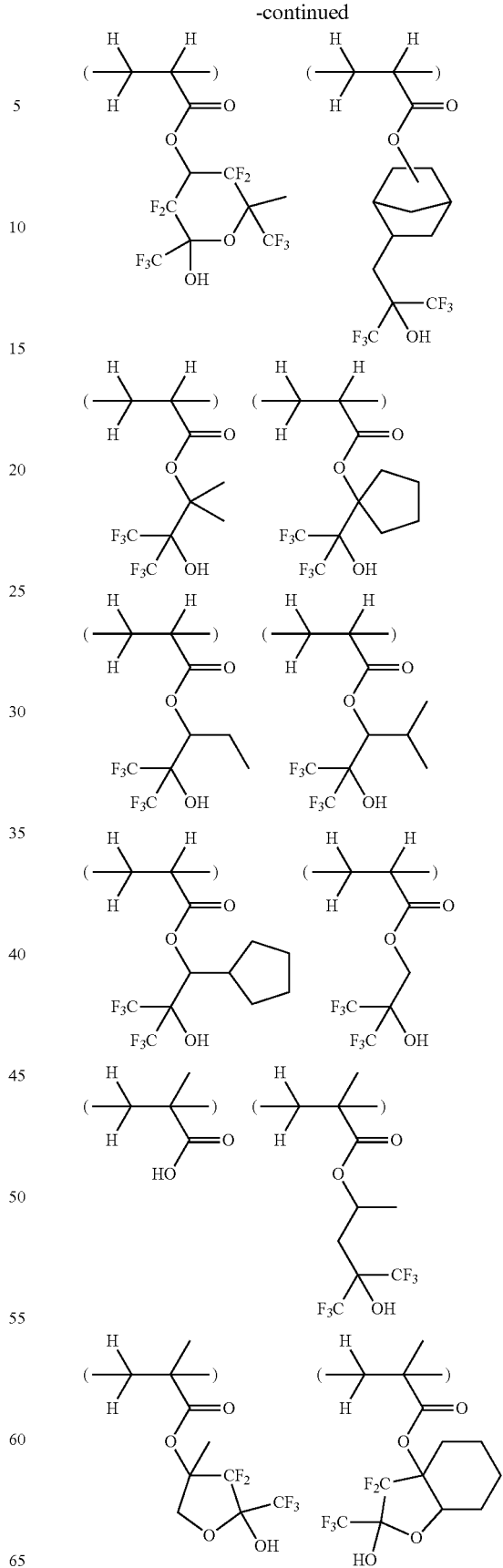

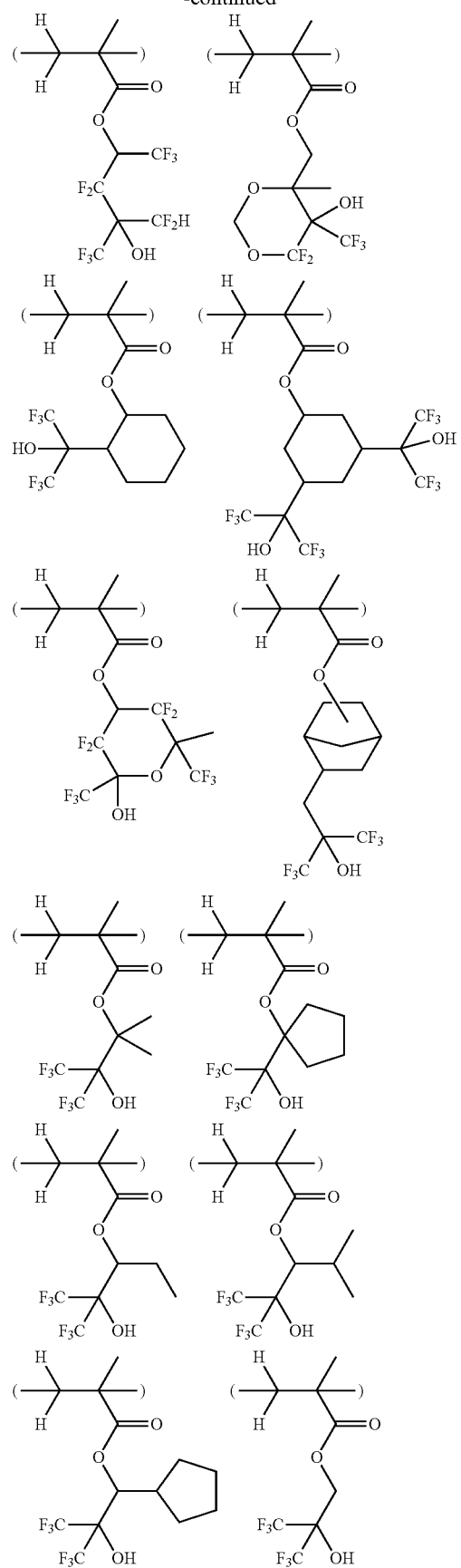
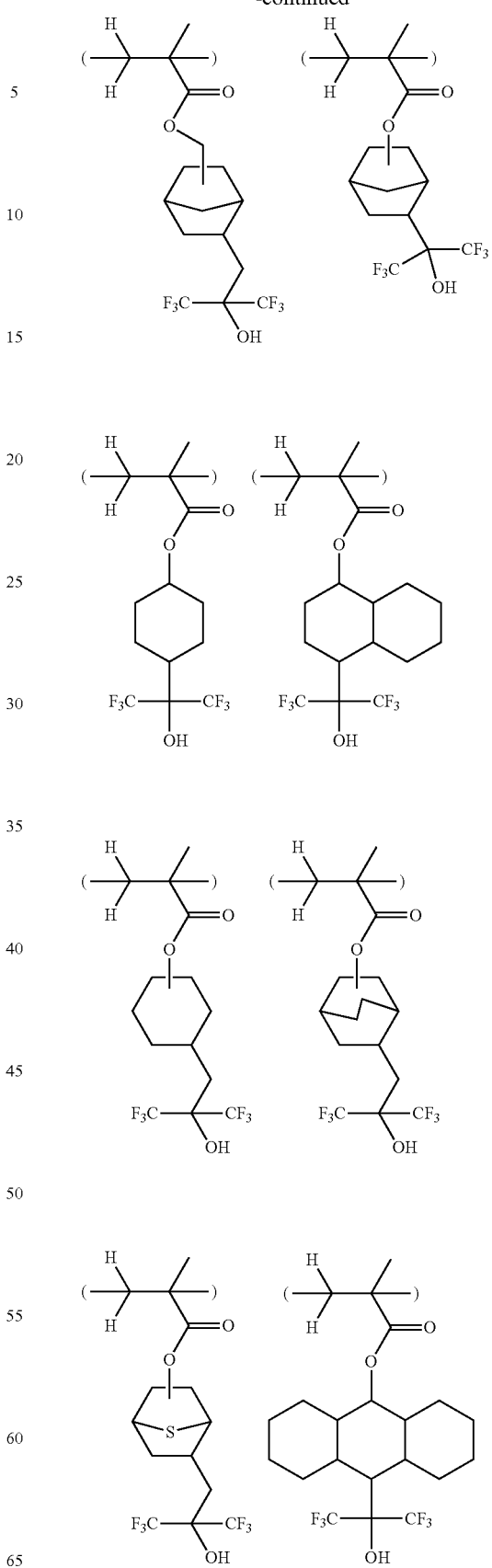

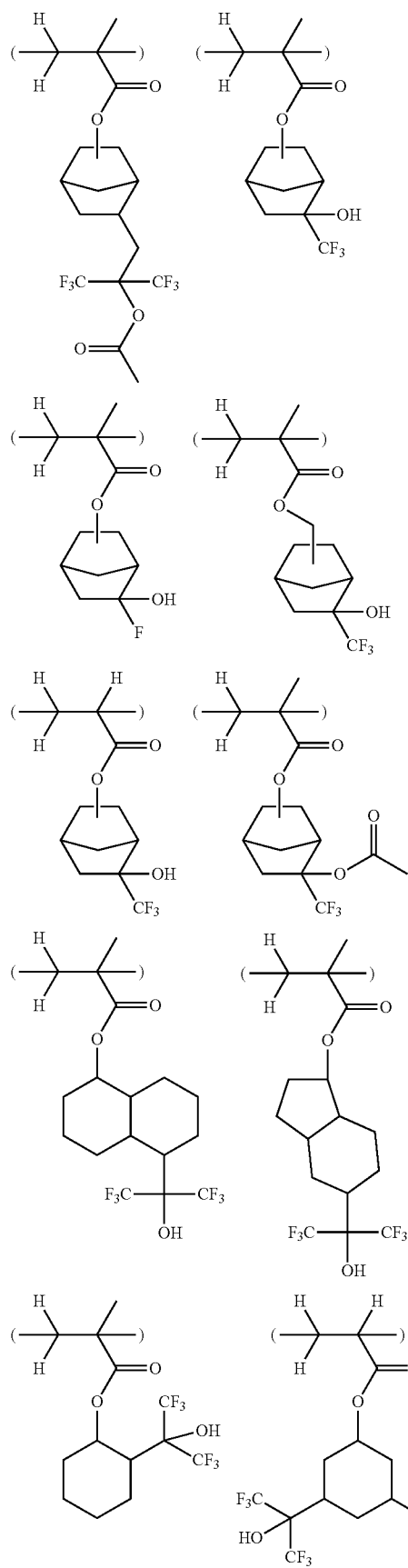
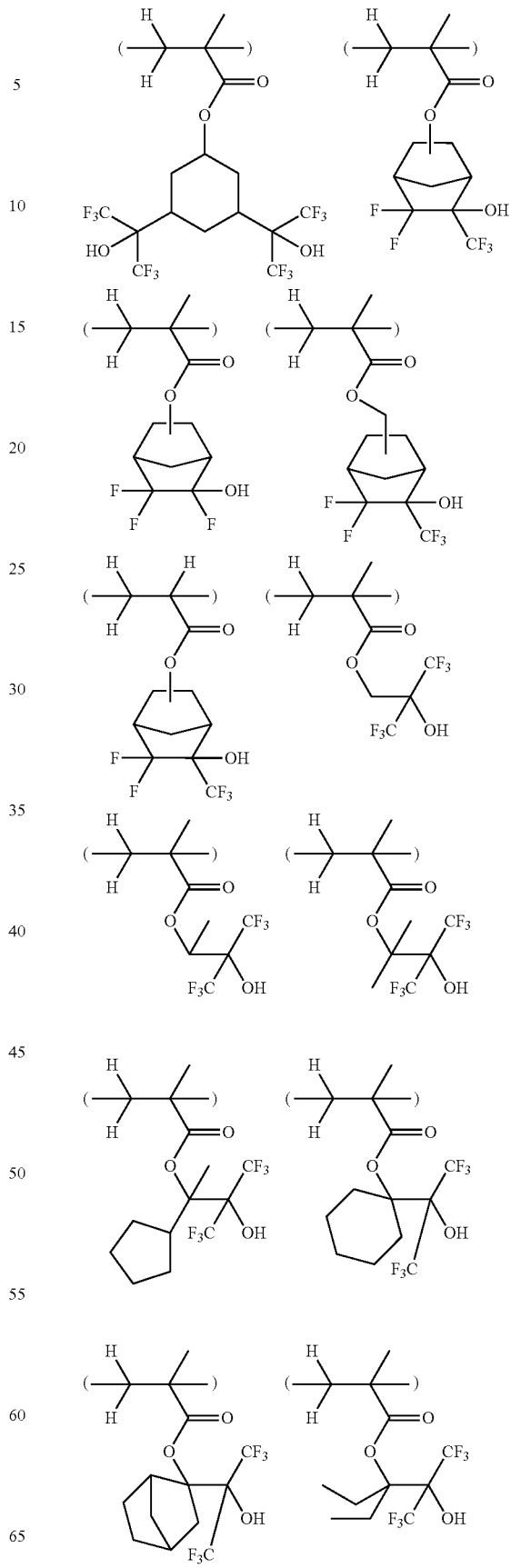

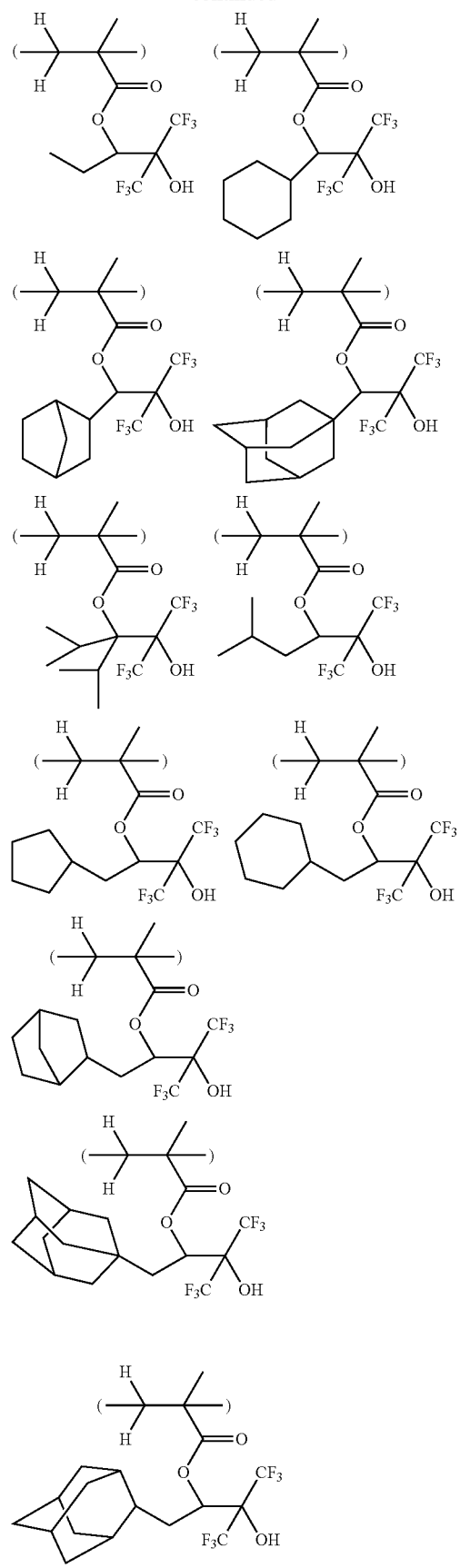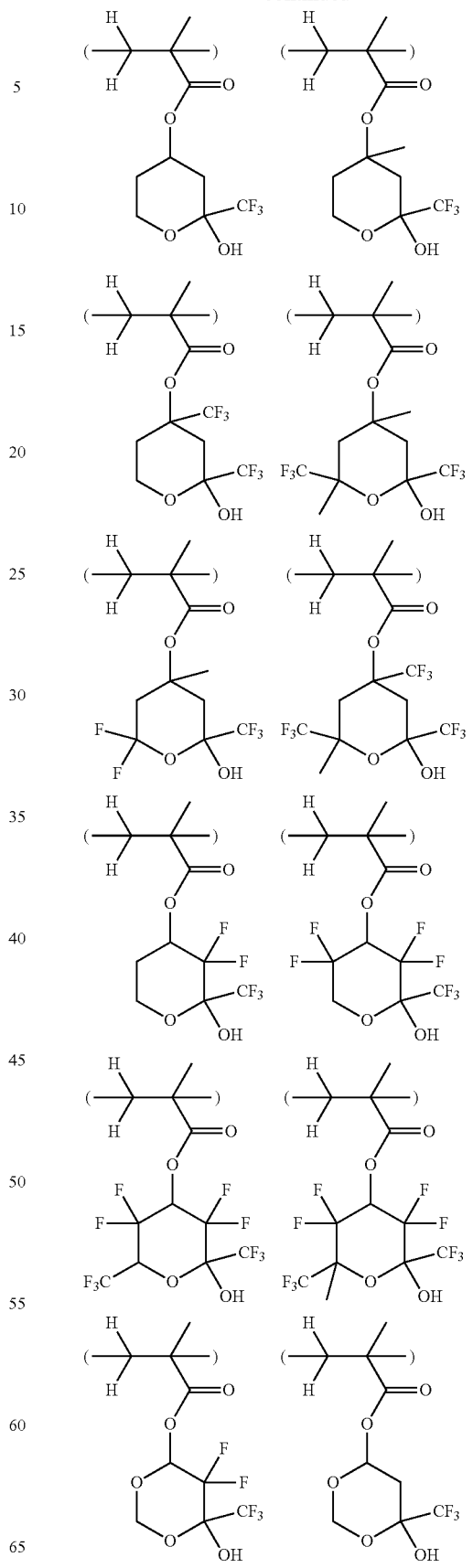

-continued
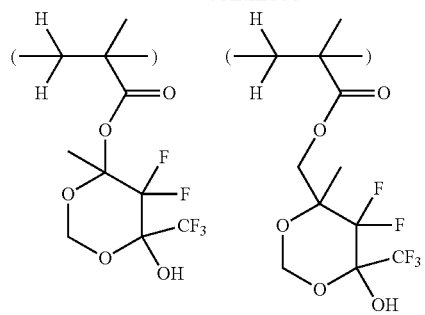
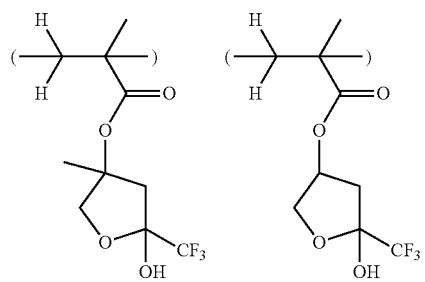
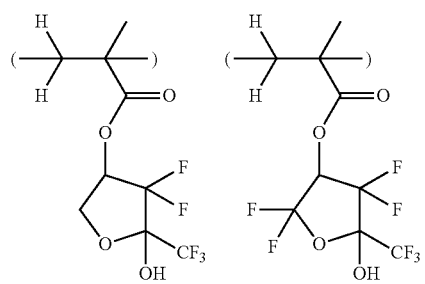
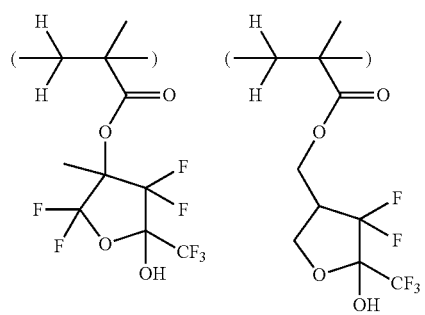
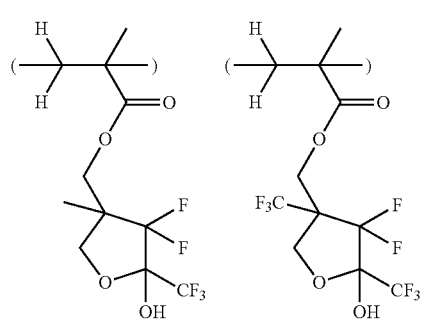
-continued
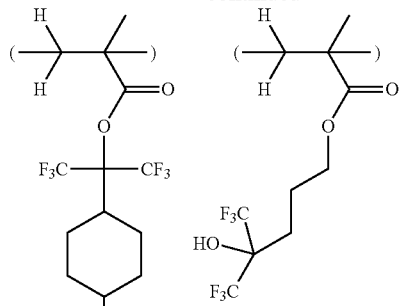
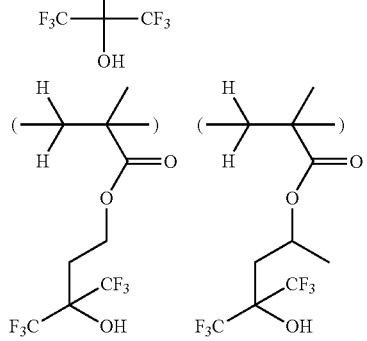
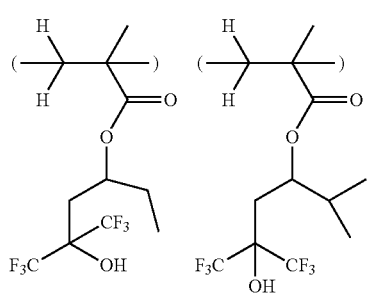
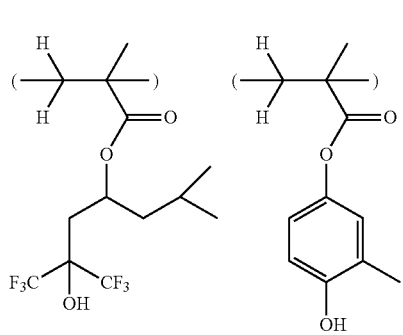
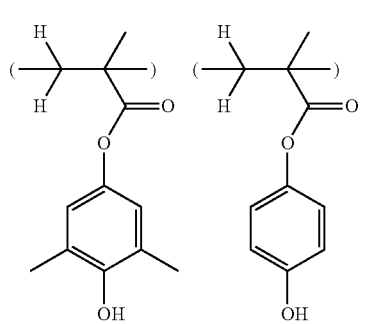

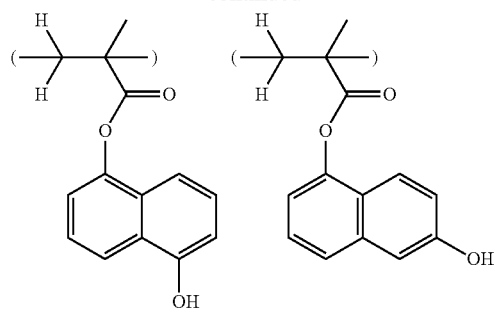
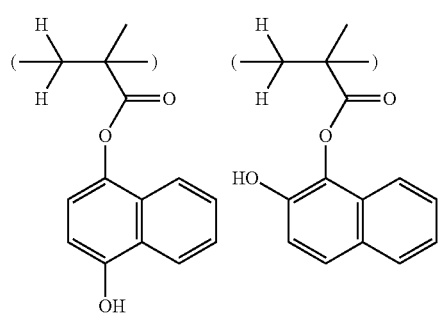
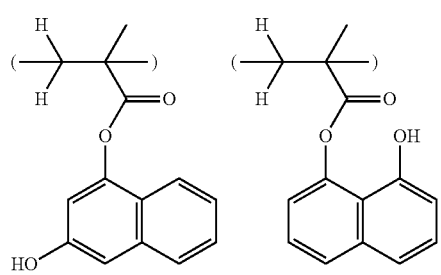
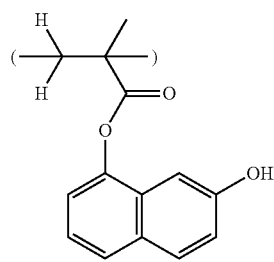
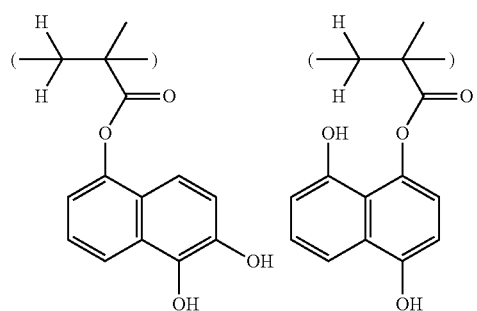
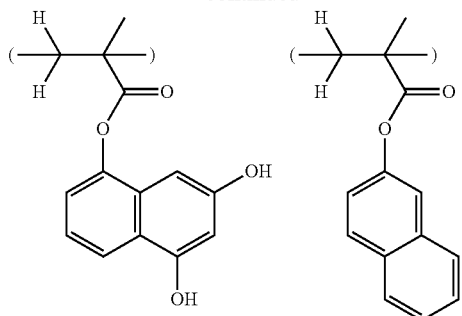
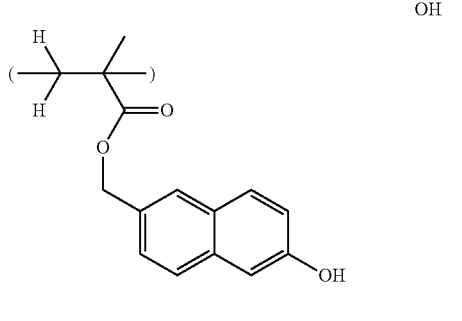
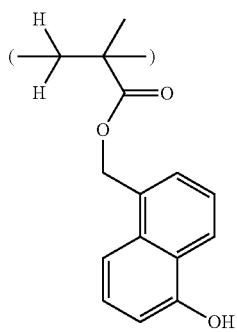
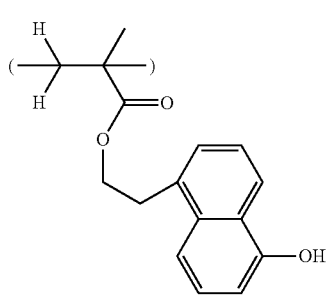
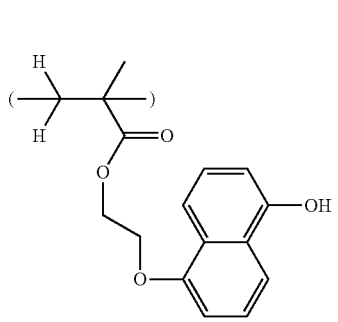

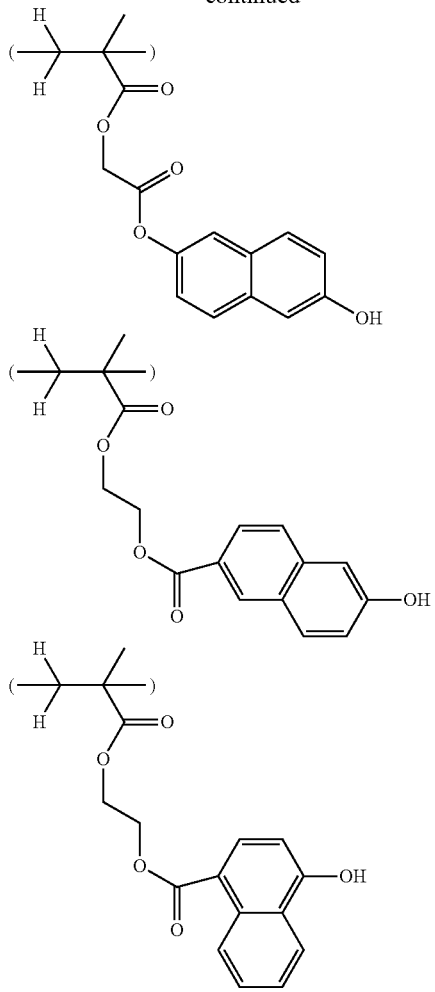

Where the recurring units of formula (3) are incorporated, units having lactone ring as the polar group are most preferably used.

While the polymer is characterized by comprising recurring units having formulae (2) and (3), optionally recurring units having the general formula (d1) or (d2) may also be incorporated.

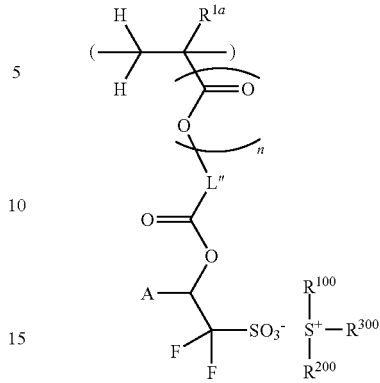

Herein $R^{1a}$, $R^{100}$, $R^{200}$, and $R^{300}$ are as defined above. L' is a $C_2$-$C_5$ alkylene group. $R^Y$ is a straight $C_1$-$C_{20}$ or branched or cyclic $C_3$-$C_{20}$ monovalent hydrocarbon group which may be substituted with or separated by a heteroatom. A is hydrogen or trifluoromethyl. L" is a single bond or a straight $C_1$-$C_{20}$ or branched or cyclic $C_3$-$C_{20}$ divalent hydrocarbon group which may be substituted with or separated by a heteroatom, m is 0 or 1, n is 0 or 1, with the proviso that n is 0 when L" is a single bond.

In formulae (d1) and (d2), $R^{1a}$ is as defined and exemplified above. L' is a $C_2$-$C_5$ alkylene group, preferably ethylene, propylene or butylene. A is hydrogen or trifluoromethyl, preferably trifluoromethyl. $R^Y$ is a straight $C_1$-$C_{20}$ or branched or cyclic $C_3$-$C_{20}$ monovalent hydrocarbon group, examples of which are as described above for $R^{11}$, $R^{22}$, $R^{33}$, $R^{44}$, $R^{55}$ and $R^{01}$ in formula (1). L" is a single bond or a straight $C_1$-$C_{20}$ or branched or cyclic $C_3$-$C_{20}$ divalent hydrocarbon group, examples of which are as descried above. $R^{100}$, $R^{200}$ and $R^{300}$ are as descried above.

Illustrative structures of the anion moiety in formula (d1) include those described in JP-A 2010-113209 and JP-A 2007-145797. Illustrative structures of the anion moiety in formula (d2) wherein A is hydrogen include those described in JP-A 2010-116550. Illustrative structures of the anion moiety in formula (d2) wherein A is trifluoromethyl include those described in JP-A 2010-077404.

While the polymer is characterized by comprising recurring units having formulae (2) and (3), and optionally recurring units having formula (d1) or (d2), other recurring units, typically recurring units of the structure having a hydroxyl group protected with an acid labile group may be further copolymerized. The recurring units of the structure having a hydroxyl group protected with an acid labile group are not particularly limited as long as the unit has one or more structures each having protected hydroxyl wherein the protective group is decomposed under the action of acid to generate a hydroxyl group. Of these, recurring units of the structure having the general formula (e1) are preferred.

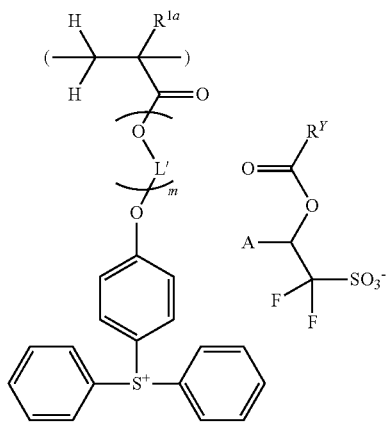

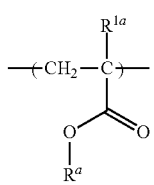

In formula (e1), $R^{1a}$ is as defined above; $R^a$ is a straight $C_1$-$C_{20}$ or branched or cyclic $C_3$-$C_{20}$ monovalent hydrocarbon group which may be substituted with or separated by a heteroatom, with the proviso that the monovalent hydrocarbon group of $R^a$ has 1, 2, 3 or 4 substituent groups having formula (e2).

$$-OR^b \quad (e2)$$

Herein $R^b$ is an acid labile group.

Illustrative examples of the recurring units having formula (e1) are given below, but not limited thereto.

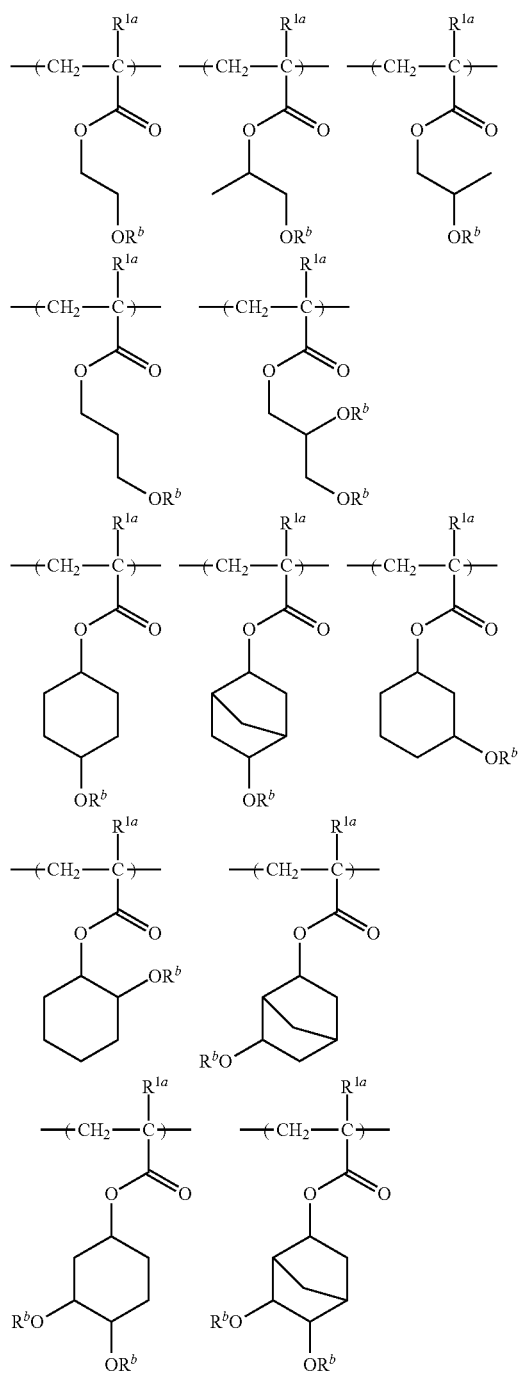

-continued

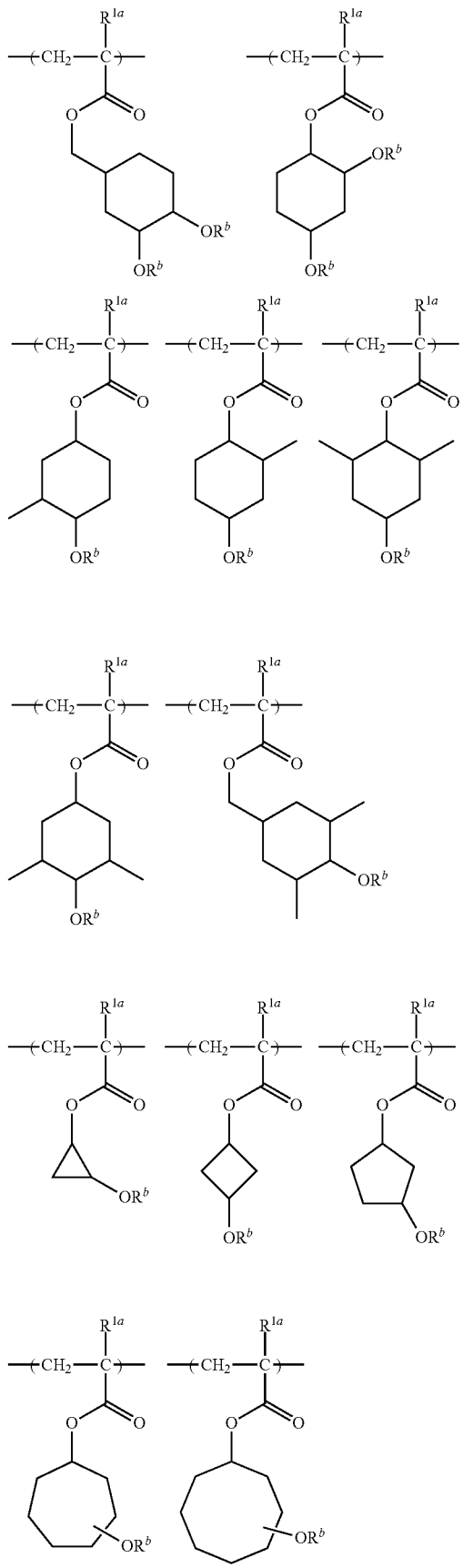

69
-continued
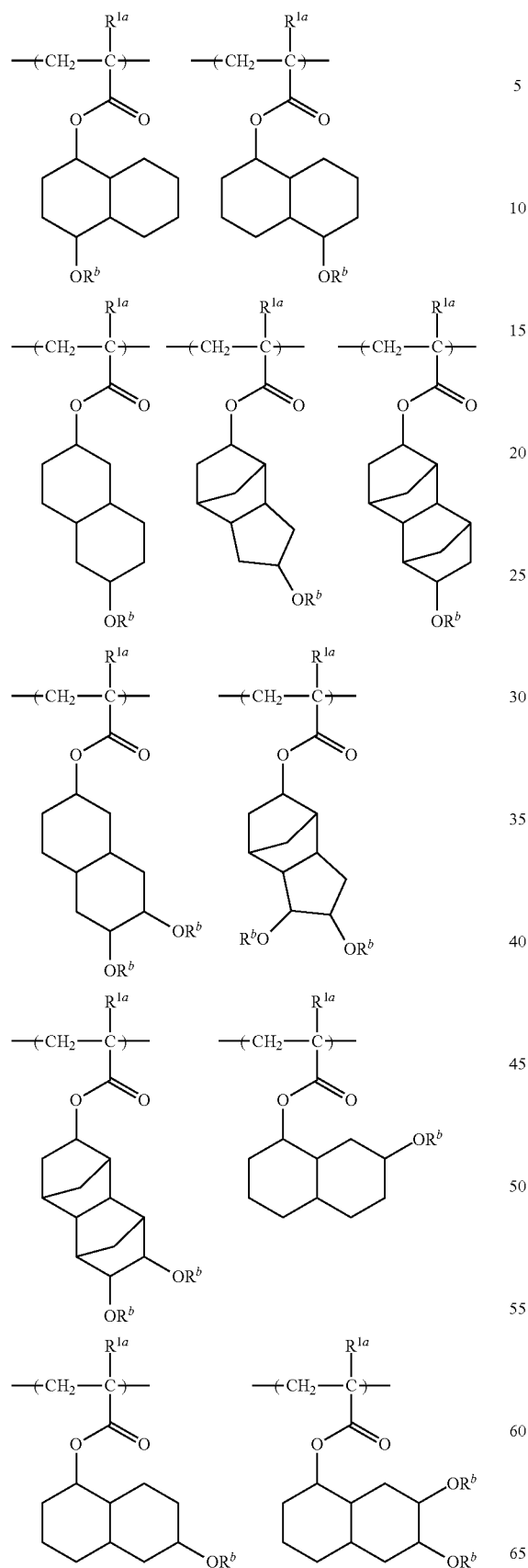
70
-continued
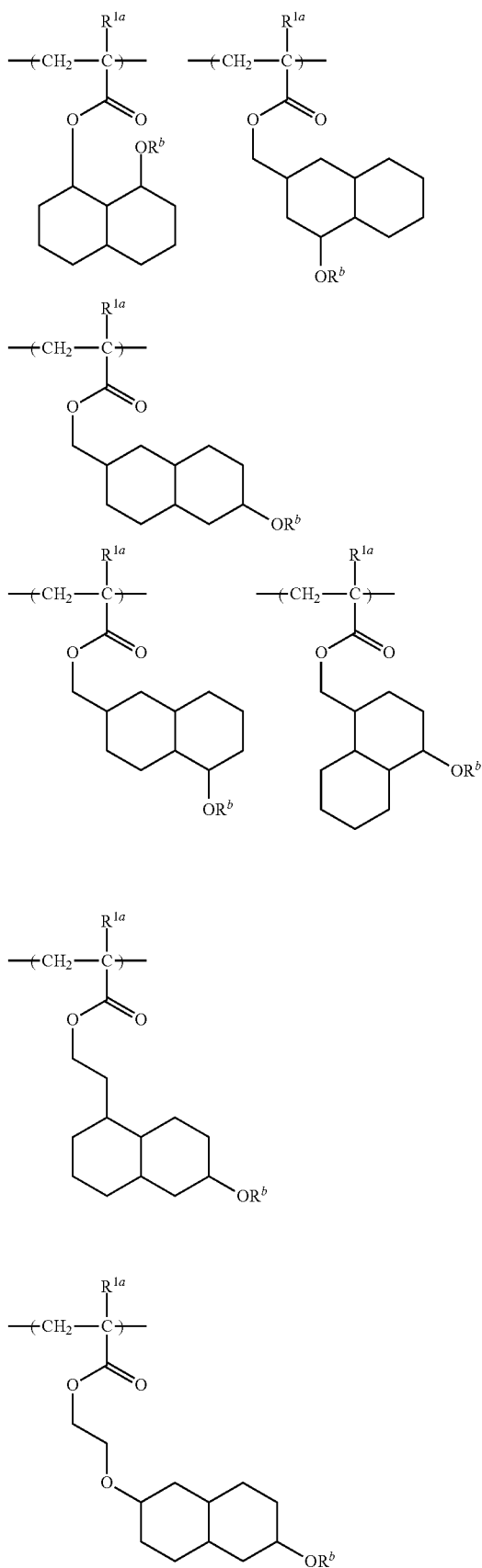

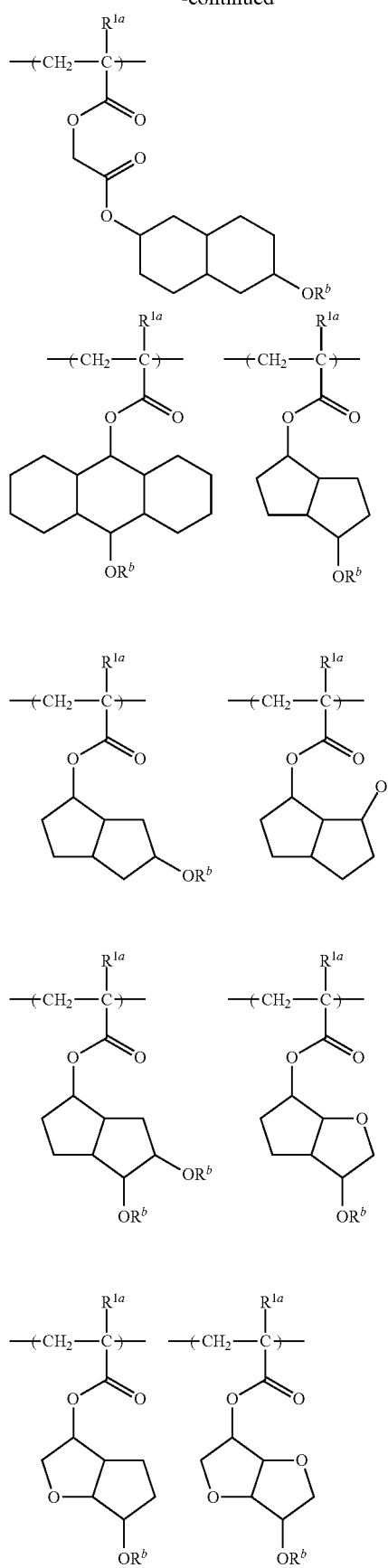
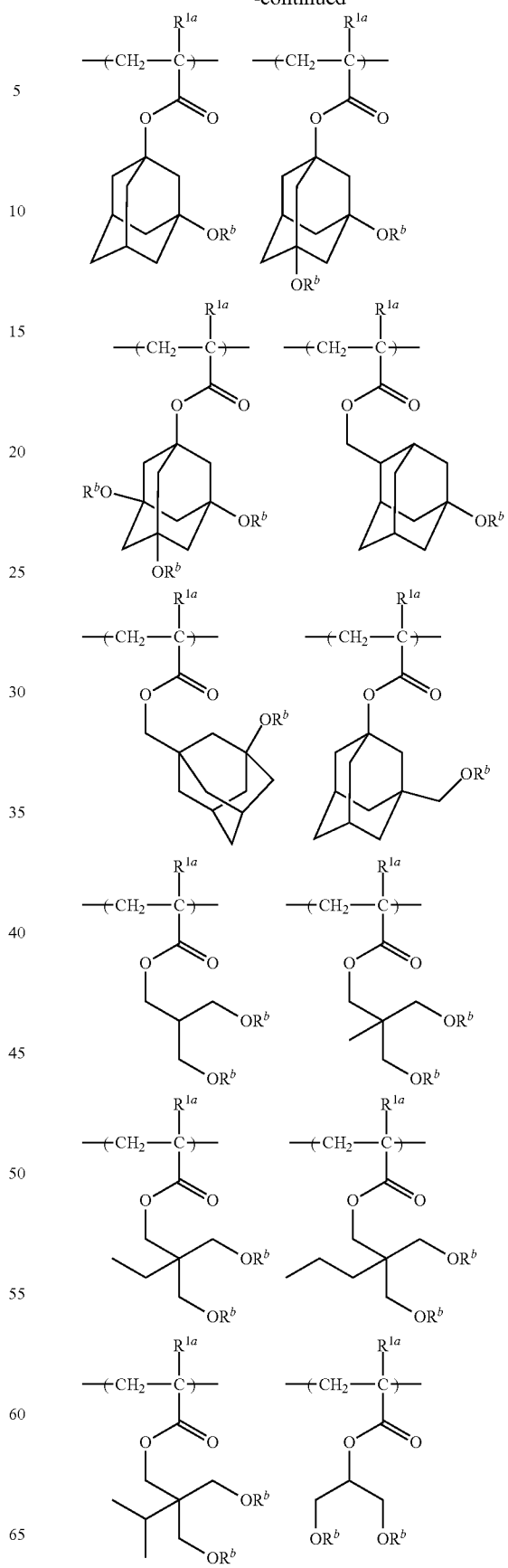

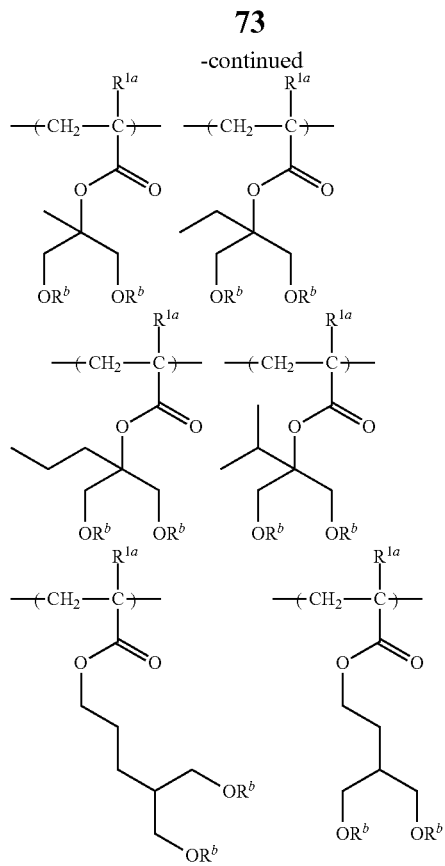

Herein, $R^{1a}$ and $R^b$ are as defined above.

The acid labile group $R^b$ in formula (e2) is not particularly limited as long as it is deprotected under the action of acid to generate a hydroxyl group. Suitable acid labile groups include acetal structure groups, ketal structure groups, and alkoxycarbonyl groups, examples of which are shown below.

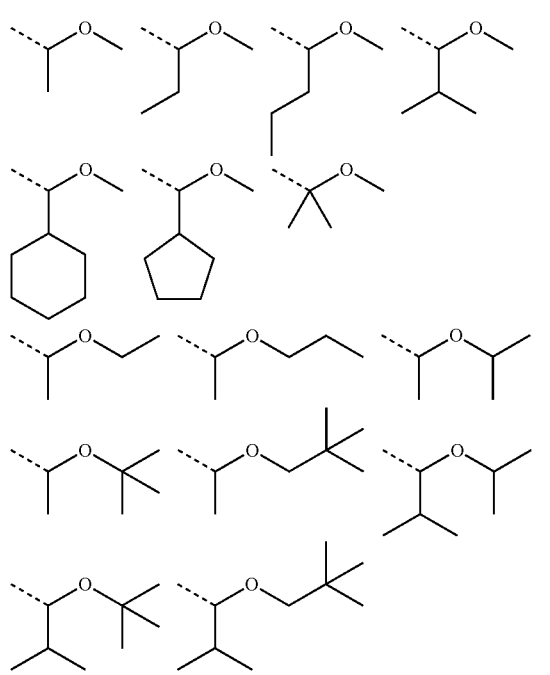

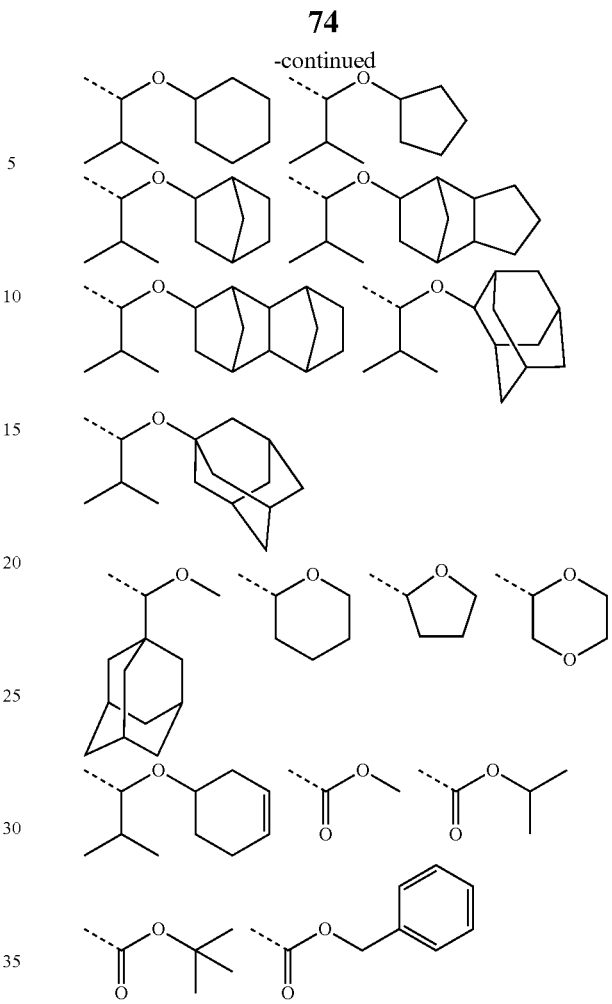

Of the acid labile groups represented by $R^b$ in formula (e2), alkoxymethyl groups having the general formula (e3) are most preferred.

(e3)

Herein $R^c$ is a straight $C_1$-$C_{15}$ or branched or cyclic $C_3$-$C_{15}$ monovalent hydrocarbon group.

Illustrative examples of the acid labile group having formula (e3) are given below, but not limited thereto.

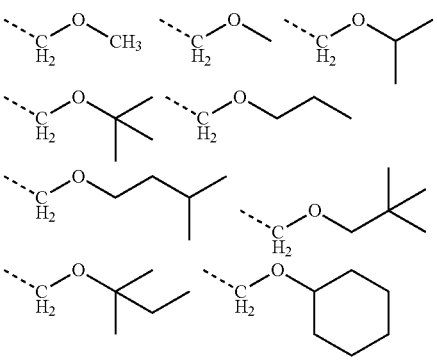

-continued
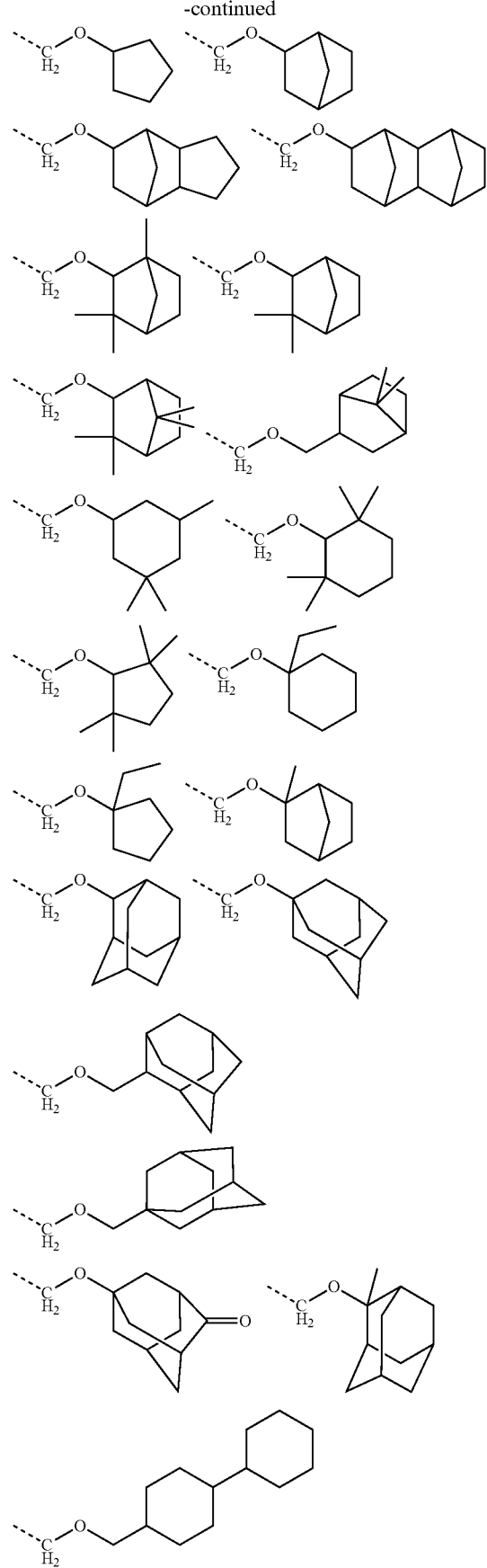
-continued
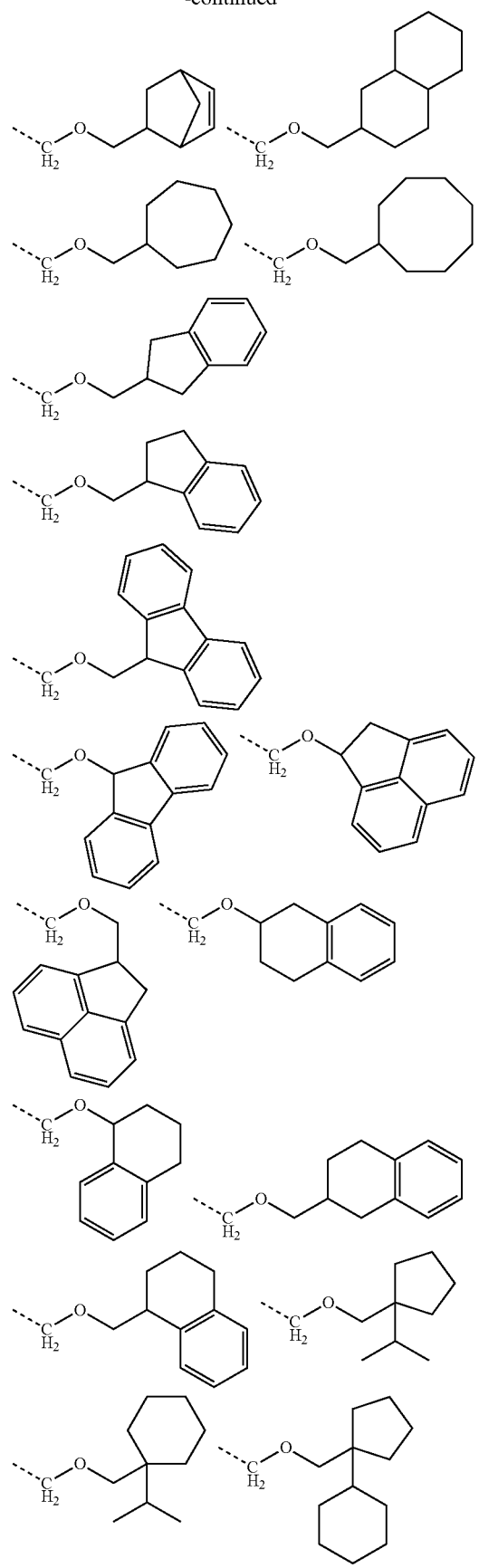

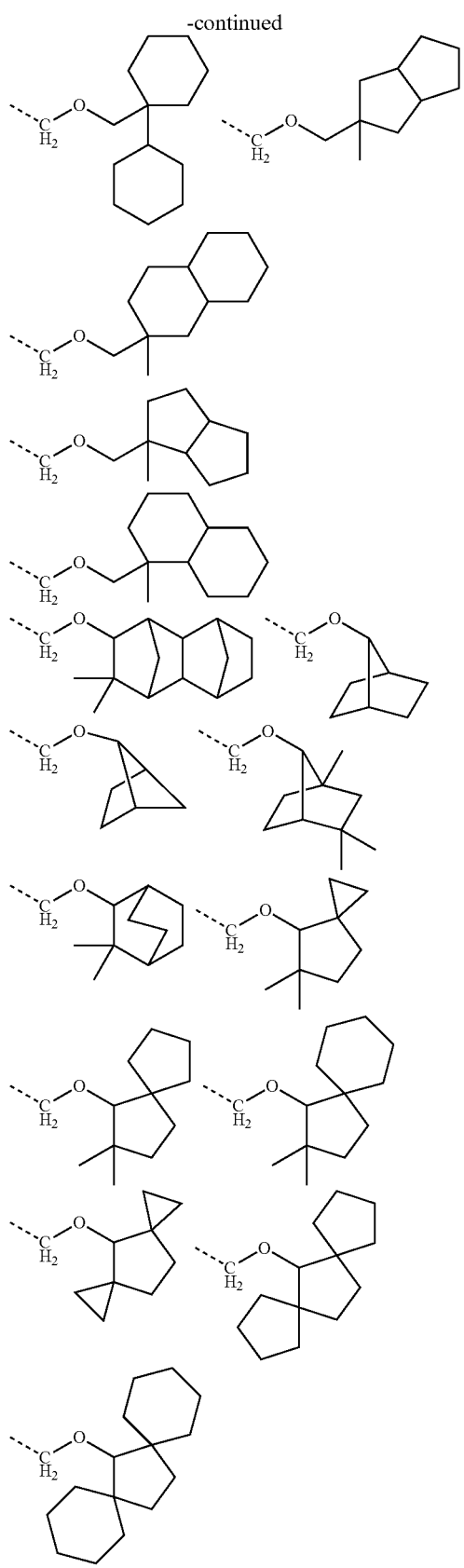

recurring units are derived from substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[6.2.1.1$^{3,6}$.0$^{2,7}$]dodecene derivatives, unsaturated acid anhydrides such as itaconic anhydride, and other monomers. As the hydrogenated ROMP polymer, those described in JP-A 2003-066612 may be used.

The polymer used herein generally has a weight average molecular weight (Mw) of 1,000 to 500,000, and preferably 3,000 to 100,000, as measured by GPC using polystyrene standards. Outside the range, there may result an extreme drop of etch resistance, and a drop of resolution due to difficulty to gain a dissolution rate difference before and after exposure.

The polymer may be synthesized by any desired method, for example, by dissolving an unsaturated bond-containing monomer or monomers in an organic solvent, adding a radical initiator, and effecting heat polymerization. Suitable organic solvents used herein include toluene, benzene, tetrahydrofuran, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours. The acid labile group that has been incorporated in the monomer may be kept as such, or the polymer may be protected or partially protected therewith at the end of polymerization.

In the polymer (B), appropriate molar fractions (mol %) of the respective recurring units derived from the monomers are given below although the invention is not limited thereto. The polymer may comprise:

I) constituent units of at least one type having formula (2) in a fraction of 1 to 60 mol %, preferably 5 to 50 mol %, and more preferably 10 to 50 mol %, II) constituent units of at least one type having formula (3) in a fraction of 40 to 99 mol %, preferably 50 to 95 mol %, and more preferably 50 to 90 mol %, and optionally, III) constituent units of at least one type having formula (d1) or (d2) in a fraction of 0 to 30 mol %, preferably 0 to 20 mol %, and more preferably 0 to 10 mol %, and optionally, IV) constituent units of at least one type derived from another monomer in a fraction of 0 to 80 mol %, preferably 0 to 70 mol %, and more preferably 0 to 50 mol %.

(C) PAG of Formula (4)

While the resist composition of the invention essentially comprises the acid diffusion controlling agent (onium salt) having formula (1), it preferably further comprises a photoacid generator (PAG) having the general formula (4).

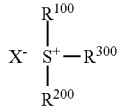

(4)

Herein R$^{100}$, R$^{200}$, and R$^{300}$ are as defined above. X$^-$ is an anion of the general formula (5), (6), (7) or (8).

(5)

The polymer used herein may have additional recurring units further copolymerized therein. Suitable additional -continued

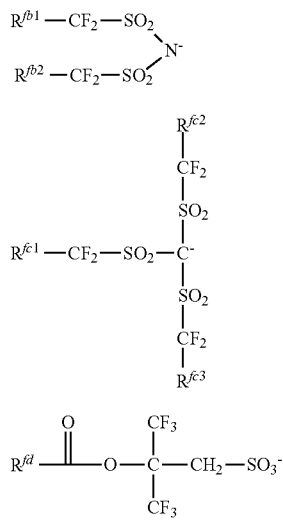

Herein $R^{fa}$, $R^{fb1}$, $R^{fb2}$, $R^{fc1}$, $R^{fc2}$, and $R^{fc3}$ are each independently fluorine or a straight $C_1$-$C_{40}$ or branched or cyclic $C_3$-$C_{40}$ monovalent hydrocarbon group which may be substituted with or separated by a heteroatom. A pair of $R^{fb1}$ and $R^{fb2}$ or $R^{fc1}$ and $R^{fc2}$ may bond together to form a ring with the segments to which they are attached. $R^{fd}$ is a straight $C_1$-$C_{40}$ or branched or cyclic $C_3$-$C_{40}$ monovalent hydrocarbon group which may be substituted with or separated by a heteroatom.

In formula (5), $R^{fa}$ is fluorine or a straight $C_1$-$C_{40}$ or branched or cyclic $C_3$-$C_{40}$ monovalent hydrocarbon group which may be substituted with or separated by a heteroatom.

Of the structures of formula (5), a structure having the general formula (5') is preferred.

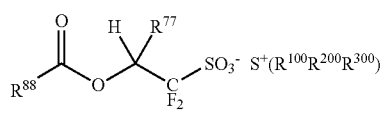

Herein $R^{77}$ is hydrogen or trifluoromethyl; $R^{88}$ is a straight $C_1$-$C_{30}$ or branched or cyclic $C_3$-$C_{30}$ monovalent hydrocarbon group which may be substituted with or separated by a heteroatom; $R^{100}$, $R^{200}$ and $R^{300}$ are as defined above.

In formula (5'), $R^{88}$ is a straight $C_1$-$C_3$, or branched or cyclic $C_3$-$C_{30}$ monovalent hydrocarbon group which may be substituted with or separated by a heteroatom. Of the heteroatoms contained in $R^{88}$, oxygen, nitrogen, sulfur and halogen atoms are preferred, with oxygen being most preferred. Of the monovalent hydrocarbon groups represented by $R^{88}$, those groups of 6 to 30 carbon atoms are preferred from the aspect of achieving a high resolution in forming patterns of fine feature size. Suitable monovalent hydrocarbon groups represented by $R^{88}$ include, but are not limited to, methyl, ethyl, propyl, isopropyl, butyl, isobutyl, sec-butyl, tert-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, eicosanyl, allyl, benzyl, diphenylmethyl, tetrahydrofuryl, methoxymethyl, ethoxymethyl, methylthiomethyl, acetamidomethyl, trifluoromethyl, (2-methoxyethoxy)methyl, acetoxymethyl, 2-carboxy-1-cyclohexyl, 2-oxopropyl, 4-oxo-1-adamantyl, and 3-oxocyclohexyl, With respect to the synthesis of sulfonium salts having formula (5'), reference may be made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the preferred PAG are shown below.

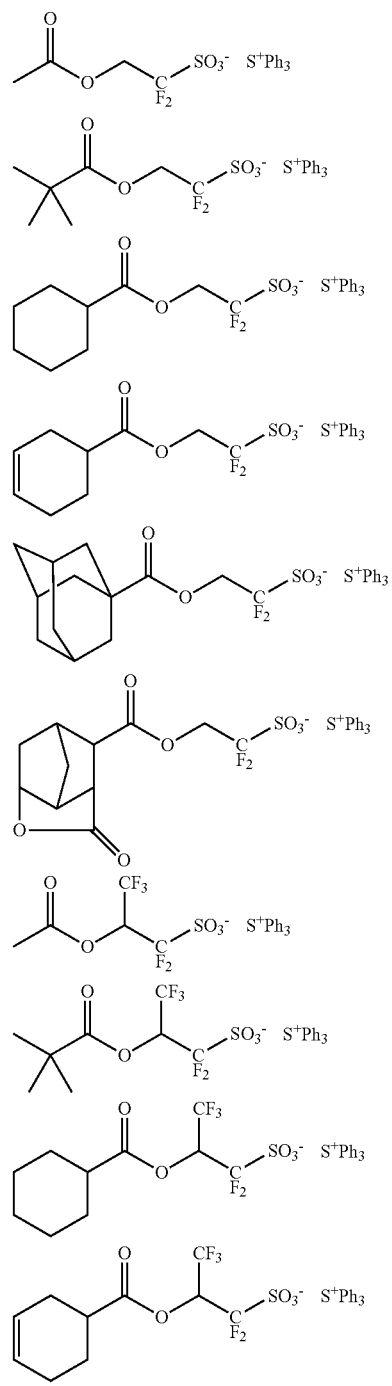

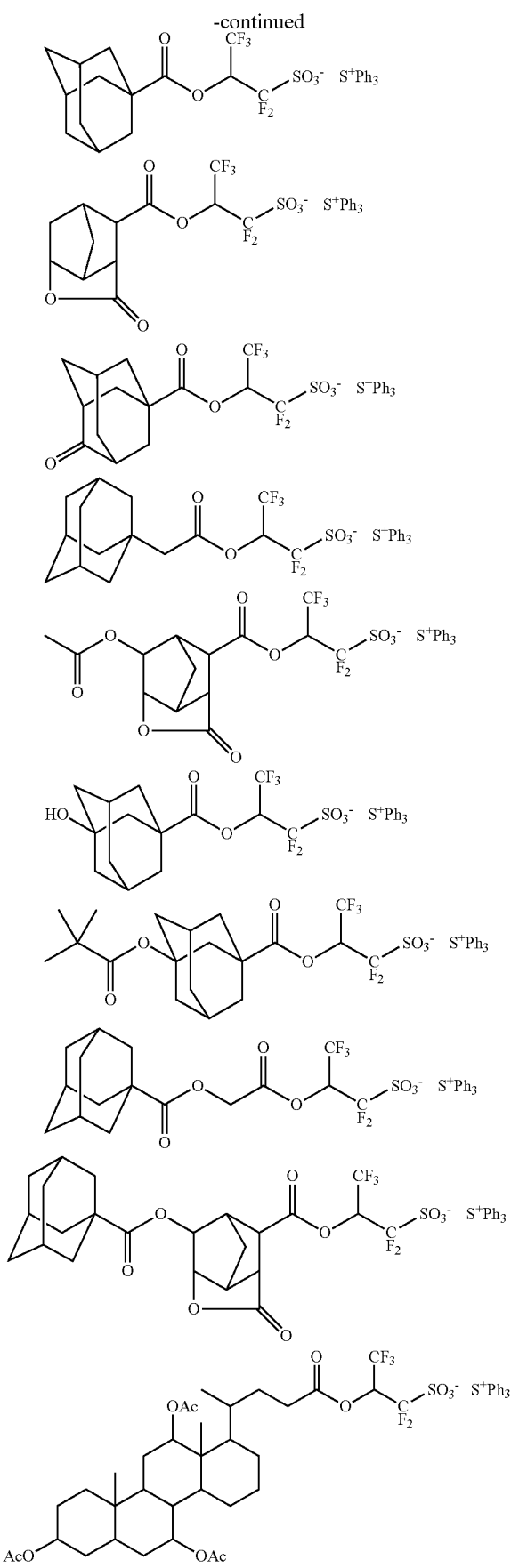
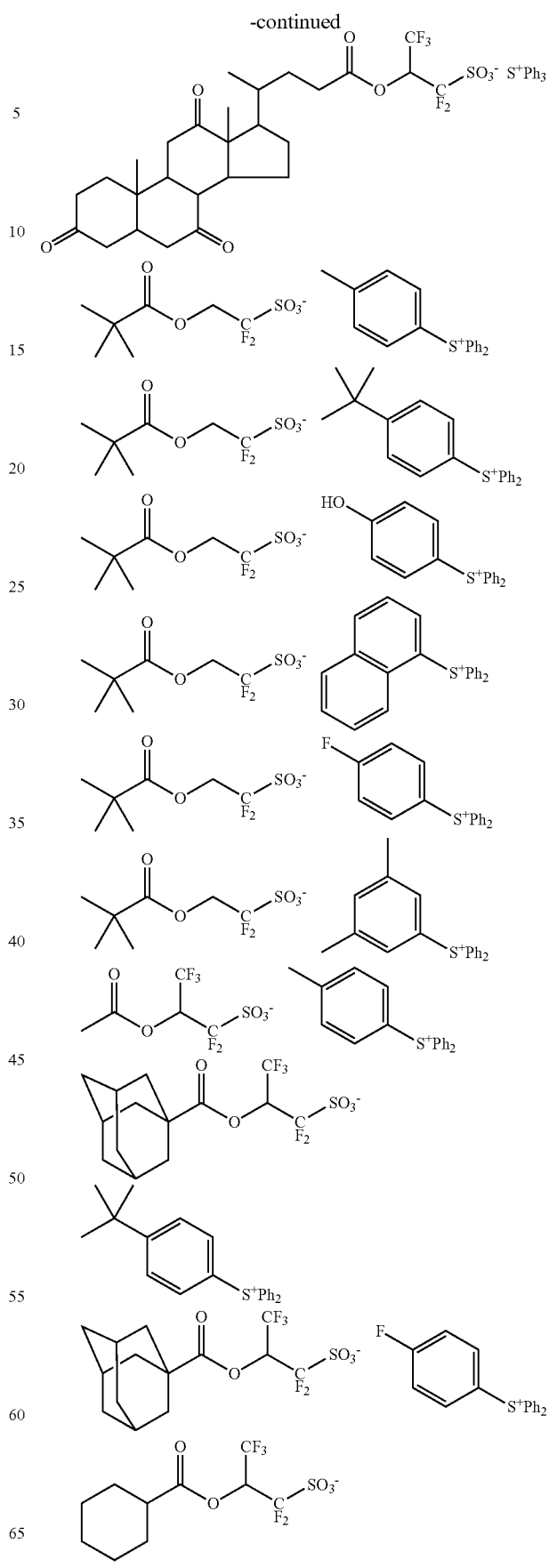

-continued

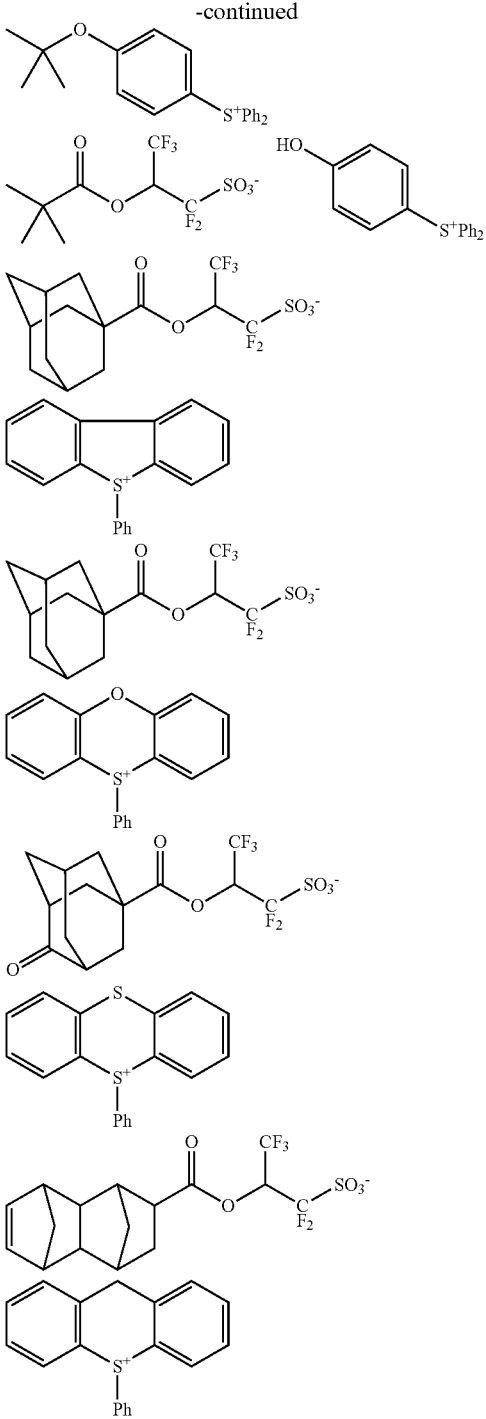

In formula (6), $R^{fb1}$ and $R^{fb2}$ are each independently fluorine or a straight $C_1$-$C_{40}$ or branched or cyclic $C_3$-$C_{40}$ monovalent hydrocarbon group which may be substituted with or separated by a heteroatom. Illustrative examples of the monovalent hydrocarbon group are as exemplified for $R^{fa}$. Preferably $R^{fb1}$ and $R^{fb2}$ are fluorine or $C_1$-$C_4$ straight fluorinated alkyl groups. Also, $R^{fb1}$ and $R^{fb2}$ may bond together to form a ring with the linkage: —$CF_2$—$SO_3$—$N^-$—$SO_2$—$CF_2$— to which they are attached. It is preferred to form a ring structure via a fluorinated ethylene or fluorinated propylene group.

In formula (7), $R^{fc1}$, $R^{fc2}$ and $R^{fc3}$ are each independently fluorine or a straight $C_1$-$C_{40}$ or branched or cyclic $C_3$-$C_{40}$ monovalent hydrocarbon group which may be substituted with or separated by a heteroatom. Illustrative examples of the monovalent hydrocarbon group are as exemplified for $R^{fa}$. Preferably $R^{fc1}$, $R^{fc2}$ and $R^{fc3}$ are fluorine or $C_1$-$C_4$ straight fluorinated alkyl groups. Also, $R^{fc1}$ and $R^{fc2}$ may bond together to form a ring with the linkage: —$CF_2$—$SO_2$—$C^-$—$SO_2$—$CF_2$— to which they are attached. It is preferred to form a ring structure via a fluorinated ethylene or fluorinated propylene group.

In formula (8), $R^{fd}$ is a straight $C_1$-$C_{40}$ or branched or cyclic $C_3$-$C_{40}$ monovalent hydrocarbon group which may be substituted with or separated by a heteroatom. Of the heteroatoms contained in $R^{fd}$, oxygen, nitrogen, sulfur and halogen atoms are preferred, with oxygen being most preferred. Of the monovalent hydrocarbon groups represented by $R^{fd}$, those groups of 6 to 30 carbon atoms are preferred from the aspect of achieving a high resolution in forming patterns of fine feature size. Suitable monovalent hydrocarbon groups represented by $R^{fd}$ include, but are not limited to, methyl, ethyl, propyl, isopropyl, butyl, isobutyl, sec-butyl, tert-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, eicosanyl, allyl, benzyl, diphenylmethyl, tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of sulfonium salts having the anion of formula (8), reference may be made to JP-A 2010-215608.

Examples of the preferred PAG are shown below.

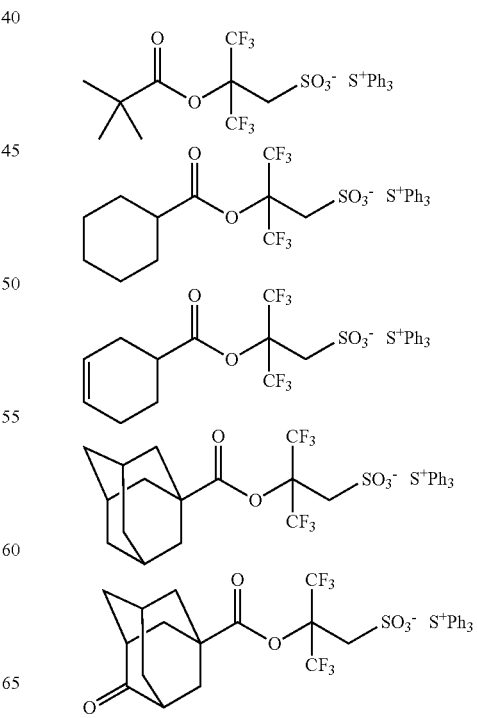

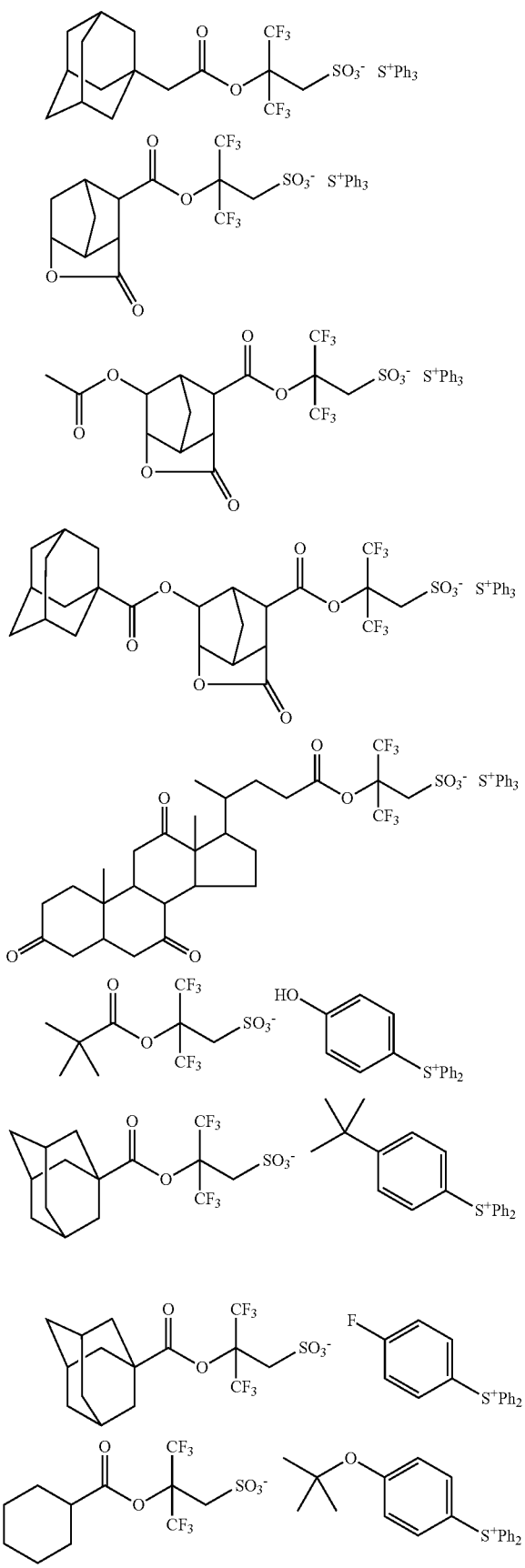
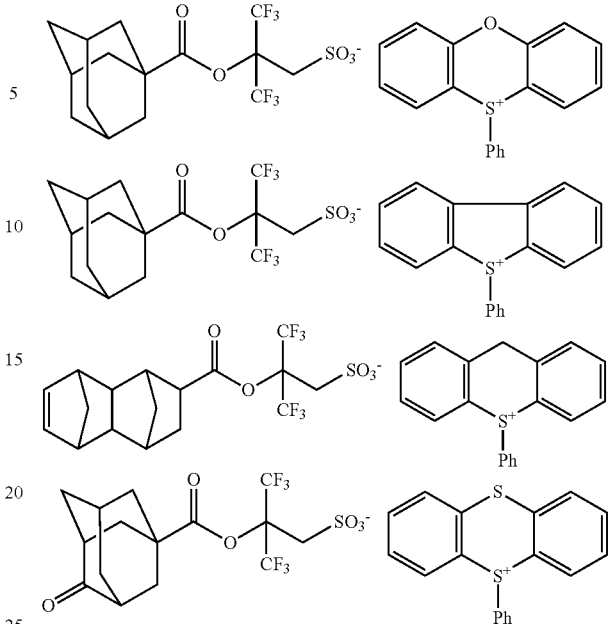

Notably, the compound having the anion of formula (8) does not have fluorine at the α-position relative to the sulfo group, but two trifluoromethyl groups at the β-position. For this reason, it has a sufficient acidity to sever the acid labile groups in the resist polymer. Thus the compound is an effective PAG.

Of the foregoing PAG's, those compounds having the structure of formula (5') or formula (8) are preferred because of suppressed acid diffusion and high solubility in the resist solvent.

The amount of the PAG (C) added is preferably 0 to 40 parts, specifically 0.1 to 40 parts if used, more preferably 0.1 to 20 parts by weight per 100 parts by weight of the base resin. Too large an amount of the PAG may give rise to problems such as degraded resolution and foreign particles during development and resist film stripping.

(D) Organic Solvent

The organic solvent (D) used herein may be any organic solvent in which the polymer (base resin), PAG, controlling agent, and other components are soluble. Examples of the organic solvent include ketones such as cyclohexanone and methyl 2-n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, and mixtures thereof, as described in JP-A 2008-111103, paragraphs [0144] to [0145]. Where an acid labile group of acetal type is used, a high-boiling alcohol solvent may be added for accelerating deprotection reaction of acetal, for example, diethylene glycol, propylene glycol, glycerol, 1,4-butanediol, or 1,3-butanediol. Of the above organic solvents, it is recommended to use 1-ethoxy-2- propanol, PGMEA, cyclohexanone, γ-butyrolactone, and mixtures thereof because the acid generator is most soluble therein.

An appropriate amount of the organic solvent used is 200 to 5,000 parts, more preferably 400 to 3,000 parts by weight per 100 parts by weight of the base resin.

(E) Nonionic Nitrogen-Containing Compound

While the acid diffusion controlling agent (A) is essential in the resist composition, a nitrogen-containing compound other than component (A) may be added as the acid diffusion controlling agent. Suitable nitrogen-containing compounds include primary, secondary and tertiary amine compounds, specifically amine compounds having a hydroxyl group, ether bond, ester bond, lactone ring, cyano group or sulfonate bond, as described in JP-A 2008-111103, paragraphs [0146] to [0164](U.S. Pat. No. 7,537,880). Also useful are compounds whose primary or secondary amine is protected in carbamate form as described in JP 3790649.

The nitrogen-containing compounds may be used alone or in admixture of two or more. The nitrogen-containing compound is preferably used in an amount of 0.001 to 12 parts, more preferably 0.01 to 8 parts by weight per 100 parts by weight of the base resin.

Also, a sulfonium salt of sulfonic acid having a nitrogen-containing substituent may be used in combination as the acid diffusion controlling agent. This compound is a so-called photo-degradable base which functions as quencher in the unexposed region, but loses quencher ability through neutralization with the acid generated by itself, in the exposed region. The use of photo-degradable base is effective for enhancing the contrast between exposed and unexposed regions. With respect to the photo-degradable base, reference may be made to JP-A 2009-109595 and JP-A 2012-046501, for example.

(F) Surfactant which is Insoluble or Substantially Insoluble in Water and Soluble in Alkaline Developer, and/or a Surfactant which is Insoluble or Substantially Insoluble in Water and Alkaline Developer (Hydrophobic Resin)

To the resist composition, the surfactant (F) may be added. Reference should be made to those compounds defined as component (S) in JP-A 2010-215608 and JP-A 2011-16746.

While many examples of the surfactant which is insoluble or substantially insoluble in water and alkaline developer are described in these patent documents, preferred examples are FC-4430, Surflon S-381, Surfynol E1004, KH-20 and KH-30, which may be used alone or in admixture. Partially fluorinated oxetane ring-opened polymers having the structural formula (surf-1) are also useful.

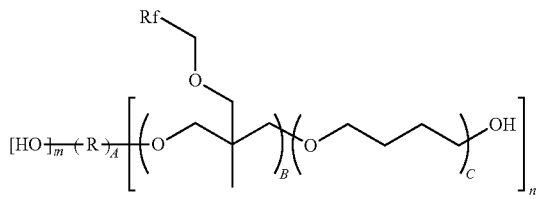

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

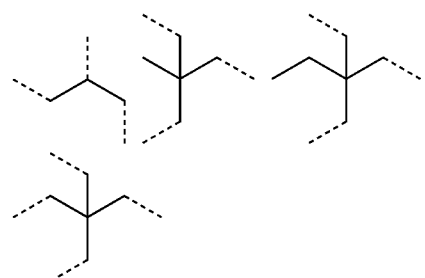

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water slippage. Suitable polymeric surfactants are shown below.

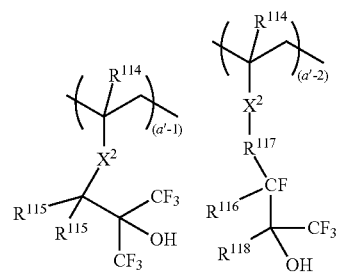

-continued

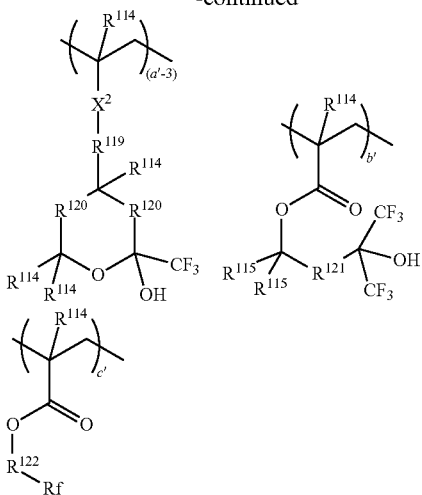

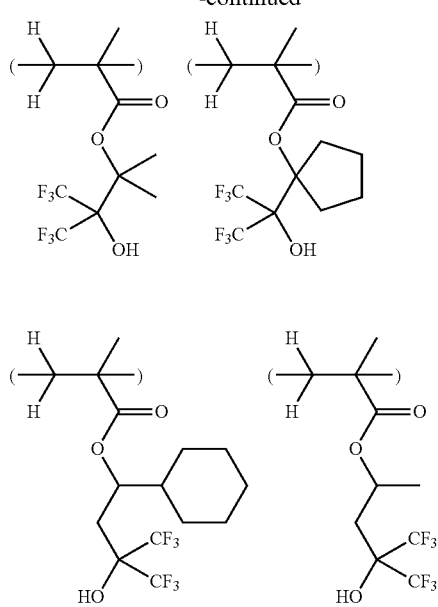

Herein $R^{114}$ is each independently hydrogen, fluorine, methyl or trifluoromethyl. $R^{115}$ is each independently hydrogen or a straight, branched or cyclic $C_1$-$C_{20}$ alkyl or fluoroalkyl group, or two $R^{115}$ in a common monomer may bond together to form a ring with the carbon atom to which they are attached, and in this event, they together represent a straight, branched or cyclic $C_2$-$C_{20}$ alkylene or fluoroalkylene group. $R^{116}$ is fluorine or hydrogen, or $R^{116}$ may bond with $R^{117}$ to form a non-aromatic ring of 3 to 10 carbon atoms in total with the carbon atom to which they are attached. $R^{117}$ is a straight, branched or cyclic $C_1$-$C_6$ alkylene group in which at least one hydrogen atom may be substituted by a fluorine atom. $R^{115}$ is a straight or branched $C_1$-$C_{10}$ alkyl group in which at least one hydrogen atom is substituted by a fluorine atom. Alternatively, $R^{117}$ and $R^{118}$ may bond together to form a non-aromatic ring with the carbon atoms to which they are attached. In this event, $R^{117}$, $R^{118}$ and the carbon atoms to which they are attached together represent a trivalent organic group of 2 to 12 carbon atoms in total. $R^{119}$ is a single bond or a $C_1$-$C_4$ alkylene. $R^{120}$ is each independently a single bond, —O—, or —$CR^{114}R^{114}$—. $R^{121}$ is a straight or branched $C_3$-$C_4$ alkylene group, or may bond with $R^{115}$ within a common monomer to form a $C_3$-$C_6$ non-aromatic ring with the carbon atom to which they are attached. $R^{122}$ is 1,2-ethylene, 1,3-propylene, or 1,4-butylene. Rf is a linear perfluoroalkyl group of 3 to 6 carbon atoms, typically 3H-perfluoropropyl, 4H-perfluorobutyl, 5H-perfluoropentyl, or 6H-perfluorohexyl. $X^2$ is each independently —C(=O)—O—, —O—, or —C(=O)—$R^{123}$—C(=O)—O—. $R^{123}$ is a straight, branched or cyclic $C_1$-$C_{10}$ alkylene group. The subscripts are in the range:
0≤(a'-1)<1, 0≤(a'-2)<1, 0≤(a'-3)<1,
0<(a'-1)+(a'-2)+(a'-3)<1, 0≤b'<1, 0≤c'<1, and
0<(a'-1)+(a'-2)+(a'-3)+b'+c'≤1.

Exemplary units are shown below.

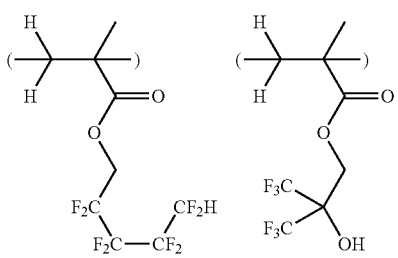

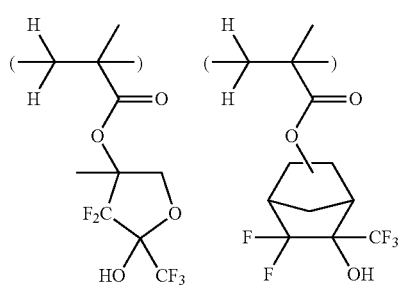

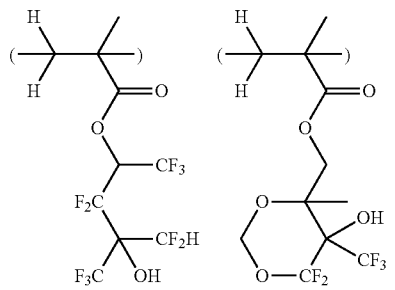

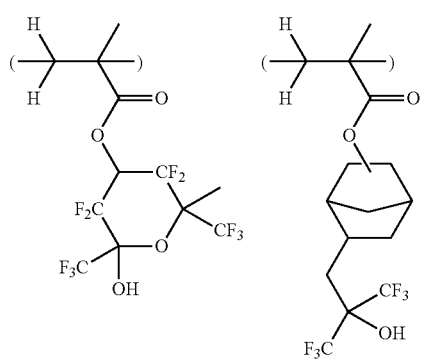

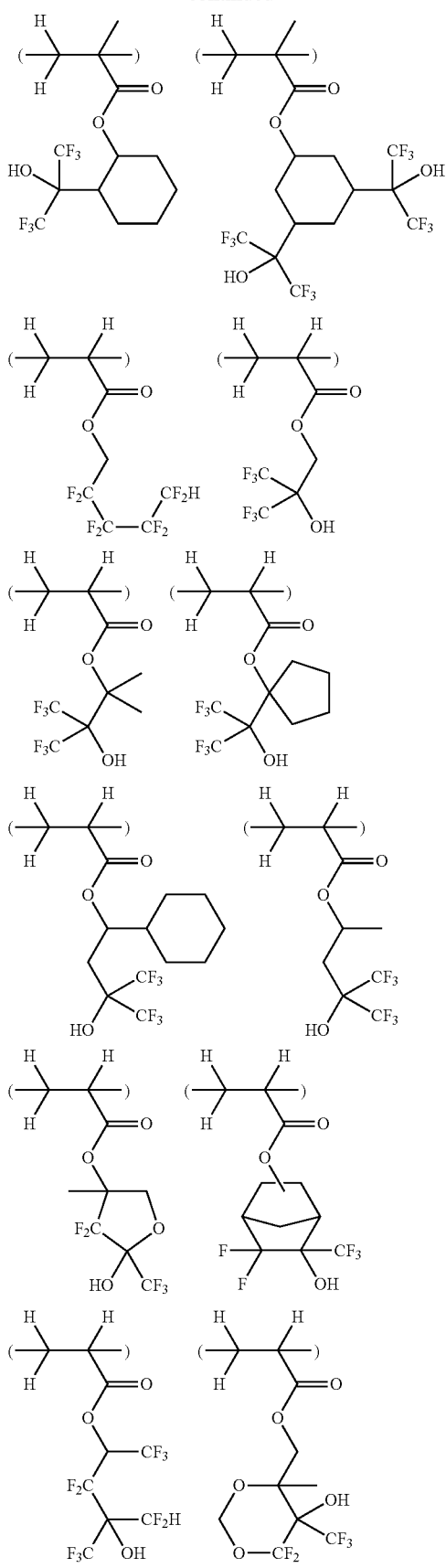

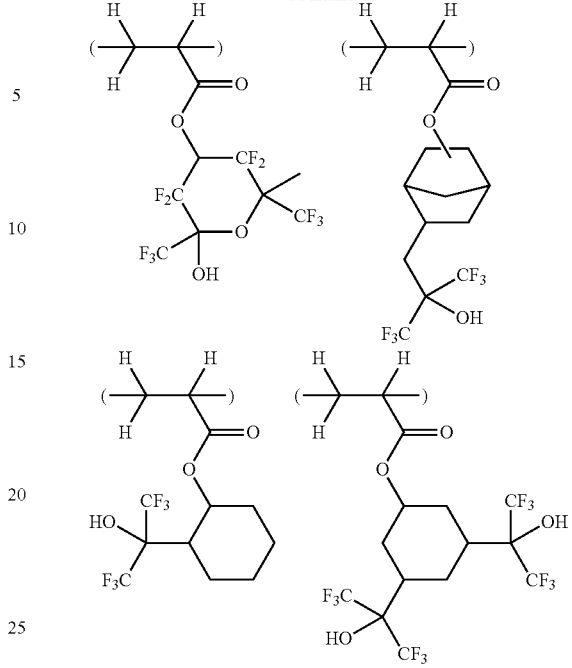

For the surfactant which is insoluble or substantially insoluble in water and soluble in alkaline developer, reference may be made to JP-A 2008-122932, 2010-134012, 2010-107695, 2009-276363, 2009-192784, 2009-191151, 2009-098638, 2010-250105, and 2011-042789.

The polymeric surfactant preferably has a Mw of 1,000 to 50,000, more preferably 2,000 to 20,000 as measured by GPC versus polystyrene standards. A surfactant with a Mw outside the range may be less effective for surface modification and cause development defects. The polymeric surfactant is preferably formulated in an amount of 0.001 to 20 parts, and more preferably 0.01 to 10 parts by weight per 100 parts by weight of the base resin. Reference should also be made to JP-A 2010-215608.

To the resist composition, a compound which is decomposed with an acid to generate another acid, that is, acid amplifier compound may be added. For these compounds, reference should be made to JP-A 2009-269953 and 2010-215608. In the resist composition, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

(G) Organic Acid Derivative and/or Fluorinated Alcohol

Optionally, an organic acid derivative or a compound having a Mw of up to 3,000 which changes its solubility in alkaline developer under the action of an acid, also referred to as dissolution inhibitor, may be added. Reference may be made to JP-A 2009-269953 and 2010-215608.

Process

A further embodiment of the invention is a pattern forming process using the resist composition defined above. A pattern may be formed from the resist composition using any well-known lithography process. The preferred process includes at least the steps of forming a resist film on a substrate, exposing it to high-energy radiation, and developing it in a developer.

The resist composition is applied onto a substrate for integrated circuit fabrication (e.g., Si, SiO$_2$, SiN, SiON, TiN, WSi, BPSG, SOG or organic antireflective coating) or substrate for mask circuit fabrication (e.g., Cr, CrO, CrON or MoSi) by a suitable coating technique such as spin coating. The coating is prebaked on a hot plate at a temperature of 60 to 150° C. for 1 to 10 minutes, preferably 80 to 140° C. for 1 to 5 minutes, to form a resist film of 0.05 to 2.0 μm thick. Through a mask with the desired pattern placed over the resist film, the resist film is exposed to high-energy radiation, typically KrF excimer laser, ArF excimer laser or EUV radiation in a dose of 1 to 200 mJ/cm$^2$, and preferably 10 to 100 mJ/cm$^2$. The exposure may be performed by conventional lithography whereas the immersion lithography of holding a liquid between the mask and the resist film may be employed if desired. In this case, a protective film which is insoluble in water may be applied on the resist film. The resist film is then baked (PEB) on a hot plate at 60 to 150° C. for 1 to 5 minutes, preferably 80 to 140° C. for 1 to 3 minutes. Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

The water-insoluble protective film which is used in the immersion lithography is to prevent any components from being leached out of the resist film and to improve water slippage at the film surface and is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

Any desired step may be added to the pattern forming process. For example, after a photoresist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

The technique enabling the ArF lithography to survive to the 32-nm node is a double patterning process. The double patterning process includes a trench process of processing an underlay to a 1:3 trench pattern by a first step of exposure and etching, shifting the position, and forming a 1:3 trench pattern by a second step of exposure for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

In the pattern forming process, positive tone development may be carried out using an alkaline aqueous solution, typically an aqueous solution of 0.1 to 5 wt %, more typically 2 to 3 wt % of tetramethylammonium hydroxide (TMAH) as the developer. The negative tone development technique wherein the unexposed region is developed and dissolved in an organic solvent is also applicable.

In the organic solvent development, the organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, isoamyl acetate, butenyl acetate, phenyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

EXAMPLE

Examples of the invention are given below by way of illustration and not by way of limitation.

Synthesis Example 1-1

Synthesis of triphenylsulfonium 4-morpholin-4-ylbenzoate (Q-1)

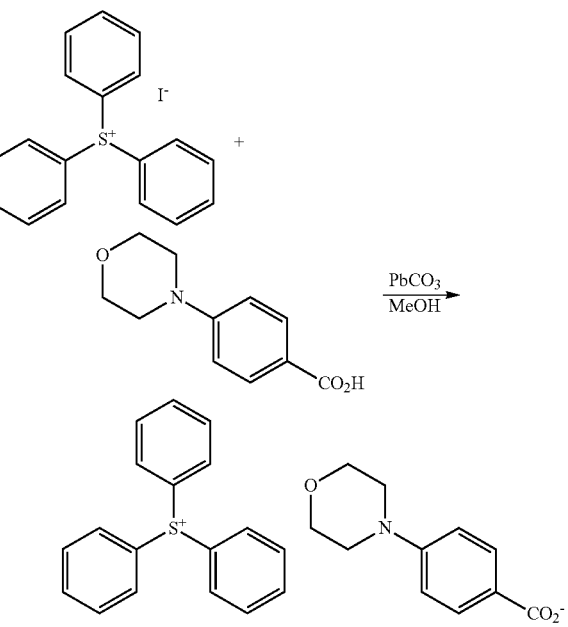

A mixture of 3.1 g of 4-(4-morpholinyl)benzoic acid, 2.0 g of lead carbonate, 5.8 g of triphenylsulfonium iodide, and 30 g of methanol was heated and stirred at 70° C. for 8 hours. The reaction solution was cooled to room temperature and filtered. The filtrate was concentrated under reduced pressure. The solid precipitate was washed with methyl isobutyl ketone and dried under reduced pressure, obtaining 5.8 g of the target compound, triphenylsulfonium 4-morpholin-4-ylbenzoate (yield 83%).

The target compound was analyzed by spectroscopy. The NMR spectrum, $^1$H-NMR in DMSO-$d_6$, is shown in FIG. 1. In $^1$H-NMR analysis, a minute amount of water was observed.

Infrared Absorption Spectrum (IR (D-ATR): Cm$^{-1}$)
 3351, 3082, 3038, 3009, 2995, 2861, 2826, 1601, 1549, 1510, 1478, 1449, 1364, 1347, 1235, 1118, 995, 927, 792, 759, 703, 687, 658 cm$^{-1}$ High-Performance Liquid Chromatography Mass Spectrometry (LC-MS)
 Positive M$^+$ 263 (corresponding to $(C_6H_5)_3S^+$)
 Negative M$^-$ 206 (corresponding to $C_{10}H_{12}NO-CO_2^-$)

Polymers for use in resist compositions were synthesized according to the following formulation. Notably, Mw and Mn are weight and number average molecular weights, respectively, as measured by GPC versus polystyrene standards using THF solvent, and Mw/Mn is a polydispersity index.

Synthesis Example 2-1

Synthesis of Polymer P-1

In nitrogen atmosphere, 22 g of 1-tert-butylcyclopentyl methacrylate, 17 g of 2-oxotetrahydrofuran-3-yl methacrylate, 0.48 g of dimethyl 2,2'-azobis(2-methylpropionate) (V-601 by Wako Pure Chemical Industries, Ltd.), 0.41 g of 2-mercaptoethanol, and 50 g of methyl ethyl ketone were combined to form a monomer/initiator solution. A flask in nitrogen atmosphere was charged with 23 g of methyl ethyl ketone, which was heated at 80° C. with stirring. With stirring, the monomer/initiator solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to 640 g of methanol with vigorous stirring. The precipitate was collected by filtration, washed twice with 240 g of methanol, and vacuum dried at 50° C. for 20 hours, obtaining 36 g of a copolymer in white powder form (yield 90%). On GPC analysis, the copolymer had a Mw of 8,755 and a Mw/Mn of 1.94.

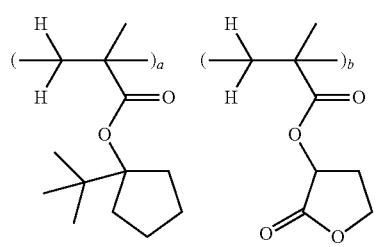

P-1

(a = 0.50, b = 0.50)

Synthesis Examples 2-2 to 2-12

Synthesis of Polymers P-2 to P-12

Polymers were synthesized by the same procedure as in Synthesis Example 2-1 aside from changing the type and amount of monomers. Table 1 shows the proportion (in molar ratio) of units incorporated in these polymers, and Tables 2 and 3 show the structure of recurring units.

TABLE 1

| Polymer | Unit 1 (molar ratio) | Unit 2 (molar ratio) | Unit 3 (molar ratio) | Unit 4 (molar ratio) |
|---|---|---|---|---|
| P-1 | A-1 (0.50) | B-1 (0.50) | — | — |
| P-2 | A-1 (0.40) | B-1 (0.50) | B-3 (0.10) | — |
| P-3 | A-1 (0.50) | B-2 (0.20) | B-3 (0.20) | B-5 (0.10) |
| P-4 | A-2 (0.40) | B-1 (0.60) | — | — |
| P-5 | A-2 (0.40) | B-2 (0.60) | — | — |
| P-6 | A-2 (0.20) | A-3 (0.30) | B-1 (0.40) | B-5 (0.10) |
| P-7 | A-2 (0.20) | A-3 (0.30) | B-2 (0.40) | B-5 (0.10) |
| P-8 | A-1 (0.25) | A-2 (0.25) | B-3 (0.40) | B-5 (0.10) |
| P-9 | A-1 (0.20) | A-2 (0.25) | B-1 (0.35) | B-3 (0.20) |
| P-10 | A-3 (0.25) | A-5 (0.25) | B-1 (0.35) | B-5 (0.15) |
| P-11 | A-4 (0.50) | B-4 (0.50) | — | — |
| P-12 | A-6 (0.35) | B-3 (0.65) | — | — |

TABLE 2

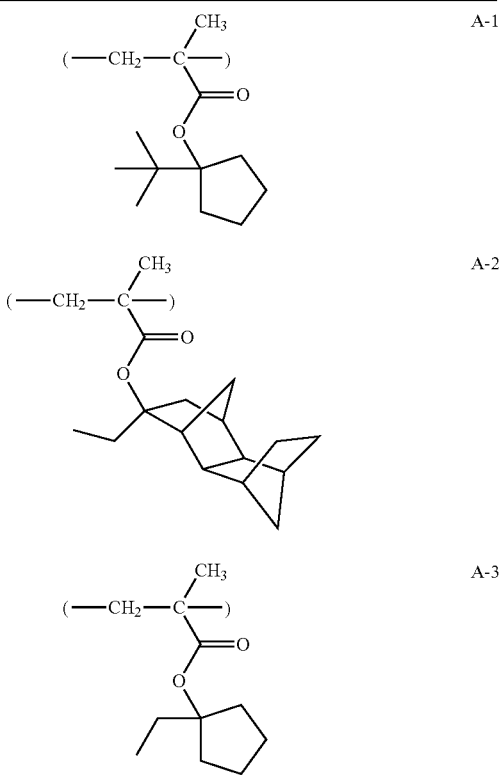

TABLE 2-continued

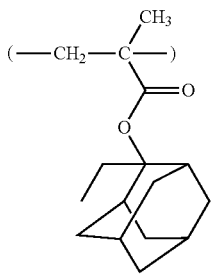 A-4

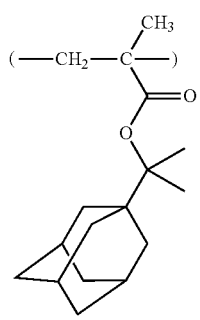 A-5

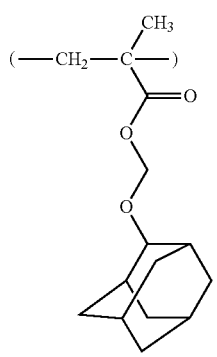 A-6

TABLE 3

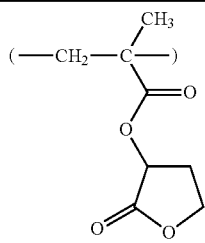 B-1

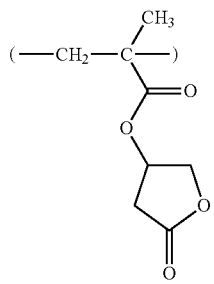 B-2

TABLE 3-continued

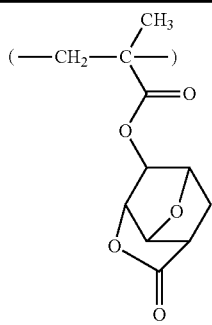 B-3

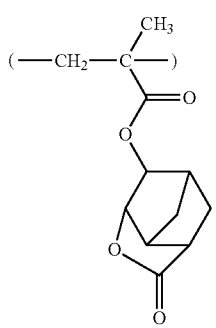 B-4

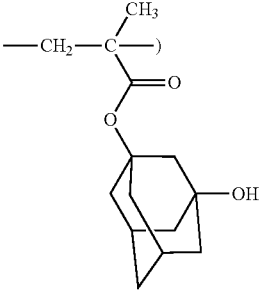 B-5

Examples 1-1 to 1-14 and Comparative Examples 1-1 to 1-7

Preparation of Resist Composition

A resist composition in solution form was prepared by dissolving the acid diffusion controlling agent (Q-1) synthesized above or comparative acid diffusion controlling agents (Q-2) to (Q-7), each polymer (Polymers P-1 to P-12 synthesized above), a photoacid generator (PAG-X, PAG-Y), and alkali-soluble surfactant (SF-1) in an organic solvent containing 0.01 wt % of surfactant A, and filtering through a Teflon® filter with a pore size of 0.2 μm. Table 4 shows the formulation of the resulting resist solution.

The solvent, photoacid generator (PAG-X, PAG-Y), alkali-soluble surfactant (SF-1), surfactant A, and comparative acid diffusion controlling agents (Q-2 to Q-7) used herein are identified below.

PGMEA: propylene glycol monomethyl ether acetate
GBL: γ-butyrolactone
PAG-X: triphenylsulfonium 2-(adamantane-1-carbonyloxy)-1,1,3,3,3-pentafluoropropane-1-sulfonate
PAG-Y: triphenylsulfonium 2-(adamantane-1-carbonyloxy)-3,3,3-trifluoro-2-trifluoromethylpropane-1-sulfonate
Q-2: 2-(4-morpholinyl)ethyl octadecanoate
Q-3: triphenylsulfonium camphorsulfonate Q-4: triphenylsulfonium 1-adamantanecarboxylate (synthesized by the same procedure as in Synthesis Example 1)

Q-5: triphenylsulfonium pyridine-2-carboxylate (prepared according to JP-A 2007-293250)

Q-6: compound of the structure shown below (prepared according to JP-A 2012-123189)

Q-7: compound of the structure shown below (prepared according to JP-A 2006-208781)

(Q-6)

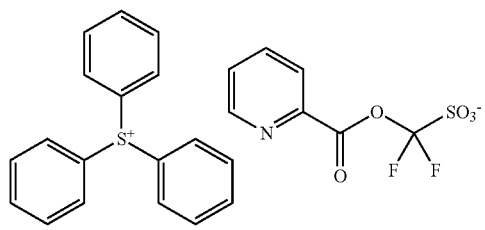

(Q-7)

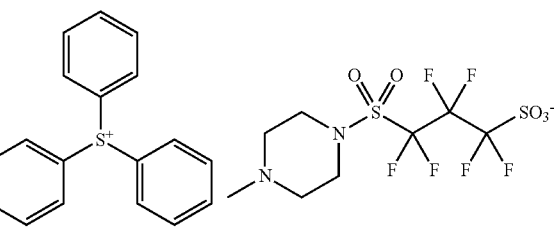

Surfactant (SF-1):
poly(2,2,3,3,4,4,4-heptafluoro-1-isobutyl-1-butyl methacrylate/9-(2,2,2-trifluoro-1-trifluoroethyl-oxycarbonyl)-4-oxatricyclo[4.2.1.0$^{3,7}$]nonan-5-on-2-yl methacrylate)
Mw=7,700
Mw/Mn=1.82

(SF-1)

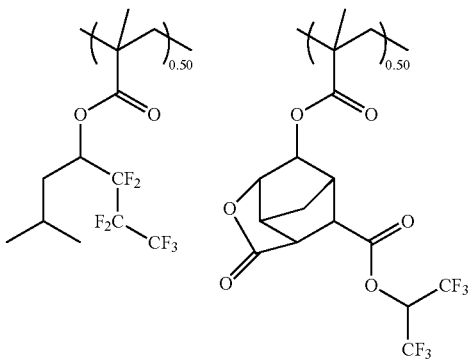

Surfactant A:
3-methyl-3-(2,2,2-trifluoroethoxymethyl)oxetane/tetrahydrofuran/2,2-dimethyl-1,3-propanediol copolymer (Omnova Solutions, Inc.)

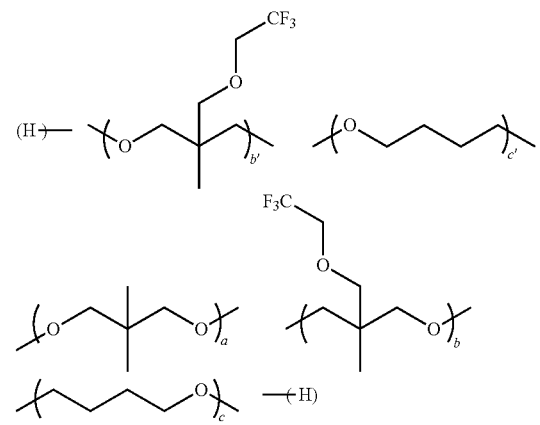

a:(b+b'):(c+c')=1:4–7:0.01–1 (molar ratio)
Mw=1,500

TABLE 4

|  |  | Resist | Resin (pbw) | PAG (pbw) | Acid diffusion control agent (pbw) | Surfactant (pbw) | Solvent 1 (pbw) | Solvent 2 (pbw) |
|---|---|---|---|---|---|---|---|---|
| Example | 1-1 | R-1 | P-1 (80) | PAG-X (7.6) | Q-1 (2.5) | SF-1 (3.0) | PGMEA (1,728) | GBL (192) |
|  | 1-2 | R-2 | P-2 (80) | PAG-X (7.6) | Q-1 (2.5 | SF-1 (3.0) | PGMEA (1,728) | GBL (192) |
|  | 1-3 | R-3 | P-3 (80) | PAG-X (7.6) | Q-1 (2.5) | SF-1 (3.0) | PGMEA (1,728) | GBL (192) |
|  | 1-4 | R-4 | P-4 (80) | PAG-X (7.6) | Q-1 (2.5) | SF-1 (3.0) | PGMEA (1,728) | GBL (192) |
|  | 1-5 | R-5 | P-5 (80) | PAG-X (7.6) | Q-1 (2.5) | SF-1 (3.0) | PGMEA (1,728) | GBL (192) |
|  | 1-6 | R-6 | P-6 (80) | PAG-X (7.6) | Q-1 (2.5) | SF-1 (3.0) | PGMEA (1,728) | GBL (192) |
|  | 1-7 | R-7 | P-7 (80) | PAG-X (7.6) | Q-1 (2.5) | SF-1 (3.0) | PGMEA (1,728) | GBL (192) |
|  | 1-8 | R-8 | P-8 (80) | PAG-X (7.6) | Q-1 (2.5) | SF-1 (3.0) | PGMEA (1,728) | GBL (192) |
|  | 1-9 | R-9 | P-9 (80) | PAG-X (7.6) | Q-1 (2.5) | SF-1 (3.0) | PGMEA (1,728) | GBL (192) |
|  | 1-10 | R-10 | P-10 (80) | PAG-X (7.6) | Q-1 (2.5) | SF-1 (3.0) | PGMEA (1,728) | GBL (192) |
|  | 1-11 | R-11 | P-11 (80) | PAG-X (7.6) | Q-1 (2.5) | SF-1 (3.0) | PGMEA (1,728) | GBL (192) |

TABLE 4-continued

|  |  | Resist | Resin (pbw) | PAG (pbw) | Acid diffusion control agent (pbw) | Surfactant (pbw) | Solvent 1 (pbw) | Solvent 2 (pbw) |
|---|---|---|---|---|---|---|---|---|
|  | 1-12 | R-12 | P-12 (80) | PAG-X (7.6) | Q-1 (2.5) | SF-1 (3.0) | PGMEA (1,728) | GBL (192) |
|  | 1-13 | R-13 | P-1 (80) | PAG-X (13.3) | Q-1 (2.5) | SF-1 (3.0) | PGMEA (1,728) | GBL (192) |
|  | 1-14 | R-14 | P-2 80 | PAG-Y (13.3) | Q-1 (2.5) | SF-1 (3.0) | PGMEA (1,728) | GBL (192) |
| Comparative Example | 1-1 | R-15 | P-1 (80) | PAG-X (7.6) | Q-2 (1.7) | SF-1 (3.0) | PGMEA (1,728) | GBL (192) |
|  | 1-2 | R-16 | P-1 (80) | PAG-X (7.6) | Q-3 (3.8) | SF-1 (3.0) | PGMEA (1,728) | GBL (192) |
|  | 1-3 | R-17 | P-1 (80) | PAG-X (7.6) | Q-4 (3.4) | SF-1 (3.0) | PGMEA (1.728) | GBL (192) |
|  | 1-4 | R-18 | P-1 (80) | PAG-X (7.6) | Q-5 (3.0) | SF-1 (3.0) | PGMEA (1,728) | GBL (192) |
|  | 1-5 | R-19 | P-1 (80) | PAG-X (7.6) | Q-6 (4.1) | SF-1 (3.0) | PGMEA (1,728) | GBL (192) |
|  | 1-6 | R-20 | P-1 (80) | PAG-X (7.6) | Q-7 (5.1) | SF-1 (3.0) | PGMEA (1,728) | GBL (192) |
|  | 1-7 | R-21 | P-1 (80) | PAG-Y (13.3) | Q-2 (1.7) | SF-1 (3.0) | PGMEA (1,728) | GBL (192) |

Examples 2-1 to 2-14 and Comparative Examples 2-1 to 2-7

Resist Test 1 (ArF Lithography)

On a silicon substrate, an antireflective coating solution (ARC-29A, Nissan Chemical Industries, Ltd.) was coated and baked at 200° C. for 60 seconds to form an ARC of 100 nm thick. Each of the resist solutions shown in Table 4 was spin coated on the silicon substrate and baked on a hot plate at 100° C. for 60 seconds, forming a resist film of 90 nm thick on the ARC. The wafer was exposed on an ArF excimer laser immersion lithography scanner (NSR-S610C by Nikon Corp., NA 1.30, dipole illumination, Cr mask), baked (PEB) at 80° C. for 60 seconds, and developed in a 2.38 wt % tetramethylammonium hydroxide (TMAH) aqueous solution for 60 seconds, forming a pattern.

Resist evaluation was made on a 40-nm 1:1 line-and-space pattern. On observation under an electron microscope, the optimum exposure dose (Eop) was defined as an exposure dose (mJ/cm$^2$) which provided a line width of 40 nm.

The width of lines of a 40-nm 1:1 line-and-space pattern was measured under SEM to determine a line width variation (30 points measured, 3σ value computed), which was reported as line width roughness (LWR). A smaller value of LWR indicates a line pattern with a less fluctuation and of better profile. In this test, the sample is rated good when LWR is equal to or less than 3.0 nm and poor when LWR is equal to or more than 3.1 nm.

An L/S pattern was formed by exposure in the optimum dose (determined in the sensitivity evaluation) through the mask with the pitch fixed and the line width varied. MEF was calculated from variations of the mask line width and the pattern space width according to the following equation:

MEF=(pattern space width)/(mask line width)−b wherein b is a constant. A value closer to unity (1) indicates better performance.

Further, for a trench pattern printed at the optimum exposure dose, the dependency of trench size on focus was examined. A range (nm) of focus capable of resolution was determined and reported as DOF.

The collapse limit was a minimum width (nm) of lines which could be resolved without collapse when the line width was reduced by increasing the exposure dose. A smaller value indicates better collapse resistance.

The results of evaluation are shown in Table 5.

TABLE 5

|  |  | Resist | Eop (mJ/cm$^2$) | LWR (nm) | MEF | DOF (nm) | Collapse limit (nm) |
|---|---|---|---|---|---|---|---|
| Example | 2-1 | R-1 | 31 | 2.6 | 2.4 | 75 | 30 |
|  | 2-2 | R-2 | 32 | 2.8 | 2.5 | 75 | 28 |
|  | 2-3 | R-3 | 34 | 2.8 | 2.5 | 75 | 27 |
|  | 2-4 | R-4 | 33 | 2.5 | 2.4 | 70 | 29 |
|  | 2-5 | R-5 | 32 | 2.6 | 2.3 | 70 | 30 |
|  | 2-6 | R-6 | 36 | 2.7 | 2.3 | 75 | 27 |
|  | 2-7 | R-7 | 30 | 2.9 | 2.3 | 70 | 26 |
|  | 2-8 | R-8 | 31 | 2.7 | 2.3 | 70 | 27 |
|  | 2-9 | R-9 | 33 | 2.8 | 2.1 | 75 | 27 |
|  | 2-10 | R-10 | 31 | 2.8 | 2.2 | 70 | 28 |
|  | 2-11 | R-11 | 33 | 2.7 | 2.2 | 70 | 29 |
|  | 2-12 | R-12 | 34 | 2.8 | 2.7 | 70 | 29 |
|  | 2-13 | R-13 | 31 | 2.5 | 2.4 | 65 | 30 |
|  | 2-14 | R-14 | 32 | 2.6 | 2.4 | 70 | 27 |
| Comparative Example | 2-1 | R-15 | 38 | 3.5 | 4.0 | 40 | 39 |
|  | 2-2 | R-16 | 31 | 3.1 | 4.3 | 35 | 35 |
|  | 2-3 | R-17 | 35 | 3.3 | 4.1 | 45 | 35 |
|  | 2-4 | R-18 | 34 | 3.4 | 3.9 | 45 | 38 |
|  | 2-5 | R-19 | 33 | 3.2 | 4.3 | 35 | 35 |
|  | 2-6 | R-20 | 32 | 3.3 | 4.2 | 35 | 36 |
|  | 2-7 | R-21 | 40 | 3.3 | 3.9 | 40 | 38 |

As seen from the results of Table 5, the resist compositions within the scope of the invention offer advantages including improved LWR, MEF, DOF, and collapse limit, and are suited as resist material for ArF immersion lithography.

Examples 3-1 to 3-14 and Comparative Examples 3-1 to 3-7

Resist Test 2 (ArF Lithography)

On a substrate, a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition in Table 4 was spin coated, then baked on a hot plate at 100° C. for 60 seconds to form a resist film of 100 nm thick. Using an ArF excimer laser immersion lithography scanner NSR-610C (Nikon Corp., NA 1.30, a 0.98/0.78, 4/5 annular illumination), pattern exposure was performed through Mask A or B described below.

Mask A is a 6% halftone phase shift mask bearing a line pattern with a pitch of 100 nm and a line width of 50 nm (on-wafer size). After exposure through Mask A, the wafer was baked (PEB) for 60 seconds and developed. Specifically, butyl acetate was injected from a development nozzle while the wafer was spun at 30 rpm for 3 seconds, which was followed by stationary puddle development for 27 seconds. As a result, the unexposed regions which had been masked with Mask A were dissolved in the developer, that is, image reversal took place to form a line-and-space (L/S) pattern with a space width of 50 nm and a pitch of 100 nm.

Mask B is a 6% halftone phase shift mask bearing a line pattern with a pitch of 200 nm and a line width of 45 nm (on-wafer size). After exposure through Mask B, the wafer was baked (PEB) for 60 seconds and developed. Specifically, butyl acetate was injected from a development nozzle while the wafer was spun at 30 rpm for 3 seconds, which was followed by stationary puddle development for 27 seconds. As a result, the unexposed regions which had been masked with Mask B were dissolved in the developer, that is, image reversal took place to form an isolated space pattern (referred to as "trench pattern", hereinafter) with a space width of 45 nm and a pitch of 200 nm.

Evaluation of Sensitivity

As an index of sensitivity, the optimum dose (Eop, mJ/cm$^2$) which provided an L/S pattern with a space width of 50 nm and a pitch of 100 nm on exposure through Mask A was determined.

Evaluation of Line Width Roughness (LWR)

An L/S pattern was formed by exposure in the optimum dose (determined in the sensitivity evaluation) through Mask A (in Resist Test 2). By observation under TDSEM S-9380 (Hitachi Hitechnologies, Ltd.), the space width was measured at longitudinally spaced apart 10 points, from which a 3-fold value (3σ) of standard deviation (σ) was determined and reported as LWR. A smaller value of 3σ indicates a pattern having a lower roughness and more uniform space width.

Evaluation of Mask Error Factor (MEF)

An L/S pattern was formed by exposure in the optimum dose (determined in the sensitivity evaluation) through Mask A with the pitch fixed and the line width varied. MEF was calculated from variations of the mask line width and the pattern space width according to the following equation:

MEF=(pattern space width)/(mask line width)−$b$ wherein b is a constant. A value closer to unity (1) indicates better performance.

Evaluation of Depth-of-Focus (DOF) Margin

The exposure dose and DOF which ensured to form a trench pattern with a space width of 35 nm on exposure through Mask B were defined as the optimum exposure dose and the optimum DOF, respectively. The depth (nm) over which focus was changed that could form a resist pattern with a space width of 35 nm±10% (i.e., 31.5 nm to 38.5 nm) was determined and reported as DOF. A larger value indicates a smaller change of pattern size with a change of DOF and hence, better DOF margin.

The results are shown in Table 6.

TABLE 6

| | | Resist | Eop (mJ/cm$^2$) | LWR (nm) | MEF | DOF (nm) |
|---|---|---|---|---|---|---|
| Example | 3-1 | R-1 | 31 | 3.0 | 3.1 | 120 |
| | 3-2 | R-2 | 33 | 3.2 | 3.0 | 130 |
| | 3-3 | R-3 | 35 | 3.3 | 3.0 | 130 |
| | 3-4 | R-4 | 33 | 3.0 | 3.0 | 120 |
| | 3-5 | R-5 | 32 | 3.3 | 3.2 | 120 |
| | 3-6 | R-6 | 32 | 3.1 | 3.0 | 130 |
| | 3-7 | R-7 | 33 | 3.2 | 2.8 | 130 |
| | 3-8 | R-8 | 31 | 3.3 | 2.7 | 130 |
| | 3-9 | R-9 | 31 | 3.1 | 2.9 | 120 |
| | 3-10 | R-10 | 32 | 3.2 | 3.0 | 130 |
| | 3-11 | R-11 | 34 | 3.2 | 3.0 | 120 |
| | 3-12 | R-12 | 32 | 3.3 | 3.1 | 110 |
| | 3-13 | R-13 | 32 | 3.0 | 2.9 | 130 |
| | 3-14 | R-14 | 32 | 3.3 | 2.7 | 120 |
| Comparative Example | 3-1 | R-15 | 38 | 4.7 | 4.6 | 70 |
| | 3-2 | R-16 | 33 | 4.3 | 4.7 | 70 |
| | 3-3 | R-17 | 36 | 4.4 | 4.4 | 75 |
| | 3-4 | R-18 | 37 | 4.6 | 4.6 | 80 |
| | 3-5 | R-19 | 35 | 4.3 | 4.7 | 75 |
| | 3-6 | R-20 | 34 | 4.2 | 4.7 | 75 |
| | 3-7 | R-21 | 41 | 4.3 | 4.7 | 70 |

As seen from the results of Table 6, the resist compositions within the scope of the invention form negative patterns via organic solvent development with the advantages of improved LWR, MEF and DOF. The compositions are advantageously applicable to form patterns of fine feature size by lithography.

While the invention has been illustrated and described in typical embodiments, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims.

Japanese Patent Application No. 2014-226553 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An onium salt compound having the general formula (1):

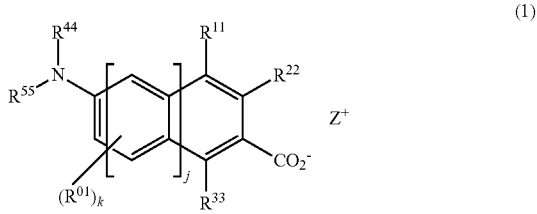

wherein $R^{11}$, $R^{22}$, $R^{33}$ and $R^{01}$ are each independently hydrogen, or a straight $C_1$-$C_{20}$ or branched or cyclic $C_3$-$C_{20}$ monovalent hydrocarbon group which may be substituted with or separated by a heteroatom, a pair of $R^{11}$ and $R^{22}$, or $R^{33}$ and $R^{01}$ may bond together to form a ring with the carbon atoms to which they are attached, $R^{44}$ and $R^{55}$ are each independently a straight $C_1$-$C_{20}$ or branched or cyclic $C_3$-$C_{20}$ monovalent hydrocarbon group which may be substituted with or separated by a heteroatom, a pair of $R^{44}$ and $R^{55}$ may bond together to form a ring with the nitrogen atom to which they are attached, the ring may have an oxygen atom, sulfur atom or NH moiety interposed therein, j is 0 or 1, k is a number in the range: $0 \leq k \leq 1$ when $j=0$ and $0 \leq k \leq 3$ when $j=1$, $Z^+$ is a sulfonium cation of the general formula (a) or iodonium cation of the general formula (b):

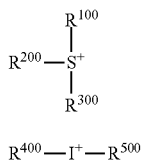

(a)

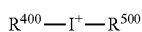

(b)

wherein $R^{100}$, $R^{200}$ and $R^{300}$ are each independently a straight $C_1$-$C_{20}$ or branched or cyclic $C_3$-$C_{20}$ monovalent hydrocarbon group which may be substituted with or separated by a heteroatom, or any two or more of $R^{100}$, $R^{200}$ and $R^{300}$ may bond together to form a ring with the sulfur atom, the ring may have a carbonyl moiety, sulfur atom, S(=O) moiety, $SO_2$ moiety, oxygen atom, or NH moiety interposed therein, $R^{400}$ and $R^{500}$ are each independently a straight $C_1$-$C_{20}$ or branched or cyclic $C_3$-$C_{20}$ monovalent hydrocarbon group which may be substituted with or separated by a heteroatom.

2. A resist composition comprising
(A) the onium salt compound of claim 1,
(B) a polymer,
(C) a photoacid generator, and
(D) an organic solvent,
said polymer comprising recurring units having the general formulae (2) and (3):

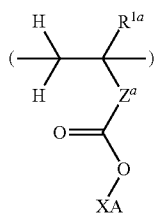

(2)

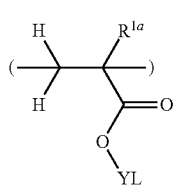

(3)

wherein $R^{1a}$ is hydrogen, fluorine, methyl or trifluoromethyl, $Z^a$ is a single bond, phenylene, naphthylene or (backbone)-C(=O)—O—Z'—, Z' is a straight $C_1$-$C_{10}$ or branched or cyclic $C_3$-$C_{10}$ alkylene group which may contain a hydroxyl moiety, ether bond, ester bond or lactone ring, or phenylene or naphthylene group, XA is an acid labile group, and YL is hydrogen or a polar group having at least one structure selected from the group consisting of hydroxyl, cyano, carbonyl, carboxyl, ether bond, ester bond, sulfonate bond, carbonate bond, lactone ring, sultone ring, and carboxylic anhydride.

3. The resist composition of claim 2 wherein the polymer further comprises recurring units (d1) or (d2) having the general formula:

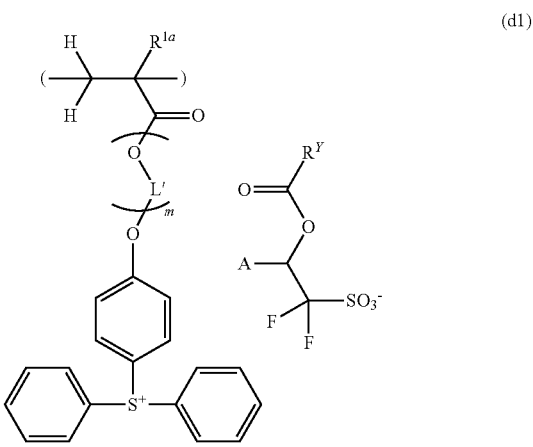

(d1)

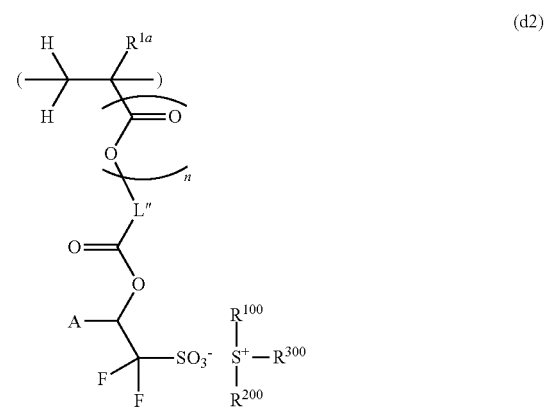

(d2)

wherein $R^{1a}$, $R^{100}$, $R^{200}$ and $R^{300}$ are is as defined above, L' is a $C_2$-$C_5$ alkylene group, $R^Y$ is a straight $C_1$-$C_{20}$ or branched or cyclic $C_3$-$C_{20}$ monovalent hydrocarbon group which may be substituted with or separated by a heteroatom, A is hydrogen or trifluoromethyl, L" is a single bond or a straight $C_1$-$C_{20}$ or branched or cyclic $C_3$-$C_{20}$ divalent hydrocarbon group which may be substituted with or separated by a heteroatom, m is 0 or 1, n is 0 or 1, with the proviso that n is 0 when L" is a single bond.

4. The resist composition of claim 2 wherein the photoacid generator has the general formula (4):

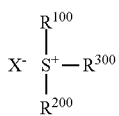

(4)

wherein $R^{100}$, $R^{200}$, and $R^{300}$ are as defined above, $X^-$ is an anion of any one of the general formulae (5) to (8):

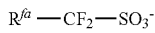

(5)

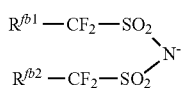

(6)

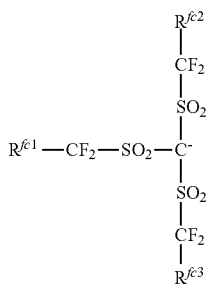

(7)

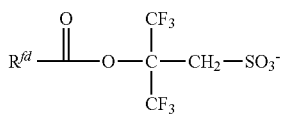

(8)

wherein $R^{fa}$, $R^{fb1}$, $R^{fb2}$, $R^{fc1}$, $R^{fc2}$, and $R^{fc3}$ are each independently fluorine or a straight $C_1$-$C_{40}$ or branched or cyclic $C_3$-$C_{40}$ monovalent hydrocarbon group which may be substituted with or separated by a heteroatom, $R^{fb1}$ and $R^{fb2}$, or $R^{fc1}$ and $R^{fc2}$ may bond together to form a ring with the segments to which they are attached, $R^{fd}$ is a straight $C_1$-$C_{40}$ or branched or cyclic $C_3$-$C_{40}$ monovalent hydrocarbon group which may be substituted with or separated by a heteroatom.

5. The resist composition of claim 2, further comprising a nonionic nitrogen-containing compound.

6. The resist composition of claim 2, further comprising a surfactant which is insoluble or substantially insoluble in water and soluble in alkaline developer and/or a surfactant which is insoluble or substantially insoluble in water and alkaline developer.

7. A pattern forming process comprising the steps of applying the resist composition of claim 2 onto a substrate, prebaking to form a resist film, exposing the resist film to KrF excimer laser, ArF excimer laser, EB or EUV through a photomask, baking, and developing the exposed resist film in a developer.

8. The pattern forming process of claim 7 wherein the exposing step is by immersion lithography wherein a liquid having a refractive index of at least 1.0 is interposed between the resist film and a projection lens.

9. The pattern forming process of claim 8, further comprising the step of forming a protective film on the resist film, and in the immersion lithography, the liquid is interposed between the protective film and the projection lens.

10. The onium salt compound of claim 1 wherein $R^{44}$ and $R^{55}$ bond together to form a ring with the nitrogen atom to which they are attached, and the ring may have an oxygen atom, sulfur atom or NH moiety interposed therein.

11. The onium salt compound of claim 10 wherein the ring is selected from the group consisting of the following structures:

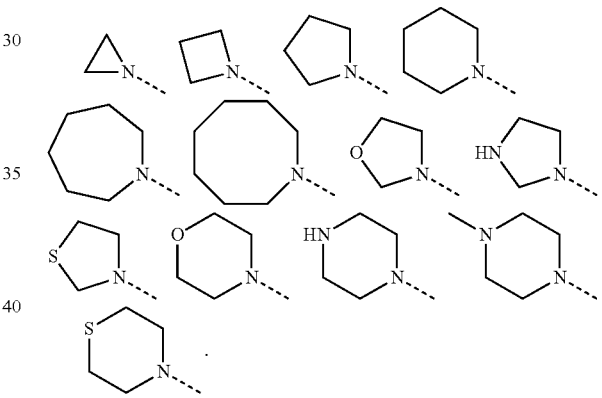

* * * * *